(12) United States Patent
Ramiya

(10) Patent No.: US 11,299,511 B2
(45) Date of Patent: Apr. 12, 2022

(54) OLIGONUCLEOTIDE COMPOSITIONS AND METHODS OF MAKING THE SAME

(71) Applicant: Geron Corporation, Menlo Park, CA (US)

(72) Inventor: Premchandran H. Ramiya, San Ramon, CA (US)

(73) Assignee: Geron Corporation, Foster City, CA (US)

( * ) Notice: Subject to any disclaimer, the term of this patent is extended or adjusted under 35 U.S.C. 154(b) by 646 days.

(21) Appl. No.: 15/705,021

(22) Filed: Sep. 14, 2017

(65) Prior Publication Data

US 2018/0016294 A1 Jan. 18, 2018

Related U.S. Application Data

(62) Division of application No. 14/699,902, filed on Apr. 29, 2015, now Pat. No. 9,796,747.

(60) Provisional application No. 62/151,909, filed on Apr. 23, 2015, provisional application No. 61/987,396, filed on May 1, 2014.

(51) Int. Cl.
*C07H 21/00* (2006.01)
*C12N 15/113* (2010.01)
*C12P 19/34* (2006.01)

(52) U.S. Cl.
CPC ........... *C07H 21/00* (2013.01); *C12N 15/113* (2013.01); *C12N 15/1137* (2013.01); *C12P 19/34* (2013.01); *C12N 2310/113* (2013.01); *C12N 2310/315* (2013.01); *C12N 2310/3145* (2013.01); *C12N 2310/3515* (2013.01); *C12Y 207/07049* (2013.01)

(58) Field of Classification Search
CPC .. C07H 21/00; C12N 15/113; C12N 15/1137; C12P 19/34
See application file for complete search history.

(56) References Cited

U.S. PATENT DOCUMENTS

| | | |
|---|---|---|
| 4,394,448 A | 7/1983 | Szoka, Jr. et al. |
| 4,659,774 A | 4/1987 | Webb et al. |
| 4,757,141 A | 7/1988 | Fung et al. |
| 4,897,355 A | 1/1990 | Eppstein et al. |
| 4,904,582 A | 2/1990 | Tullis |
| 4,958,013 A | 9/1990 | Letsinger |
| 5,185,444 A | 2/1993 | Summerton et al. |
| 5,411,947 A | 5/1995 | Hostetler et al. |
| 5,416,203 A | 5/1995 | Letsinger |
| 5,419,966 A | 5/1995 | Reed et al. |
| 5,420,330 A | 5/1995 | Brush |
| 5,476,925 A | 12/1995 | Letsinger et al. |
| 5,563,050 A | 10/1996 | Peyman et al. |
| 5,583,016 A | 12/1996 | Villeponteau et al. |
| 5,591,607 A | 1/1997 | Gryaznov et al. |
| 5,599,922 A | 2/1997 | Gryaznov et al. |
| 5,629,154 A | 5/1997 | Kim et al. |
| 5,631,135 A | 5/1997 | Gryaznov et al. |
| 5,646,260 A | 7/1997 | Letsinger et al. |
| 5,648,480 A | 7/1997 | Letsinger et al. |
| 5,656,638 A | 8/1997 | Gaeta et al. |
| 5,684,143 A | 11/1997 | Gryaznov et al. |
| 5,695,932 A | 12/1997 | West et al. |
| 5,726,297 A | 3/1998 | Gryaznov et al. |
| 5,760,062 A | 6/1998 | Gaeta et al. |
| 5,763,208 A | 6/1998 | Bischofberger et al. |
| 5,767,278 A | 6/1998 | Gaeta et al. |
| 5,770,613 A | 6/1998 | Gaeta et al. |
| 5,824,793 A | 10/1998 | Hirschbein et al. |
| 5,837,694 A | 11/1998 | Barrett |
| 5,837,835 A | 11/1998 | Gryaznov et al. |
| 5,840,490 A | 11/1998 | Bacchetti et al. |
| 5,846,723 A | 12/1998 | Kim et al. |

(Continued)

FOREIGN PATENT DOCUMENTS

| | | |
|---|---|---|
| CN | 1373768 | 10/2002 |
| JP | 4-503957 | 7/1992 |

(Continued)

OTHER PUBLICATIONS

U.S. Appl. No. 14/714,732, filed May 18, 2015, Gryaznov et al.
U.S. Appl. No. 14/720,466, filed May 22, 2015, Gryaznov et al.
U.S. Appl. No. 14/649,125, filed Jun. 2, 2015, Stuart, Monic J.
U.S. Appl. No. 14/720,467, filed May 22, 2015, Gryaznov et al.
"Cancer [online], [retrieved on Jul. 6, 2007] Retrieved from the Internet, URL: http://www.nlm.nih.gov/medlineplus/cancer.html".
The International Search Report from PCT/US2005/023633 filed Jun. 30, 2005.

(Continued)

*Primary Examiner* — Jezia Riley
(74) *Attorney, Agent, or Firm* — Rudy J. Ng; Bozicevic, Field & Francis LLP

(57) ABSTRACT

The present disclosure provides a solid phase method of making oligonucleotides via sequential coupling cycles including at least one coupling of a dinucleotide dimer subunit to a free 3'-terminal group of a growing chain. The oligonucleotides include at least two nucleoside subunits joined by a N3'→P5' phosphoramidate linkage. The method may include the steps of (a) deprotecting the protected 3' amino group of a terminal nucleoside attached to a solid phase support, said deprotecting forming a free 3' amino group; (b) contacting the free 3' amino group with a 3'-protected amino-dinucleotide-5'-phosphoramidite dimer in the presence of a nucleophilic catalyst to form an internucleoside N3'→P5' phosphoramidite linkage; and (c) oxidizing (e.g., sulfurizing) the linkage. The compositions produced by the subject methods may include a reduced amount of one or more (N−x) oligonucleotide products. Also provided are pharmaceutical compositions including the subject oligonucleotide compositions.

23 Claims, 14 Drawing Sheets

Specification includes a Sequence Listing.

(56) References Cited

U.S. PATENT DOCUMENTS

| | | |
|---|---|---|
| 5,856,461 A | 1/1999 | Colote et al. |
| 5,859,233 A | 1/1999 | Hirschbein et al. |
| 5,863,726 A | 1/1999 | Harley et al. |
| 5,863,936 A | 1/1999 | Gaeta et al. |
| 5,932,718 A | 8/1999 | Letsinger et al. |
| 5,952,490 A | 9/1999 | Hanecak et al. |
| 5,958,680 A | 9/1999 | Villeponteau et al. |
| 5,965,720 A | 10/1999 | Gryaznov et al. |
| 5,998,604 A | 12/1999 | Fearon et al. |
| 6,001,991 A | 12/1999 | Dean et al. |
| 6,015,710 A | 1/2000 | Shay et al. |
| 6,087,490 A | 7/2000 | Baxter et al. |
| 6,087,491 A | 7/2000 | Tang et al. |
| 6,153,737 A | 11/2000 | Manoharan et al. |
| 6,166,188 A | 12/2000 | Cook et al. |
| 6,169,170 B1 | 1/2001 | Gryaznov et al. |
| 6,221,850 B1 | 4/2001 | McKay et al. |
| 6,235,886 B1 | 5/2001 | Manoharan et al. |
| 6,261,836 B1 | 7/2001 | Cech et al. |
| 6,265,558 B1 | 7/2001 | Cook et al. |
| 6,331,399 B1 | 12/2001 | Monia et al. |
| 6,350,853 B1 | 2/2002 | Nielsen et al. |
| 6,368,789 B1 | 4/2002 | West et al. |
| 6,395,492 B1 | 5/2002 | Manoharan et al. |
| 6,444,650 B1 | 9/2002 | Cech et al. |
| 6,448,392 B1 | 9/2002 | Hostetler et al. |
| 6,548,298 B2 | 4/2003 | Villeponteau et al. |
| 6,608,036 B1 | 8/2003 | Gryaznov et al. |
| 6,683,826 B1 | 1/2004 | Matsuo et al. |
| 6,762,169 B1 | 7/2004 | Manoharan |
| 6,835,826 B2 | 12/2004 | Gryaznov et al. |
| 7,067,497 B2 | 6/2006 | Hanecak et al. |
| 7,138,383 B2 | 11/2006 | Gryaznov et al. |
| 7,485,717 B2 | 2/2009 | Gryaznov et al. |
| 7,494,982 B2 | 2/2009 | Gryaznov et al. |
| 7,563,618 B2 | 7/2009 | Gryaznov et al. |
| 7,989,428 B2 | 8/2011 | Go et al. |
| 7,998,938 B2 | 8/2011 | Moore et al. |
| 8,153,604 B2 | 4/2012 | Deen et al. |
| 8,440,635 B2 | 5/2013 | Gryaznov et al. |
| 8,748,593 B2 | 6/2014 | Gryaznov et al. |
| 9,388,415 B2 | 7/2016 | Gryaznov et al. |
| 9,388,416 B2 | 7/2016 | Gryaznov et al. |
| 9,404,112 B2 | 8/2016 | Gryaznov et al. |
| 9,657,296 B2 | 5/2017 | Gryaznov et al. |
| 9,796,747 B2 | 10/2017 | Ramiya |
| 10,392,418 B2 * | 8/2019 | Ramiya .................. C07H 21/00 |
| 2003/0096776 A1 | 5/2003 | Hanecak et al. |
| 2003/0138814 A1 | 7/2003 | Gryaznov et al. |
| 2005/0113325 A1 | 5/2005 | Gryaznov et al. |
| 2006/0040308 A1 | 2/2006 | Capaldi et al. |
| 2007/0015723 A1 | 1/2007 | Hanecak et al. |
| 2007/0037770 A1 | 2/2007 | Gryaznov et al. |
| 2007/0269870 A1 * | 11/2007 | Church .................. C12N 15/10 435/91.2 |
| 2007/0270363 A1 | 11/2007 | Bennett et al. |
| 2009/0175801 A1 | 7/2009 | Deen et al. |
| 2009/0286853 A1 | 11/2009 | Gryaznov et al. |
| 2012/0129918 A1 | 5/2012 | Gryaznov et al. |
| 2012/0329858 A1 | 12/2012 | Gryaznov et al. |
| 2013/0065950 A1 | 3/2013 | Gryaznov et al. |
| 2014/0163090 A1 | 6/2014 | Stuart |
| 2014/0349292 A1 | 11/2014 | Gryaznov et al. |
| 2015/0376624 A1 | 12/2015 | Gryaznov |
| 2018/0016293 A1 | 1/2018 | Ramiya et al. |

FOREIGN PATENT DOCUMENTS

| | | |
|---|---|---|
| JP | 2003-513887 | 4/2003 |
| JP | 2009-046483 | 3/2009 |
| JP | 4690324 | 2/2011 |
| WO | WO1990/010448 | 9/1990 |
| WO | WO1991/014696 | 10/1991 |
| WO | WO1994/008053 | 4/1994 |
| WO | WO1995/025814 | 9/1995 |
| WO | WO1996/01835 | 1/1996 |
| WO | WO1996/14277 | 5/1996 |
| WO | WO1997/31009 | 8/1997 |
| WO | WO1997/37691 | 10/1997 |
| WO | WO1997/38013 | 10/1997 |
| WO | WO1998/28442 | 7/1998 |
| WO | WO2001/18015 | 3/2001 |
| WO | WO2002/077184 | 10/2002 |
| WO | WO2004/029277 | 4/2004 |
| WO | WO2005/023994 | 3/2005 |
| WO | WO2006/014387 | 2/2006 |
| WO | WO2008/094640 | 8/2008 |

OTHER PUBLICATIONS

Asai, A. et al., "A Novel Telomerase Template Antagonist (GRN163) as a Potential Anticancer Agent", Cancer Res. 63, 2003, pp. 3931-3939.

Azhayev, Alexi et al., "Synthesis of phosphoramidate analogues of short oligoribonucleotides", Nucl. Acids Res. Symp. Series 9, 1981, 251-4.

Baraniak, J. et al., New Approach to the Solid Phase Synthesis of N3' P5' Phosphoramidate Oligonucleotides, Nucleosides & Nuc/eotides, 17(8):1347-1353, (1998).

Beaucage and Iyer, "Advances in the Synthesis of Oligonucleotides by the Phosphoramidite Approach" Tetrahedron 48: 2223-2311 (1992).

Chapuis, H. et al., "Shorter puromycin analog synthesis by means of an efficient Staudinger_Vilarrasa coupling", Tetrahedron 62 (2006) 12108-12115.

Chirila, T. et al., "The use of synthetic polymers for delivery of therapeutic antisense oligodeoxynucleotides", Biomaterials 23, 2002, pp. 321-342.

Chur, Anette et al., "Synthesis of a carboxamide linked T*T dimer and its incorporation in oligonucleotides", Nucleic Acids Research, vol. 21, No. 22, 1993, 5179-5183.

Crooke, S. et al., "Pharmacokinetic properties of several novel oligonucleotide analogs in mice", J. Pharmacol. Exp. Ther. 277(2), 1996, pp. 923-937.

Fiedler, A. et al., "Growth inhibition of pancreatic tumor cells by modified antisense oligodeoxynucleotides", Langenbeck's Arch. Surg. 383(3-4), 1998, pp. 269-275.

Froehler, B. et al., "Dialkylformamidines: depurination resistant N6-protecting group for deoxyadenosine", Nucleic Acids Research (1983), 11(22):8031-8036.

Gaytan, Paul et al., "Combination of DMT-mononucleotide and Fmoc-trinucleotide phosphoramidites in oligonucleotide synthesis affords an automatable codon-level mutagenesis method", Chemistry & Biology, vol. 5, No. 9, 1998, 519-527.

Gerster, M. et al., "Quantitative analysis of modified antisense oligonucleotides in biological fluids using cationic nanoparticles for solid-phase extraction", Anal. Biochem. 262(2), 1998, pp. 177-184.

Golub, et al., "Molecular Classification of Cancer: Class Discovery and Class Prediction by Gene Expression Monitoring", Science (1999), vol. 286, 531-537, 1999, 531-537.

Greene, et al. Protective Groups in Organic Synthesis, (1999), New York John Wiley & Sons, Inc., pp. 17-23 and 494-502.

Greene. Protective Groups in Organic Synthesis, Third Edition, John Wiley & Sons, Inc. 1999, p. 588.

Greene, T., et al., (1999), "Protective Groups in Organic Synthesis", John Wiley & Sons, Inc., New York, pp. 4-5, 119, 142-3, 513, 550, 559, 583-4.

Gryaznov, S. et al., "Modulation of oligonucleotide duplex and triplex stability via hydrophobic interactions", Nucl. Acids Res. 21, 1993, pp. 5909-5915.

Gryaznov, S. et al., "Synthesis and properties of oligonucleotides containing aminodeoxythymidine units", Nucl. Acids Res. 20(13), 1992, 3403-9.

Gryaznov, S. and Winter, H., RNA mimetics; oligoribonucleotide N3' P5' phosphoramidates, Nucleic Acids Research, 26(18):4160-4167, (1998).

(56) References Cited

OTHER PUBLICATIONS

Gryaznov, S., et al., (2003) "Oligonucleotide N3'-P5' Thio-phosphoramidate Telomerase Template Antagonists as Potential Anticancer Agents", Nucleosides, Nucleotides & Nucleic Acids, 22(5-8):577-581.
Gryaznov, S., et al., (2001) "Telomerase Inhibitors—Oligonucleotide Phosphoramidates as Potential Therapeutic Agents", Nucleosides, Nucleotides & Nucleic Acids, 20(4-7):401-410.
Hassler, Matthew et al., "RNA synthesis via dimer and trimer phosphoramidite block coupling", Tetrahedron Letters 52, 2011, 2575-2578.
Herdering, Wilhelm et al., "Phosphoramidites of Chiral (Rp)- and (Sp)-Configurated d(T[P-180]-A): Synthesis, Configurational Assignment, and Use as Dimer Blocks in Oligonucleotide Synthesis", Helvetica Chimica Acta vol. 68, 1985, 2119-2127.
Iyer et al., "The automated synthesis of sulfur-containing oligodeoxyribonucleotides using 3H-1,2-benzodithiol-3-one 1,1-dioxide as a sulfur-transfer reagent", J. Org. Chem., 1990, 55 (15), pp. 4693-4699.
Iyer, R. et al., "3H-1,2-benzodithiole-3-one 1,1-dioxide as an improved sulfurizing reagent in the solid-phase synthesis of oligodeoxyribonucleoside phosphothiorates", J. Am. Chem. Soc. 112, 1990, 1253-4.
Jen, K-Y. et al., "Suppression of gene expression by targeted disruption of messenger RNA: available options and current strategies", Stem Cells 18, 2000, pp. 307-319.
Kates et al. Solid-Phase Synthesis, A Practical Guide, Marcel Dekker, Inc. 2000, pp. 478-480.
Keppler, Brian et al., "Inhibition of Telomerase Activity by Preventing Proper Assemblage", Biochemistry 43, 2004, 334-343.
Lala, et al., "Role of Nitric Oxide in Tumor Progression: Lessons from Experimental Tumors", Cancer and Metastasis Reviews (1998), 17, 91-106, 1998, 91-106.
Liekens, S. et al., "The nucleoside derivative 5'-0-trityl-inosine (KIN59) suppresses thymidine phosphorylase-triggered angiogenesis via a noncompetitive mechanism of action," J. Bio!. Chern. 279(28):29598-605 (2004).
MacKellar, C. et al., "Synthesis and physical properties of anti-HIV antisense oligonucleotides bearing terminal lipophilic groups", Nucl. Acids Res. 20(13), 1992, pp. 3411-3417.
Manoharan, M., "Oligonucleotide conjugates as potential antisense drugs with improved uptake, biodistribution, targeted delivery, and mechanism of action", Antisense & Nucl. Acid Drug Dev. 12, 2002, pp. 103-128.
Manoharan, M. et al., "Cholic acid-oligonucleotide conjugates for antisense applications", Bioorg. Med. Chem. Lett. 4(8), 1994, pp. 1053-1060.
Matray, T. J. and Gryaznov, S. M., "Synthesis and properties of RNA analogsoligoribonucleotide N3' P5' phosphoramidates", Nucleic Acids Research, 27(20):3976-3985, (1999).
McCurdy et al., (1997) Tetrahedron Letters, 38:207-210.
Mignet, N. and Gryaznov, S., "Zwitterionic oligodeoxyribonucleotide N3' P5' phosphoramidates: synthesis and properties", Nucleic Acids Research, 26(2):431-438, (1998).
Mishra, R. et al., "Improved leishmanicidal effect of phosphorotio-ate antisense oligonucleotides by LDL-mediated delivery", Biochim. Biophys. Acta 1264(2), 1995, pp. 229-237.
Nakajima, K. et al., (1978), "Studies on Aziridine-2-carboxylic Acid. I. Synthesis of the Optically Active L-Aziridine-2-carboxylic Acid and its Derivatives", Bull Chern. Soc. Jpn. 51:1577.
Nelson, J.S. eta/., "N3' P5' Oligodeoxyribonucleotide Phosphoramidates: A New Method of Synthesis Based on a Phosphoramidite Amine-Exchange Reaction", J. Organic Chemistry, 62:7278-7287, (1997).
Nelson, P. et al., "Oligonucleotide labeling methods. 3. Direct labeling of oligonucleotides employing a novel, non-nucleosidic, 2-aminobutyl-1,3-propanediol backbone", Nucl. Acids Res. 20(23), 1992, pp. 6253-6259.
Ohkubo et al., Org. Lett., 2010, 12 (11), pp. 2496-2499.

Ono, Akira et al., "The synthesis of blocked triplet-phosphoramidites and their use in mutagenesis", Nucleic Acids Research, vol. 23, No. 22, 1995, 4677-4682.
Pongracz, K. and Gryaznov, S., "-Oiigodeoxyribonucleotide N3' P5' phosphoramidates: synthesis and duplex formation", Nucleic Acids Research, 26(4):1099-1106, (1998).
Pongracz, K. and Gryaznov, S., "Oligonucleotide N3' P5' thiophosphoramidates: synthesis and properties", Tetrahedron Letters, 40:7661-7664, (1999).
Pruzan, R. et al., "Allosteric inhibitors of telomerase: oligonucle-otide N3'→P5' phosporamidates", Nucl. Acids Res. 30(2), 2002, pp. 559-568.
Saison-Behmoaras, T. et al., "Short modified antisense oligonucle-otides directed against Ha-ras point mutation induce selective cleavage of the mRNA and inhibit T24 cells proliferation", EMBO J. 10(5), 1995, pp. 1111-1118.
Schirmeister-Tichy, H. et al., "Synthesis, Characterization, and Biological Activities of New Potential Antiviral agents: (2'-5') Adenylate trimer analogs containing 3'-deoxy-3'-(hexadecanoylamino)adenosine at the 2'-terminus", Helvetica Chimica Acta 82, 1999, pp. 597-613.
Shea, R. et al., "Synthesis, hybridization properties and antiviral activity of lipid-oligodeoxynucleotide conjugates", Nucl. Acids Res. 18(13), 1990, pp. 3777-3783.
Shea-Herbert, B. et al., "Inhibition of human telomerase in immortal human cells leads to progressive telomere shortening and cell death", Proc. Natl. Acad. Sci. USA 96(25), 1999, pp. 14276-14281.
Shea-Herbert, B. et al., "Oligonucleotide N3'→P5' phosphoramidates as efficient telomerase inhibitors", Oncogene 21, 2002, pp. 638-642.
Stein, C., "Is irrelevant cleavage the price of antisense efficacy?", Pharmacol. Ther. 85, 2000, pp. 231-236.
Ti, G. et al., "Transient protection: efficient one-flask syntheses of protected deoxynucleosides," J. Am. Chern. Soc. 104:1316-9 (1982).
Will, D. et al., "Attachment of Vitamin E Derivatives to Oligo-nucleotides during Solid-Phase Synthesis", Tetrahedron Lett. 33(19), 1992, pp. 2729-2732.
Zhang, et al. "An Efficient Synthesis of 3'-Amino-3'-deoxyguanosine from Guanosine," Helvetica Chi mica Acta—vol. 86 (2003) pp. 703-710.
Zhang, et al. "Synthesis of pCpCpA-3'-NH-phenylalanine as a ribosomal substrate", Organic Letters 2002, 4(21):3615-361.
Zielinski, W. et al., "Oligoaminonucleoside phosphoramidates. Oligomerization of dimers of 3'-amino-3'-deoxy-nucleotides (GC and CG) in aqueous solution", Nucl. Acids Res. 15(4), 1987, 1699-715.
Dong, (2003) "Solid-Phase Synthesis of Dipeptide-Conjugated Nucleosides and Their Interaction with RNA" Helvetica Chimica Acta, 86:3516-3524.
Goodnow, (1997), "Synthesis of Thymine, Cytosine, Adenine, and Guanine Containing N-Fmoc Protected Amino Acids: Building Blocks for Construction of Novel Oligonucleotide Backbone Analogs" Tetrahedron Letters, 38(18):3195-3198.
Fields, (1994), "Methods for Removing the Fmoc Group" Methods in Molecular Biology, Peptide Synthesis Protocols, 35(2):17-27.
Demirtas, (2002), "The Selective Protection and Deprotection of Ambident Nucleophiles with Parent and Substituted Triarylmethyls" Turk J Chem, 26:889-896.
Capaldi, DC et al. (2000) "Highly Efficient Solid Phase Synthesis of Oligonucleotide Analogs Containing Phosphorodithioate Linkages", Nucleic Acids Res., 28(9):E40.
Chen, JJ et al. (2009) "N2'→P3' Phosphoramidate Glycerol Nucleic Acid as a Potential Alternative Genetic System", J Am Chern Soc., , 131(6):2119-2121.
Fearon, KL et al. (1995) "Investigation of the 'N-1' Impurity in Phosphorothioate Oligodeoxynucleotides Synthesized by the Solid-Phase-Cyanoethyl Phosphoramidate Method Using Stepwise Sulfurization", Nucleic Acids Research, 23(14):2754-2761.
Herbert, Brittney-Shea, et al., (2005) "Lipid modification of GRN163, an N3'-P5' thio-phosphoramidate oligonucleotide, enhances the potency of telomerase inhibition", Oncogene, 24:5262-5268.
Kumar, G. and Poonian M. S., (1984) "Improvements in Oligodeoxyribonucleotide Synthesis: Methyl N,N-

(56) References Cited

OTHER PUBLICATIONS

Dialkylphosphoramidite Dimer Units for Solid Support Phosphite Methodology", J. Org. Chem, 49(25):4905-4912.
Stetsenko et al., (2001) "A Convenient Solid-Phase Method for Synthesis of 3'-Conjugates of Oligonucleotides", Bioconjugate Chem., (12):576-586.
U.S. Appl. No. 15/705,021, filed Sep. 14, 2015, Ramiya.
Amarnath, et al., "Chemical Synthesis of Oligonucleotides", Chemical Reviews 77(2), 1977, 183-217.
Chen, et al., "Synthesis of oligodeoxyribonucleotide N3'→P5' phosphoramidates", Nucleic Acids Res. 23, 1995, 2661-2668.
Gryaznov, S. et al. (1990) "A New Method for the Synthesis of Oligodeoxyribonucleotides Containing Internucleotide Phosphoramidate Bonds," Tetrahedron Letters, vol. 31, No. 22, pp. 3205-3208.
Gryaznov, "Oligonucleotide N3'→P5' phosphoramidates", Proc. Natl. Acad. Sci. USA 92, 1995, 5798-5802.
Gryaznov, S. et al., "Oligonucleotide N3'→P5' phosphoramidates as antisense agents", Nucl. Acids Res. 24(8), 1996, pp. 1508-1514.
Gryaznov, Sergei et al., "Oligonucleotide N3'→P5' phosphoramidates as potential therapeutic agents", Biochim. Biophys. Acta 1489(1), 1999, 131-40.
Kupihar, Z. et al., "Synthesis and application of a novel, crystalline phosphoramidite monomer with thiol terminus, suitable for the synthesis of DNA conjugates", Bioorg. Med. Chem. 9(5), (2001), pp. 1241-1247.
Micklefield, J, "Backbone modification of nucleic acids: synthesis, structure and therapeutic applications", Current Medicinal Chemistry, 8(10), 2001, 1157-1179.
Ohtsuka, et al., "Recent Developments in the Chemical Synthesis of Polynucleotides", Nucleic Acids Research 10(21), 1982, 6553-6570.
Pon, et al., "Derivatization of Controlled Pore Glass Beads for Solid Phase Oligonucleotide Synthesis", Biotechniques 6, 1988, 768-775.
Pongracz, Krisztina et al., "Novel Short Oligonucleotide Conjugates as Inhibitors of Human Telomerase", Nucleosides, Nucleotides & Nucleic Acids 22(5-8), 2003, 1627-1629.
Thiviyanathan, V. et al., "Structure of hybrid backboe methylphosphonate DNA heteroduplexes: effect of R and S stereochemistry", Biochemistry, 41(3), 2002, 827-838.
Uhlmann, E. et al., "Antisense oligonucleotides: a new therapeutic principle", Chem. Rev. 90, (1990), pp. 543-584.
Blackburn, E., "Telomerases", Annu. Rev. Biochem. 61, 1992, pp. 113-129.
Chen, J. et al., "Secondary structure of vertebrate telomerase RNA", Cell 100, 2000, pp. 503-514.
Damm, K. et al., "A highly selective telomerase inhibitor limiting human cancer cell proliferation", EMBO J. 20(24), 2001, 6958-68.
Feng, J. et al., "The RNA component of human telomerase", Science 269, 1995, 1236-41.
Kim, M. et al., "A low threshold level of expression of mutant-template telomerase RNA inhibits human tumor cell proliferation", Proc. Natl. Acad. Sci. USA 98(14), 2001, pp. 7982-7987.
Kim, N. et al., "Specific association of human telomerase activity with immortal cells and cancer", Science 266, 1994, pp. 2011-2015.
Lichsteiner, et al., Annal New York Acad. Sci. 886, 1999, 1-11.
Miller, A.D., "The problem with cationic liposome/micelle-based non-viral vector systems for gene therapy", Current Medicinal Chemistry 10(14), 2003, 1195-1211.
Pedroso De Lima, M.C et al., "Cationic liposomes for gene delivery: from biophysics to biological applications", Current Medicinal Chemistry, 10(14), 2003, 1221-1231.
Petersen, M et al., "LNA: a versatile tool for therapeutics and genomics", Trends in Biotechnology, 21(2), 2003, 74-81.
Rump, E. et al., "Preparation of conjugates of oligodeoxynucleotides and lipid structures and their interaction with low-density lipoprotein", Bioconjugate Chem. 9, (1998), pp. 341-349.
Skorski, T. et al., "Antileukemia effect of c-myc N3'→P5' phosphoramidate antisense oligonucleotides in vivo", Proc. Natl. Acad. Sci. USA 94, 1997, pp. 3966-3971.
Von Janta-Lipinski, M et al., "Protein and RNA of Human Telomerase as Targets for Modified Oligonucleotides", Nucleosides and Nucleotides, 18(6-7), 1999, 1719-1720.
Wang, Eunice S. et al., "Telomerase inhibition with an oligonucleotide telomerase template antagonist: in vitro and in vivo studies in multiple myeloma and lymphoma", Blood, 103(1), 2004, 258-266.
Weinrich, S. et al., "Reconstitution of human telomerase with the template RNA component hTR and the catalytic protein subunit hTRT", Nat. Genet. 17(4), Dec. 1997, 498-502.
U.S. Appl. No. 15/705,019, filed Sep. 14, 2017, Ramiya.
Gryaznov, S. , et al., (1998) "RNA mimetics: oligoribonucleotide N3'-P5' phosphoramidates", Nucl. Acids Res. 26(18), pp. 4160-4167.
Obika, Satoshi, et al. (2008) "Synthesis and properties of 3'-amino-2',4'-BNA, a bridged nucleic acid with a N3'-P5' phosphoramidate linkage", Bioorganic & Medicinal Chemistry, 16(20):9230-9237.

\* cited by examiner

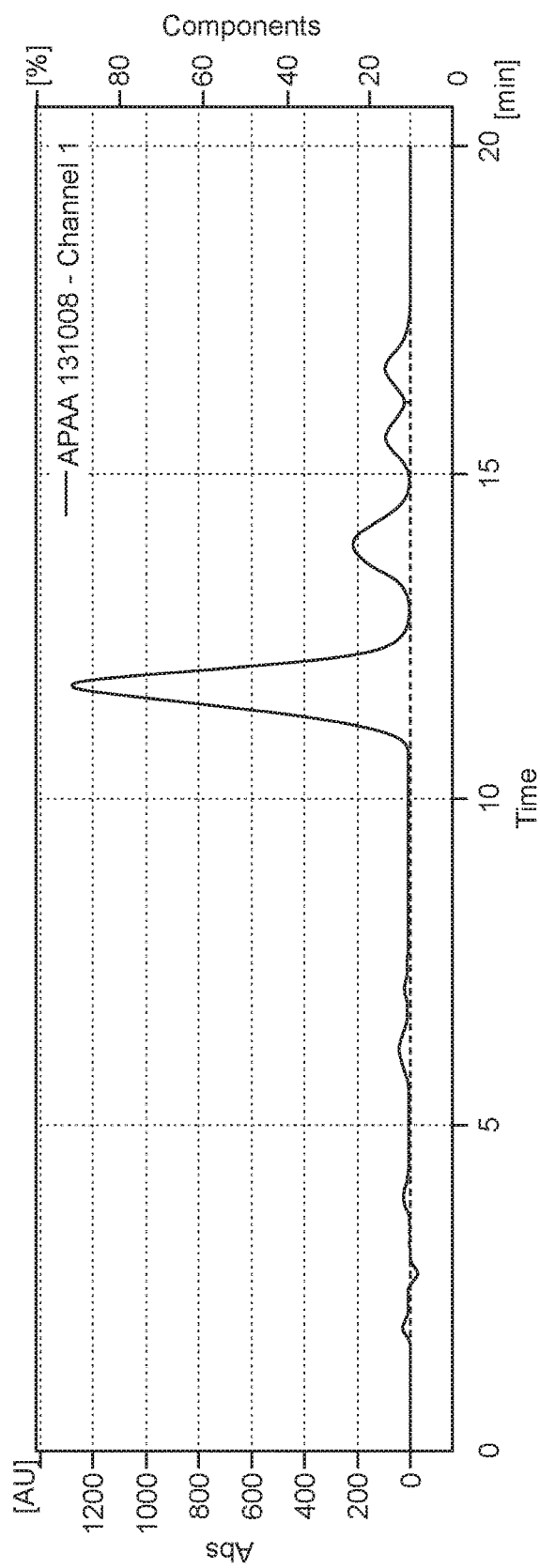

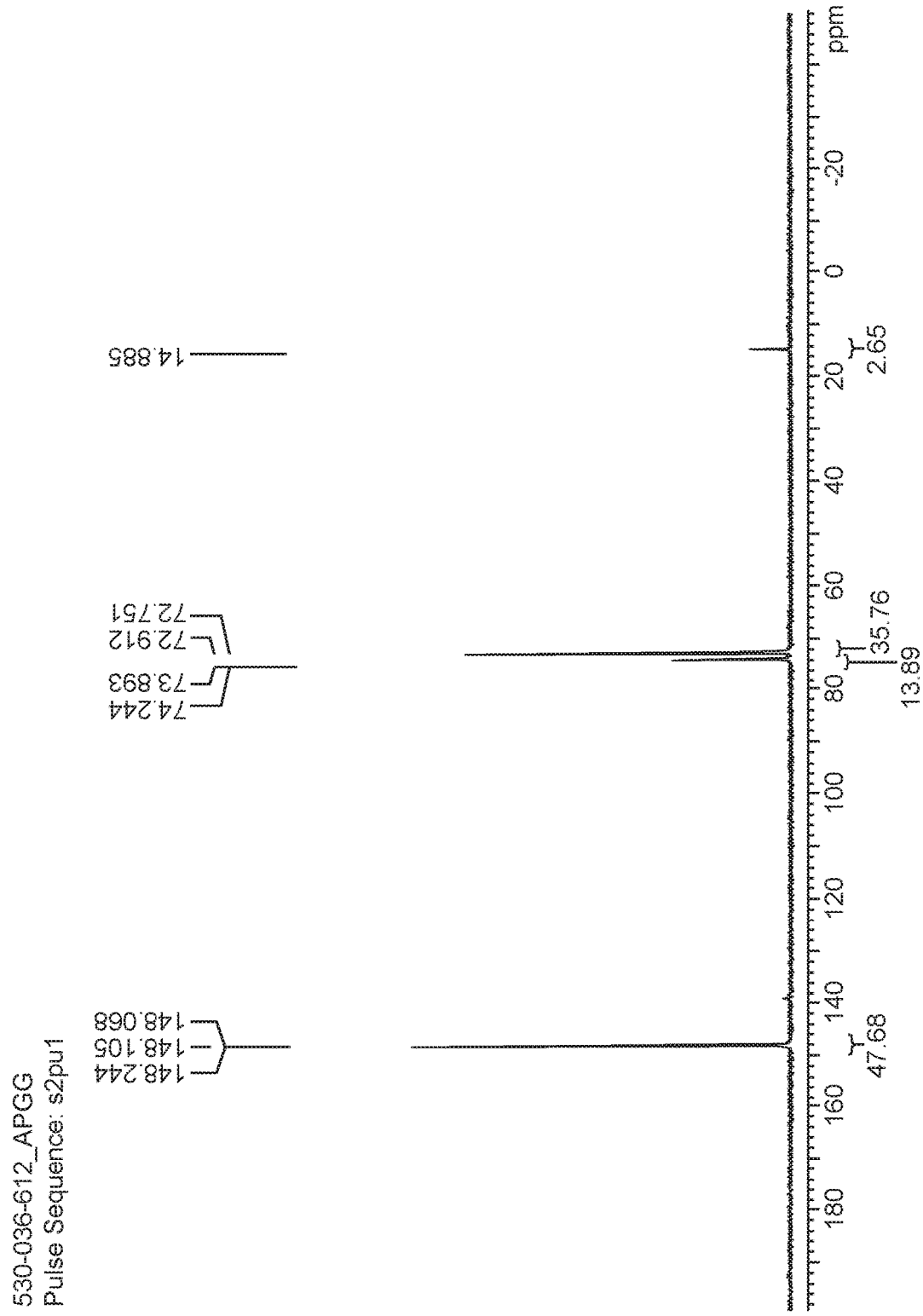

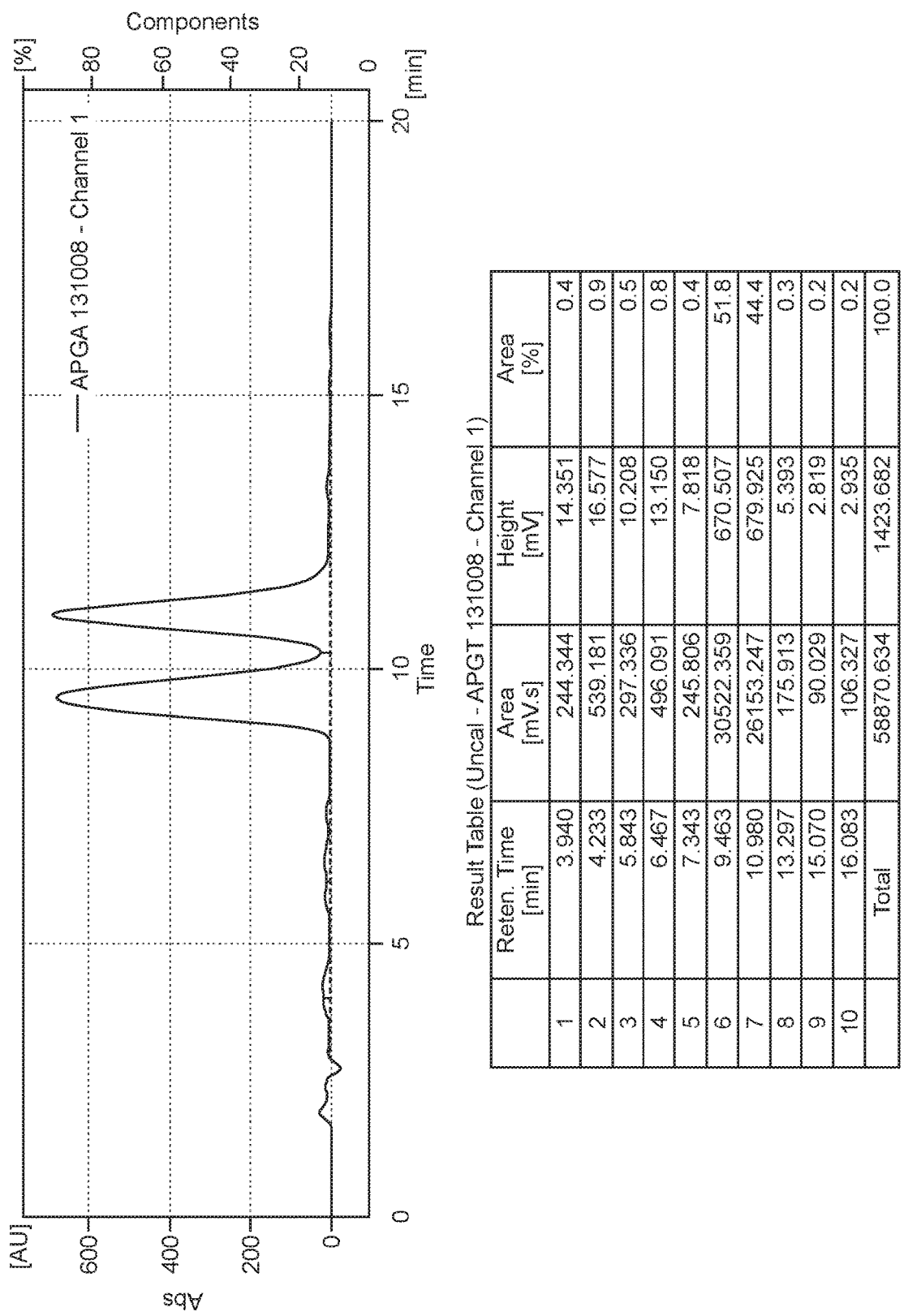

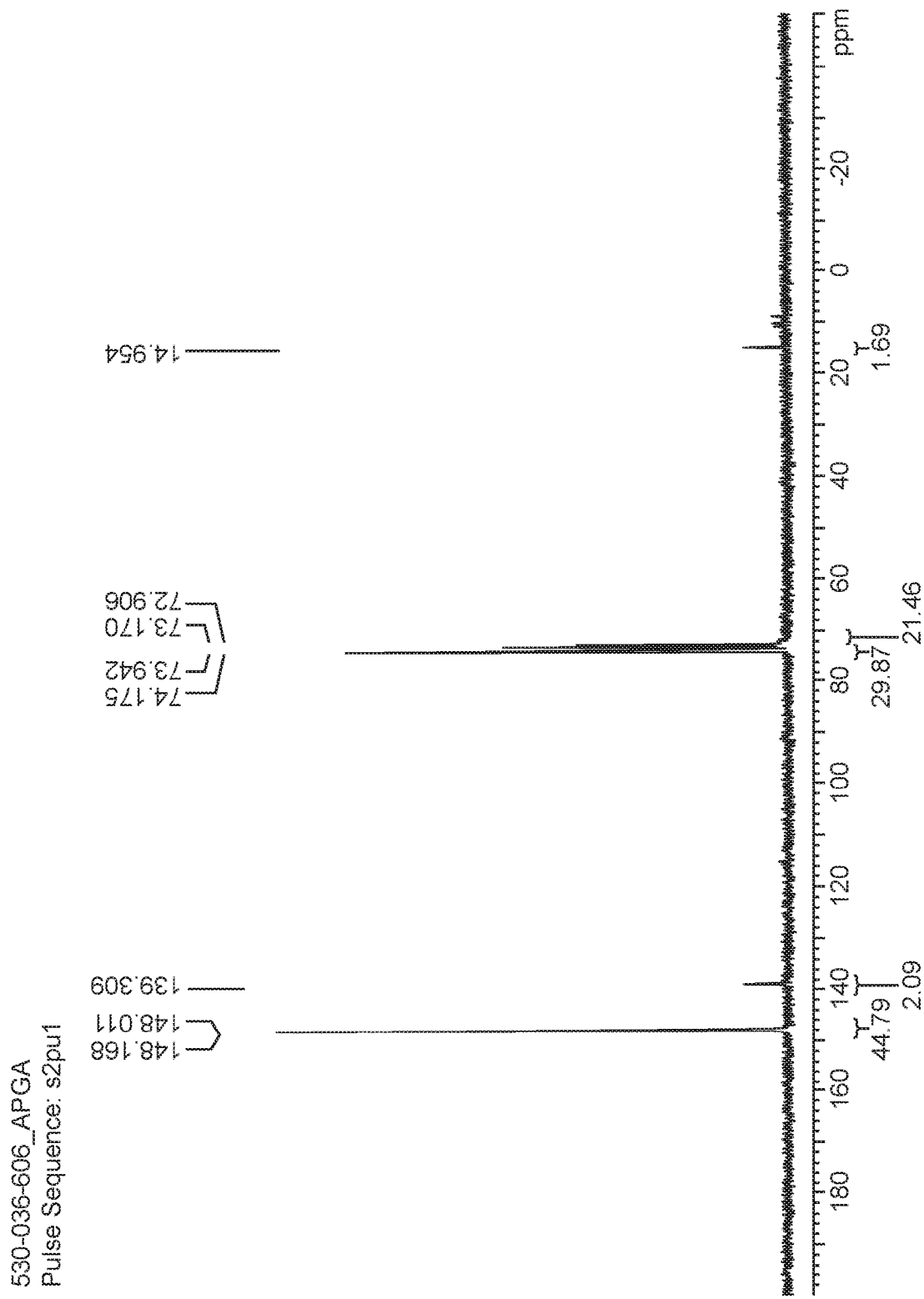

FIG. 6B
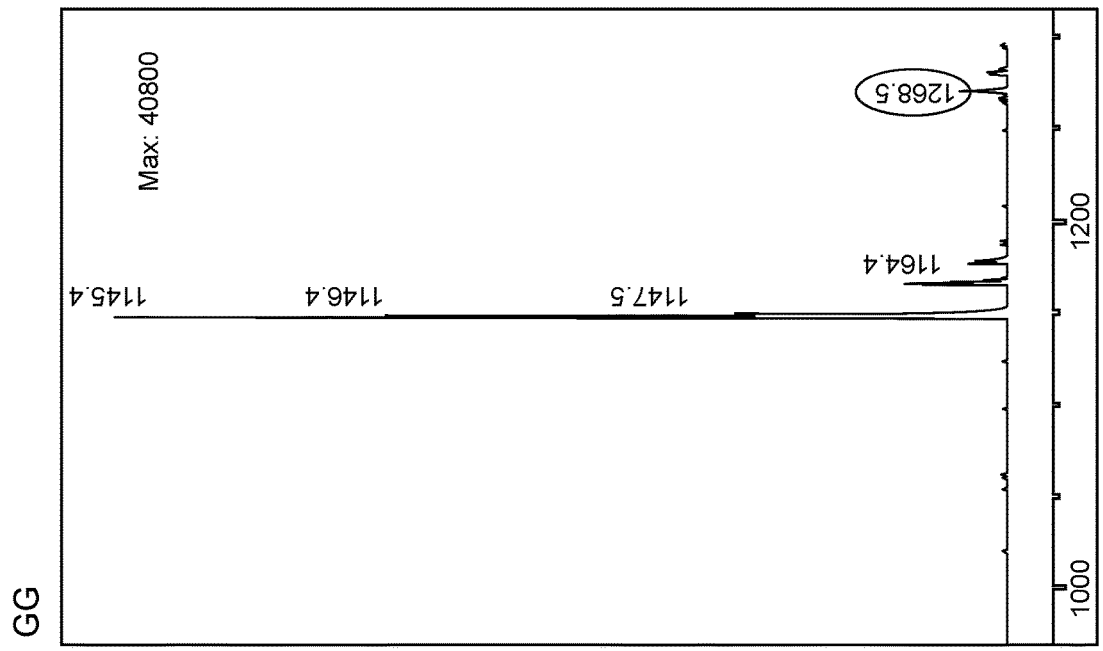
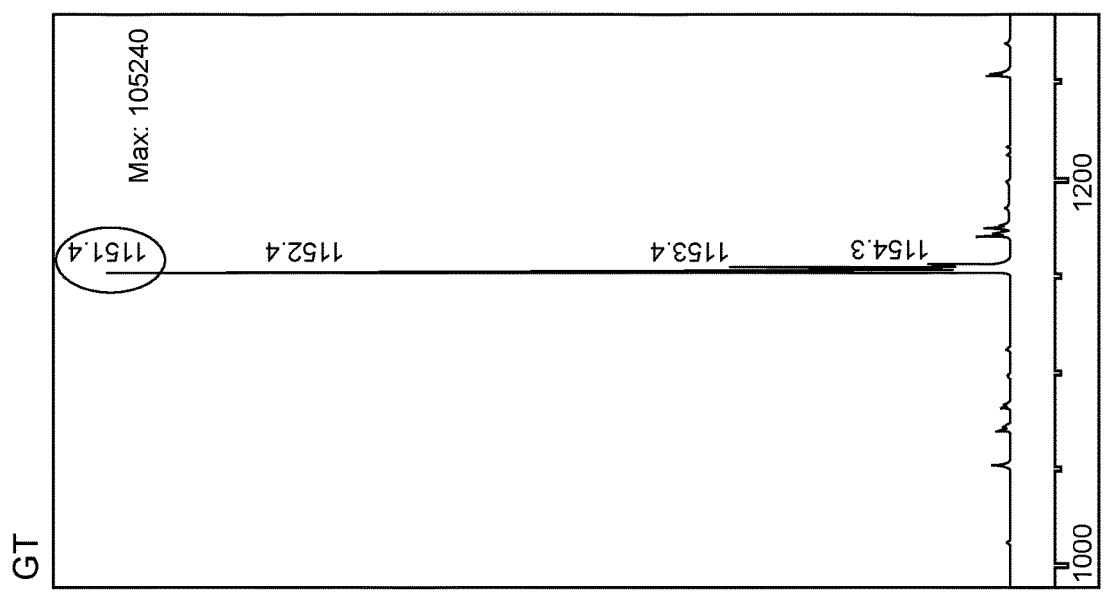

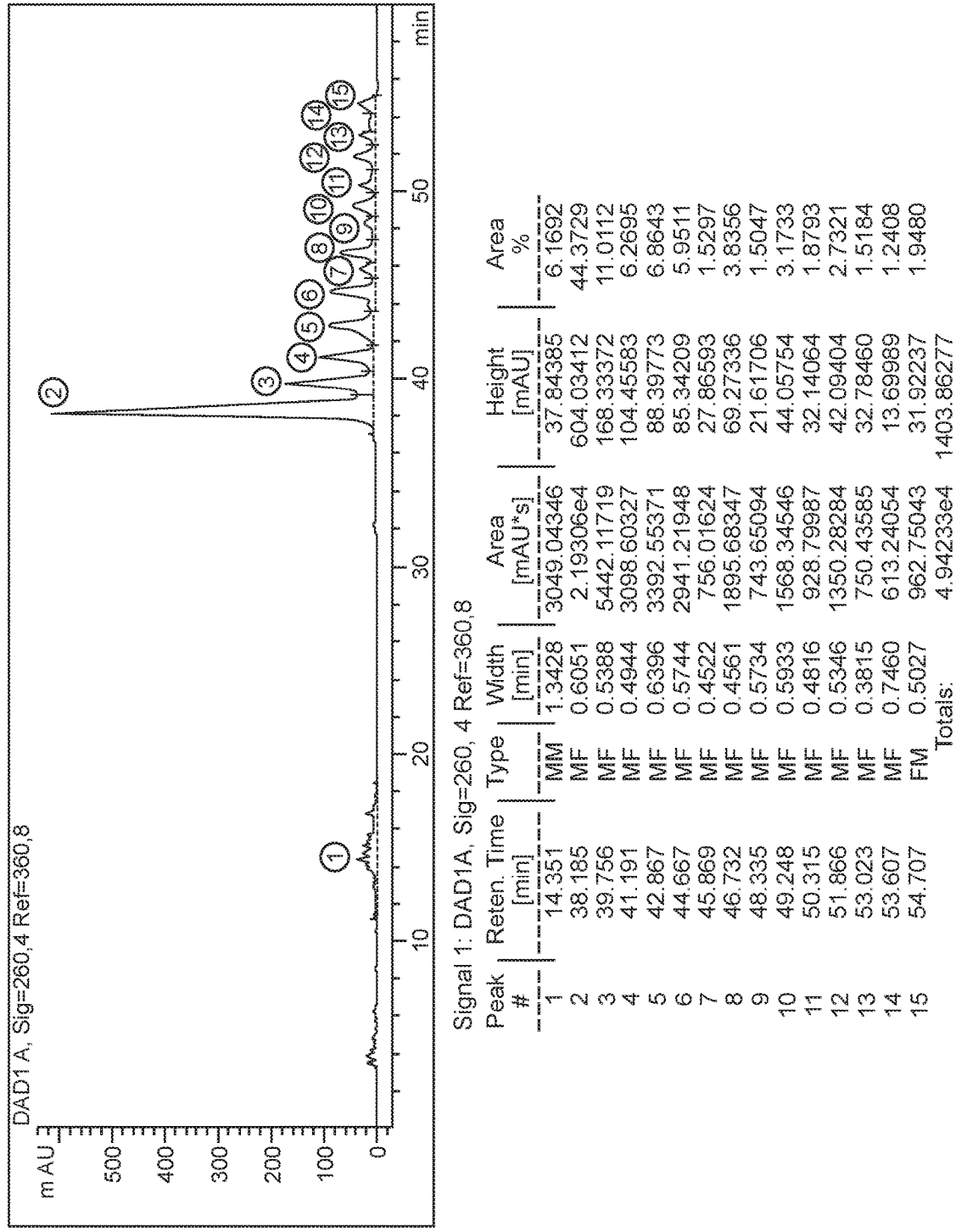

```
                      SEQUENCE LISTING

<160> NUMBER OF SEQ ID NOS: 19

<210> SEQ ID NO 1
<211> LENGTH: 451
<212> TYPE: RNA
<213> ORGANISM: Homo sapiens
<220> FEATURE:
<223> OTHER INFORMATION: Synthetic polynucleotide

<400> SEQUENCE: 1
ggguugcgga gguggggccu gggaggggug guggccauuu uuugucuaac ccuaacugag      60
aagggcguag cgccgugcu uuugcuccccc gcgcgcuguu uuucucgcug acuuucagcg    120
ggcggaaaag ccucggccug ccgccuucca ccguucauuc uagagcaaac aaaaaauguc    180
agcugcuggc ccguucgccc cucccgggga ccugcggcgg gucgccugcc cagccccga    240 accccgccug gaggccgcgg ucggcccggg gcuucuccgg aggcacccac ugccaccgcg    300
aagaguuggg cucugucagc cgcgggucuc ucggggggcga gggcgagguu caggccuuuc    360
aggccgcagg aagaggaacg gagcgagucc ccgcgcgcgg cgcgauuccc ugagcugugg    420
gacgugcacc caggacucgg cucacacaug c                                   451

<210> SEQ ID NO 2
<211> LENGTH: 11
<212> TYPE: RNA
<213> ORGANISM: Artificial Sequence
<220> FEATURE:
<223> OTHER INFORMATION: Synthetic polynucleotide

<400> SEQUENCE: 2
cuaacccuaa c                                                          11

<210> SEQ ID NO 3
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 3
tagggttaga caa                                                        13
```

<210> SEQ ID NO 4
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 4
gttagggtta g                                                          11

<210> SEQ ID NO 5
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 5
cagttagggt tag                                                        13

<210> SEQ ID NO 6
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 6
gctctagaat gaacggtgga aggcggcagg                                      30

<210> SEQ ID NO 7
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 7
gtggaaggcg gcagg                                                      15

<210> SEQ ID NO 8
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 8
ggaaggcggc agg                                                        13

<210> SEQ ID NO 9
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 9
gtggaaggcg gca                                                        13

<210> SEQ ID NO 10
<211> LENGTH: 11
<212> TYPE: DNA
<213> ORGANISM: Artificial Sequence
<220> FEATURE:
<223> OTHER INFORMATION: Synthetic polynucleotide

<400> SEQUENCE: 10
gtggaaggcg g                                                        11

<210> SEQ ID NO 11
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 11
cggtggaagg cgg                                                      13

<210> SEQ ID NO 12
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 12
acggtggaag gcg                                                      13

<210> SEQ ID NO 13
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 13
aacggtggaa ggcggc                                                   16

<210> SEQ ID NO 14
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 14
atgaacggtg gaaggcgg                                                 18

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide

```
<400> SEQUENCE: 15 acatttttg tttgctctag                                            20

<210> SEQ ID NO 16
<211> LENGTH: 13
<212> TYPE: DNA
<213> ORGANISM: Artificial Sequence
<220> FEATURE:
<223> OTHER INFORMATION: Synthetic polynucleotide

<400> SEQUENCE: 16
gttagggtta gac                                                  13

<210> SEQ ID NO 17
<211> LENGTH: 15
<212> TYPE: DNA
<213> ORGANISM: Artificial Sequence
<220> FEATURE:
<223> OTHER INFORMATION: Synthetic polynucleotide

<400> SEQUENCE: 17
gttagggtta gacaa                                                15

<210> SEQ ID NO 18
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 18
cccttctcag tt                                                   12

<210> SEQ ID NO 19
<211> LENGTH: 12
<212> TYPE: DNA
<213> ORGANISM: Artificial Sequence
<220> FEATURE:
<223> OTHER INFORMATION: Synthetic polynucleotide

<400> SEQUENCE: 19
cgcccttctc ag                                                   12
```

OLIGONUCLEOTIDE COMPOSITIONS AND METHODS OF MAKING THE SAME

CROSS REFERENCE TO RELATED APPLICATIONS

Pursuant to 35 U.S.C. § 119(e), this application claims priority to the filing dates of U.S. provisional application Ser. No. 61/987,396, filed May 1, 2014, and U.S. provisional application Ser. No. 62/151,909 filed Apr. 23, 2015, the disclosures of which are herein incorporated by reference.

INTRODUCTION

Nucleic acid polymer chemistry has played a role in many developing technologies in the pharmaceutical, diagnostic, and analytical fields, and more particularly in the subfields of antisense and anti-gene therapeutics, combinatorial chemistry, branched DNA signal amplification, and array-based DNA diagnostics and analysis. Some of this polymer chemistry has been directed to improving the binding strength, specificity, and nuclease resistance of natural nucleic acid polymers, such as DNA. Peptide nucleic acid (PNAs), phosphorothioate, methylphosphonate and phosphoramidate internucleoside linkages are examples of some polymer chemistries that have been applied to oligonucleotides to provide for one or more desirable properties such as nuclease resistance, cellular uptake and solubility.

Oligonucleotide N3'→P5' phosphoramidates can form stable duplexes with complementary DNA and RNA strands, as well as stable triplexes with DNA duplexes, and are resistant to nucleases. Oligonucleotide N3'→P5' thiophosphoramidates have found use as potent antisense agents both in vitro and in vivo. For example, oligonucleotide containing compounds that inhibit telomerase activity can be used to treat telomerase-mediated disorders, such as cancer, since cancer cells express telomerase activity and normal human somatic cells do not possess telomerase activity at biologically relevant levels. As such, methods of preparing and isolating such oligonucleotides are of interest.

SUMMARY

The present disclosure provides a solid phase method of making oligonucleotides via sequential coupling cycles including at least one coupling of a dinucleotide dimer subunit to a free 3'-terminal group (e.g., a 3'-hydroxyl or 3'-amino group) of a growing chain. The subject methods include making oligonucleotides where at least two of the nucleoside subunits are joined by a N3'→P5' phosphoramidate inter-subunit linkage. The method may include the steps of (a) deprotecting the protected 3' amino group of a terminal nucleoside attached to a solid phase support, said deprotecting forming a free 3' amino group; (b) contacting the free 3' amino group with a 3'-protected amino-dinucleotide-5'-phosphoramidite dimer in the presence of a nucleophilic catalyst to form an internucleoside N3'→P5' phosphoramidite linkage; and (c) oxidizing the linkage. In some cases, oxidizing the linkage include sulfurizing to produce an internucleoside N3'→P5' thiophosphoramidate linkage.

Aspects of the present disclosure include oligonucleotide compositions produced by the subject methods that include a reduced amount of one or more (N−x) oligonucleotide products. In some cases, the reduced amount is less than (1.9×N) parts to 100 by weight of one or more (N−x) products relative to N product. Oligonucleotides prepared according to the subject methods include an oligonucleotide having a sequence of N nucleoside subunits complementary to the RNA component of human telomerase, wherein at least two of the nucleoside subunits are joined by a N3'→P5' thiophosphoramidate inter-subunit linkage. Also provided are pharmaceutical compositions including the subject oligonucleotide compositions.

BRIEF DESCRIPTION OF THE DRAWINGS

FIGS. 2A and 2B show an HPLC chromatogram (A) and $^{31}$P NMR spectra (B) for a AA dimer thiophosphoramidate (compound 7a, Scheme 1).

FIGS. 3A and 3B show an HPLC chromatogram (A) and $^{31}$P NMR spectra (B) for a GG dimer thiophosphoramidate (compound 7c, Scheme 1).

FIGS. 5A and 5B show an HPLC chromatogram (A) and $^{31}$P NMR spectra (B) for a GA dimer thiophosphoramidate (compound 7b, Scheme 1).

FIGS. 6A and 6B show LCMS traces for dimer amidates TA, AA, GA, GT and GG.

FIG. 7 shows an HPLC chromatogram of the product of a 140 µmole scale synthesis of imetelstat using a monomer coupling strategy.

DEFINITIONS

Figure 1A:
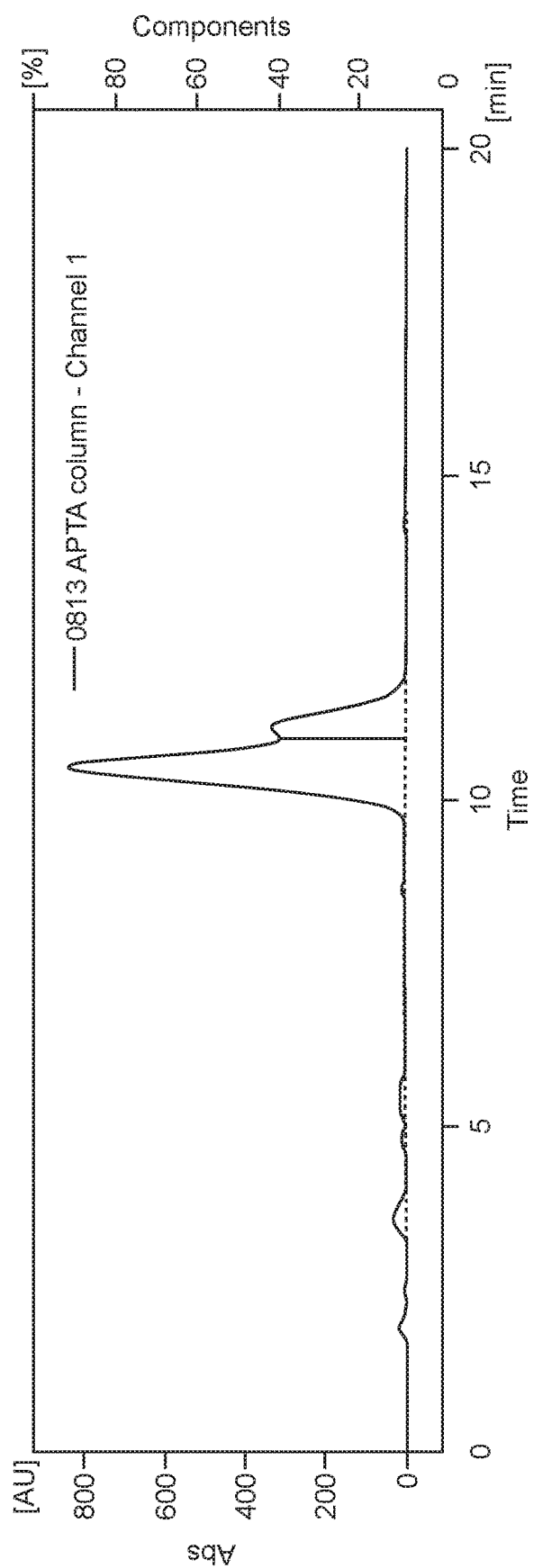
FIGS. 1A and 1B show an HPLC chromatogram (A) and $^{31}$P NMR spectra (B) for a TA dimer thiophosphoramidate (compound 7e, Scheme 1).

The following terms have the following meanings unless otherwise indicated. Any undefined terms have their art recognized meanings.

As used herein, the terms polynucleotide and oligonucleotide are used interchangeably. Whenever an oligonucleotide is represented by a sequence of letters, such as "ATGUCCTG," it is understood that the nucleotides are in 5'→3' order from left to right and that "A" denotes deoxyadenosine, "C" denotes deoxycytidine, "G" denotes deoxyguanosine, "T" denotes thymidine, and "U" denotes deoxyuridine, unless otherwise noted.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described generally by Scheit, Nucleotide Analogs (John Wiley, New York, 1980). Such analogs include synthetic nucleosides designed to enhance binding properties, e.g. stability, specificity, or the like, such as disclosed by Uhlmann and Peyman (Chemical Reviews, 90:543-584, 1990). In some embodiments, a nucleoside or nucleoside analog includes a 3'-hydroxyl group or a 3'-amino group.

The terms "base" and "nucleobase" are used interchangeably and defined herein to include (i) conventional DNA and RNA bases (uracil, thymine, adenine, guanine, and cytosine), and (ii) modified bases or base analogs (e.g., 5-methyl-cytosine, 5-bromouracil, or inosine). A base analog is a chemical whose molecular structure mimics that of a conventional DNA or RNA base.

As used herein, "pyrimidine" means the pyrimidines occurring in natural nucleosides, including cytosine, thymine, and uracil, and common analogs thereof, such as those containing oxy, methyl, propynyl, methoxy, hydroxyl, amino, thio, halo, and like, substituents. The term as used herein further includes pyrimidines with common protection groups attached, such as $N^4$-benzoylcytosine. Further common pyrimidine protection groups are disclosed by Beaucage and Iyer Tetrahedron 48: 2223-2311 (1992).

As used herein, "purine" means the purines occurring in natural nucleosides, including adenine, guanine, and hypoxanthine, and common analogs thereof, such as those containing oxy, methyl, propynyl, methoxy, hydroxyl, amino, thio, halo, and like, substituents. The term as used herein further includes purines with common protection groups attached, such as $N^2$-benzoylguanine, $N^2$-isobutyrylguanine, $N^6$-benzoyladenine, and the like. Further common purine protection groups are disclosed by Beaucage and Iyer Tetrahedron 48: 2223-2311 (1992). As used herein, the term "-protected-" as a component of a chemical name refers to art-recognized protection groups for a particular moiety of a compound, e.g. "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like; and a protected nucleobase in reference to a nucleobase including a heteroatom protected with a group such as a dimethylaminoformamidine (DMF), benzoyl (Bz), isobutyryl, and the like. Art-recognized protection groups include those described in the following references: Gait, editor, Oligonucleotide Synthesis: A Practical Approach (IRL Press, Oxford, 1984); Amarnath and Broom, Chemical Reviews, 77:183-217, 1977; Pon et al., Biotechniques, 6:768-775, 1988; Ohtsuka et al, Nicleic Acids Research, 10:6553-6570, 1982; Eckstein, editor, Oligonucleotides. and Analogues: A Practical Approach (IRL Press, Oxford, 1991), Greene and Wuts, Protective Groups in Organic Synthesis, Second Edition, (John Wiley & Sons, New York, 1991), Narang, editor, Synthesis and Applications of DNA and RNA (Academic Press, New York, 1987), Beaucage and Iyer Tetrahedron 48: 2223-2311 (1992), and like references.

As used herein, "oligonucleotide N3'→P5' phosphoramidate" means an oligomer, usually linear, of nucleoside subunits linked by at least one N3'→P5' phosphoramidate linkage. In general terms, the nucleoside subunits comprise nucleosides or nucleoside analogs, but may also comprise more general moieties having compatible chemistry, such as abasic sugars and other hydrocarbon moieties, such as described in the following references: Newton et al., Nucleic Acids Research, 21: 1155-1162 (1993); Griffin et al, J. Am. Chem. Soc., 114: 7976-7982 (1992); Jaschke et al, Tetrahedron Letters, 34: 301-304 (1992); Ma et al., International application PCT/CA92/00423; Zon et al., International application PCT/US90/06630; Durand et al., Nucleic Acids Research, 18: 6353-6359 (1990); Salunkhe et al., J. Am. Chem. Soc., 114: 8768-8772 (1992); and the like. In some instances, the term means an oligonucleotide wherein all internucleosidic linkages are replaced by N3'→P5' phosphoramidate linkages, i.e. the term comprehends partially as well as fully "amidated" oligomers. In some instances, it means an oligonucleotide wherein all the internucleosidic linkages are replaced by N3'→P5' phosphoramidate linkages and wherein the nucleoside subunits are the natural nucleosides or analogs thereof. A subject oligonucleotide N3'→P5' phosphoramidate in which every linkage is an N3'→P5' phosphoramidate linkage ("fully amidated") may be imbedded in or attached to other oligonucleotides or polynucleotides to form a larger oligomer which is "partially amidated." A subject oligonucleotide N3'→P5' phosphoramidate may include any convenient 3' and/or 5' terminal groups. In some embodiments, the oligonucleotide N3'→P5' phosphoramidate includes a 3'-hydroxyl terminal group or a 3'-amino terminal group.

As used herein, the terms "phosphate" and "phosphate group" are meant to encompass a thiophosphate group and an oxophosphate group.

As used herein, the term "phosphoramidite amino group" refers to the amino group, $-NR^4R^5$, attached to the phosphorus atom of a phosphoramidite group, and the term "phosphoramidite nitrogen" refers to the nitrogen atom of the phosphoramidite amino group.

"Alkyl" refers to monovalent saturated aliphatic hydrocarbyl groups having from 1 to 10 carbon atoms and such as 1 to 6 carbon atoms (e.g., "an alkyl of 1 to 6 carbons atoms"), or 1 to 5 (e.g., "an alkyl of 1 to 5 carbons atoms"), or 1 to 4 (e.g., "an alkyl of 1 to 4 carbons atoms"), or 1 to 3 carbon atoms (e.g., "an alkyl of 1 to 3 carbons atoms"). This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2$CH—), n-butyl ($CH_3CH_2CH_2CH_2$—), isobutyl (($CH_3)_2$CHCH$_2$—), sec-butyl (($CH_3$)($CH_3CH_2$)CH—), t-butyl (($CH_3)_3$C—), n-pentyl ($CH_3CH_2CH_2CH_2CH_2$—), and neo-pentyl (($CH_3)_3CCH_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. In some instances, a "substituted alkyl" refers to an alkyl group as defined herein having from 1 to 5 substituents selected from the group consisting of alkoxy, cycloalkyl, cycloalkenyl, acyl, acylamino, acyloxy, amino, aminoacyl, aminoacyloxy, oxyaminoacyl, azido, cyano, halogen, hydroxyl, carboxyl, carboxylalkyl, thiol, thioalkoxy, aryl, aryloxy, heteroaryl, heteroaryloxy, heterocyclyl, heterocyclooxy, sulfonamido, and —NR$^a$R$^b$, wherein R$^a$ and R$^b$ may be the same or different and are chosen from hydrogen, alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C (O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. In such cases, an aryl group that is substituted with from 1 to 5 substituents (e.g., as described herein) is referred to as a "substituted aryl".

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O— alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O— substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl. In such cases, a heteroaryl group that is substituted with from 1 to 5 substituents (e.g., as described herein) is referred to as a "substituted heteroaryl".

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$ (M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$, and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$_{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$R$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment.

For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, and the like; and when the molecule contains a basic functionality, salts of organic or inorganic acids, such as hydrochloride, and the like. Pharmaceutically acceptable salts of interest include, but are not limited to, aluminium, ammonium, arginine, barium, benzathine, calcium, cholinate, ethylenediamine, lysine, lithium, magnesium, meglumine, procaine, potassium, sodium, tromethamine, N-methylglucamine, N,N'-dibenzylethylene-diamine, chloroprocaine, diethanolamine, ethanolamine, piperazine, zinc, diisopropylamine, diisopropylethylamine, triethylamine and triethanolamine salts.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt. Salts of interest include, but are not limited to, aluminium, ammonium, arginine, barium, benzathine, calcium, cesium, cholinate, ethylenediamine, lithium, magnesium, meglumine, procaine, N-methylglucamine, piperazine, potassium, sodium, tromethamine, zinc, N,N'-dibenzylethylene-diamine, chloroprocaine, diethanolamine, ethanolamine, piperazine, diisopropylamine, diisopropylethylamine, triethylamine and triethanolamine salts. It is understood that for any of the oligonucleotide structures depicted herein that include a backbone of internucleoside linkages, such oligonucleotides may also include any convenient salt forms. In some embodiments, acidic forms of the internucleoside linkages are depicted for simplicity. In some instances, the salt of the subject compound is a monovalent cation salt. In certain instances, the salt of the subject compound is a divalent cation salt. In some instances, the salt of the subject compound is a trivalent cation salt. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, —NH—P(=S)(OH)—O— and —NH—P(=O)(SH)—O—, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric arrangements of the groups described herein are possible. For example, it is understood that an oligonucleotide described by the following structure:

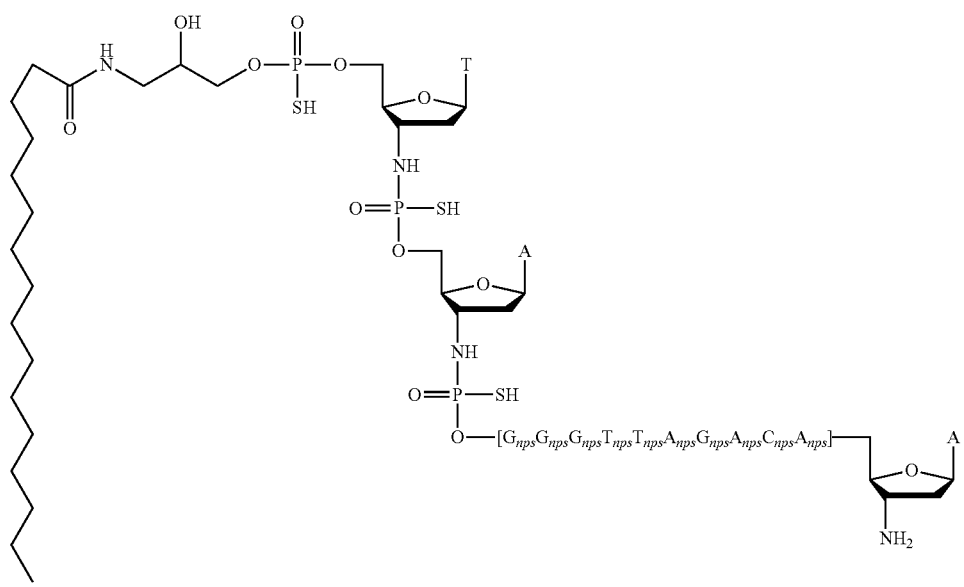

also encompasses the following structure showing one possible alternate tautomeric arrangement of linkage groups:

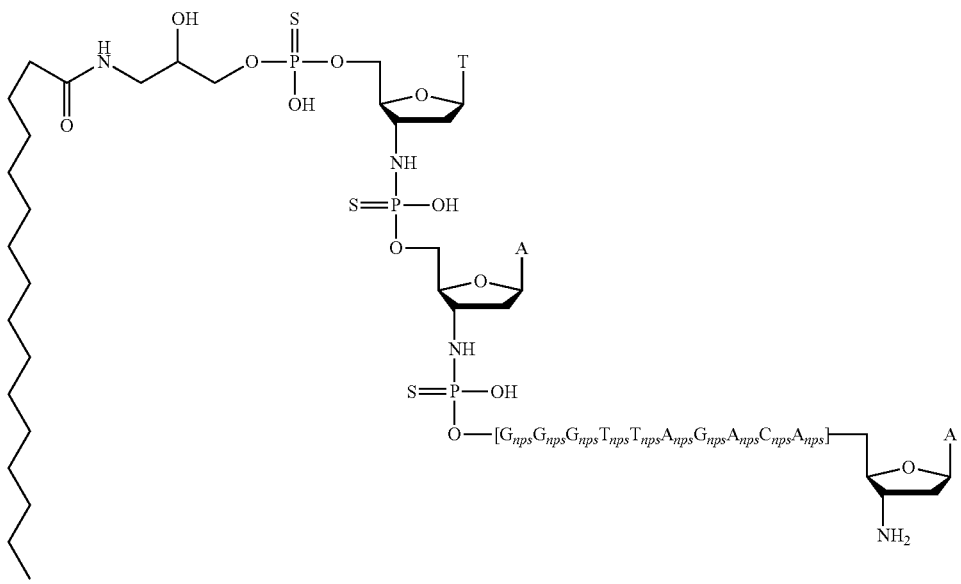

where "nps" represents a thiophosphoramidate linkage (—NH—P(=O)(SH)—O— or —NH—P(=S)(OH)—O—) connecting the 3'-carbon of one nucleoside to the 5'-carbon of the adjacent nucleoside. It is understood that all tautomeric forms of a subject compound are encompassed by a structure where one possible tautomeric arrangement of the groups of the compound is described, even if not specifically indicated. Any convenient tautomeric arrangement of the groups of the subject compounds may be utilized in describing the compounds.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound. It is understood that the term "or a salt thereof" is intended to include all permutations of salts. It is understood that the term "or a pharmaceutically acceptable salt thereof" is intended to include all permutations of salts. It is understood that the term "or a solvate thereof" is intended to include all permutations of solvates. It is understood that the term "or a stereoisomer thereof" is intended to include all permutations of stereoisomers. It is understood that the term "or a tautomer thereof" is intended to include all permutations of tautomers. Thus for example it follows that it is intended to include a solvate of a pharmaceutically acceptable salt of a tautomer of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, methods and materials of interest are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides a solid phase method of preparing oligonucleotides via sequential coupling cycles including the coupling of a dinucleotide dimer to a free 3' terminal group (e.g., a 3'-hydroxyl or 3'-amino group) of a growing chain. In general terms the synthesis proceeds from the 5'-terminal to the 3'-terminal of a target oligonucleotide sequence and includes at least one coupling of a dinucleotide dimer. The dimer may be coupled to the free 3' terminal group of a growing chain via any convenient chemistry. In some cases, the dimer is a 3'-protected-dinucleotide-5'-phosphoramidite dimer, where the dinucleotide may include any convenient inter-nucleoside linkage. The oligonucleotide may include one or more phosphoramidate inter-subunit linkages (e.g., an oxo-phosphoramidate or thiophosphoramidate linkage).

In some embodiments, the oligonucleotide includes a sequence of nucleoside subunits containing at least one subunit defined by the formula:

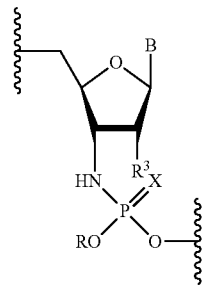

where B is a purine, a protected purine, a pyrimidine or a protected pyrimidine, or an analog thereof; X is O or S; R is selected from the group consisting of hydrogen, an alkyl, a substituted alkyl, an aryl, a substituted aryl, a phosphate protecting group; and $R^3$ is selected from the group consisting of hydrogen, O—$R^2$, and halogen, wherein $R^2$ is H, an alkyl, a substituted alkyl (e.g., —$(CH_2)_n W(CH_2)_m H$, where n is between 1-10, m is between 0-10 and W is O, S, or NH) or a hydroxyl protecting group. It is understood that some of the oligonucleotides including a subunit described by the formula above may also exist in a salt form. Such forms in so far as they may exist, are intended to be included within the scope of the present disclosure.

The subject methods provide for a reduced number of coupling cycles relative to methods involving only nucleoside monomer subunit couplings and provide for reduced amounts of non-target oligonucleotide products of the synthesis. The retrosynthetic strategy utilized for preparing a target oligonucleotide sequence may be selected depending on a variety of factors, such as the length and sequence of the target oligonucleotide so as to minimize the amounts of particular non-target oligonucleotide products of the synthesis.

In some embodiments, the subject methods provide for the preparation of compositions that have a reduced amount of one or more (N–x) products relative to a target oligonucleotide of interest.

In certain embodiments, any of the compositions described herein that have a reduced amount of one or more (N–x) products relative to a target oligonucleotide of interest are unpurified.

As used herein, the term "(N–x) product" (where x is an integer from 1 to N–1 and N is the number of nucleoside residues in a target oligonucleotide), refers to a non-target oligonucleotide produced during the subject methods of preparation that lacks x nucleoside residues by comparison with the sequence of a target oligonucleotide of N residues in length. The target oligonucleotide is the product which the subject method of preparation is designed to produce. As such, a (N–1) product is a non-target oligonucleotide that lacks any one nucleoside residue out of the sequence of the target oligonucleotide. As such, in some cases, the term "(N−1) product" refers to a variety of non-target oligonucleotide products, each of which lack one nucleoside residue by comparison to the sequence of the target oligonucleotide. Similarly, the term "(N−x) product" refers to a variety of non-target oligonucleotide products, each of which lack x nucleoside residues by comparison to the sequence of the target oligonucleotide. For example, a (N−2) product is a non-target oligonucleotide that lacks any two nucleoside residues out of the sequence of the target oligonucleotide. In some cases the x residues are contiguous to each other relative to the target oligo nucleotide sequence. In other cases, the x residues are discontiguous to each other relative to the target oligo nucleotide sequence. The x nucleoside residues may be lacking from any location of the target sequence and may be produced from unreacted 3'-terminal groups during a coupling cycle. The (N−x) products of the subject methods may include one or more further modifications that derive from the subject methods of synthesis, e.g., a partial deprotection modification, loss of a nucleobase (e.g., depurination), capping of a terminal group, derivatization via a synthesis reagent (e.g., phenylacetylation by a sulfurization reagent), and the like. A variety of modified oligonucleotides are possible depending on the chemistry of oligonucleotide synthesis and reagent utilized. Unless indicated otherwise, all such modifications are meant to be encompassed by the term (N−x) product.

In some embodiments, the subject methods result in the reduction of one or more non-target products of oligonucleotide synthesis selected from a partially protected product or a partially protected (N−x) product, e.g., an oligonucleotide product including one or more nucleobase protecting groups. In the subject oligonucleotide compositions, the target oligonucleotide sequence may be more readily isolated or purified from other oligonucleotide-containing products of the method, e.g., (N−x) products and products lacking a nucleobase.

Embodiments of the subject methods and compositions are described in more detail in the sections below.

Methods of Making Oligonucleotides

The present disclosure provides a method of preparing an oligonucleotide. The subject methods may include at least one coupling of a dinucelotide dimer to the free 3' terminal group of a growing oligonucleotide chain. Any convenient oligonucleotide synthesis methods and chemistries may be utilized in the subject methods of preparation. Oligonucleotide synthesis chemistries and methods of interest that may be adapted for use in the subject methods include, but are not limited to, phosphoramidite, HI-phosphonate, phosphodiester, phosphotriester, phosphite triester, and those described by Fearon et al. in U.S. Pat. No. 5,824,793, the disclosure of which is herein incorporated by reference in its entirety. The oligonucleotide components of the invention compounds may be synthesized by adapting conventional protocols for the type of chemistry selected. Methods of interest for the synthesis of oligonucleotides having N3'→P5' phosphoramidate chemistries include, but are not limited to, those methods described in McCurdy et al., (1997) Tetrahedron Letters, 38:207-210 and Pongracz & Gryaznov, (1999) Tetrahedron Letters, 49:7661-7664.

An oligonucleotide of interest may be prepared using the subject methods via sequential couplings starting from the 5'-terminal and proceeding to the 3'-terminal of the target oligonucleotide sequence. The 5'-terminal nucleoside subunit may be attached to any convenient solid support via an optional linking group or 5'-terminal group. Then, subunit couplings to the growing oligonucleotide chain may be achieved using either dimer phosphoramidites or monomer phosphoramidites. Alternatively, the 5'-terminal dinucleotide subunit may be attached to any convenient solid support via an optional linking group or 5'-terminal group. Once the first subunit (e.g., monomer or dimer subunit) is attached to the solid support, the subunit may be deprotected to produce a free, immobilized 3'-terminal group. In some cases, the method includes coupling a support bound 3'-terminal group with a 3'-protected-dinucleotide-5'-phosphoramidite dimer. In certain embodiments, the 3'-terminal group is a 3'-hydroxyl group. In certain embodiments, the 3'-terminal group is a 3'-amino group.

In some instances, the method includes the steps of: (a) deprotecting the protected 3' amino group of a terminal nucleoside attached to a solid phase support, said deprotecting forming a free 3' amino group; (b) contacting the free 3' amino group with a 3'-protected amino-dinucleotide thiophosphoramidate or phosphoramidite-5'-phosphoramidite dimer in the presence of a nucleophilic catalyst to form an internucleoside N3'→P5' phosphoramidite linkage; and (c) oxidizing the linkage.

The target oligonucleotide sequence may be synthesized using a retrosynthetic strategy that includes sequentially coupling of both dimer and monomer subunits to the 3' terminal group of the growing oligonucleotide chain. As such, in some embodiments, the method further includes the steps of: (a) deprotecting the protected 3' amino group of a terminal nucleoside attached to a solid phase support, said deprotecting forming a free 3' amino group; (b) contacting the free 3' amino group with a 3'-protected aminonucleoside-5'-phosphoramidite monomer in the presence of a nucleophilic catalyst to form an internucleoside N3'→P5' phosphoramidite linkage; and (c) oxidizing the linkage to produce a N3'→P5' phosphoramidate linkage.

As used herein, the term "N3'→P5' phosphoramidite linkage" refers to the phosphorus (III) intermediate of the N3'→P5' phosphoramidate linkage. In general terms, an N3'→P5' phosphoramidate linkage is formed by oxidizing an N3'→P5' phosphoramidite linkage to a phosphorus (V) product (e.g., a N3'→P5' phosphoramidate linkage that may include an oxo (P=O) or a thio (P=S) group). In some cases, the oxidizing step may be described as sulfurizing the N3'→P5' phosphoramidite linkage to produce a N3'→P5' thiophosphoramidate linkage.

As used herein, "N3'→P5' phosphoramidate", "P5'→N3' phosphoramidate" and "phosphoramidate" refer to an intemucleosidic subunit linkage described by the formula:

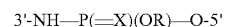

3'-NH—P(=X)(OR)—O-5' or a tautomer thereof, wherein the 3' and 5' refer to the carbon atoms of the sugar moieties of consecutive nucleosides which are connected by way of the linkage, and wherein R is hydrogen, an alkyl, a substituted alkyl, an aryl, a substituted aryl, or a phosphate protecting group, and X is a chalcogen, such as oxygen or sulfur. It is understood that, when R is hydrogen, an alkyl, a substituted alkyl, an aryl, a substituted aryl, or a phosphate protecting group, some of the internucleosidic subunit linkages described by the formula above may also exist in a salt form. Such forms in so far as they may exist, are intended to be included within the scope of the present disclosure. In some cases, when X is sulfur, the phosphoramidate may be referred to as a thiophosphoramidate. In some cases, when X is oxygen, the "phosphoramidate" may be referred to as an "oxophosphoramidate". In some cases, when R is a phosphate protecting group it may be an alkyl, an alkenyl, an aryl, an aralkyl, a cycloalkyl, or a substituted version thereof. In some cases, R is a phosphate protecting group containing 10 or less carbon atoms. In certain instances, when R is a phosphate protecting group it is an alkyl having from 1 to 6 carbon atoms; an electron-withdrawing β-substituted ethyl (e.g., β-trihalomethyl-, β-cyano-, β-sulfo-, or β-nitro-substituted ethyl); an electron-withdrawing substituted phenyl (e.g., halo-, sulfo-, cyano-, or nitro-, substituted phenyl); or an electron-withdrawing substituted phenylethyl. In some embodiments, when R is a phosphate protecting group it is methyl, β-cyanoethyl, or 4-nitrophenylethyl. In certain embodiments, R is hydrogen, methyl, or β-cyanoethyl. Electron-withdrawing substituents of interest include, but are not limited to, halo, cyano, nitro, sulfo, or mono-, di-, or trihalomethyl, and the like. Halogen atom substituents are usually fluoro, chloro, bromo, or iodo; and in some instances, they are fluoro or chloro. "Electron-withdrawing" denotes the tendency of a substituent to attract valence electrons of the molecule of which it is a part, i.e. it is electronegative, e.g. March, Advanced Organic Chemistry, pgs. 16-18 (John Wiley, New York, 1985). Guidance for selecting a phosphate protecting group is provided in Beaucage and Iyer, Tetrahedron 48: 2223-2311 (1992). For convenience, nucleotide phosphoramidates are sometimes indicated herein by a subscripted "np" or "pn" for N3'→P5' phosphoramidates and P3'→N5' phosphoramidates, respectively. Thus, "$U_{np}U$" is a dinucleotide in which a 3'-aminouridine and a uridine are linked by an N3'→P5' phosphoramidate linkage. When the linkage is an oxo-phosphoramidate, the nucleotide oxo-phosphoramidate is sometimes indicated herein by a subscripted "npo" or "opn" for N3'→P5' phosphoramidates and P3'→N5' phosphoramidates, respectively. Similarly, nucleotide thiophosphoramidates are sometimes indicated herein by a subscripted "nps" or "spn" for N3'→P5' thiophosphoramidates and P3'→N5' thiophosphoramidates, respectively. Similarly, 2'-fluoro substituents are indicated by a superscripted "f". Thus, "$U_{f,np}U$" is a dinucleotide in which the 5'-most 3'-amino-2'-fluorouridine is linked to a uridine by an N3'→P5' phosphoramidate linkage. A single leading subscripted "p" indicates a 5' monophosphate, and a single trailing subscripted "n" indicates a 3'-amino group.

In some instances, the internucleoside subunit linkage is described by the formula:

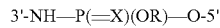

3'-NH—P(=X)(OR)—O-5' or a tautomer thereof, wherein the 3' and 5' refer to the carbon atoms of the sugar moieties of consecutive nucleosides which are connected by way of the linkage, and where R is hydrogen and X is oxygen or sulfur. It is understood that for any of the oligonucleotides described herein that include such an internucleoside linkage, such oligonucleotides may also include any convenient salt forms of the linkage. As such, the internucleoside linkage may be in a salt form that includes any convenient counterion.

Any convenient protecting group strategies may be utilized in the subject methods to protect the base, phosphoramidite, phosphoramidate, 5', 2' and/or 3' groups. Protecting groups of interest include, but are not limited to, those protecting groups described by Ohkubo et al., *Org. Lett.*, 2010, 12 (11), pp 2496-2499; and Beaucage and Iyer, Tetrahedron 48: 2223-2311 (1992).

As used herein, the term "phosphate protecting group" refers to a protecting group that may be attached to a phosphorus-containing intersubunit linkage of an oligonucleotide. When present, a phosphate protecting group may prevent (i.e., block) reaction of the phosphorus-containing linkage at the location where the phosphate protecting group is attached. Any convenient phosphorus-containing intersubunit linkages (e.g., P(III) and P(V) linkages) may be protected by the subject phosphate protecting groups, including, but not limited to, phosphoramidite, oxophosphoramidate, thiophosphoramidate, phosphate ester, thiophosphate ester, phosphodiester linkages and the like. The phosphate protecting group may be attached to an available oxygen atom of the phosphorus-containing intersubunit linkage. Any convenient protecting groups may be utilized as a phosphate protecting group. Phosphate protecting groups of interest include, but are not limited to, an alkyl, an alkenyl, an aryl, an aralkyl, a cycloalkyl, or a substituted version thereof, such as an alkyl having from 1 to 6 carbon atoms, such as an electron-withdrawing β-substituted ethyl (e.g., β-trihalomethyl-, β-cyano-, β-sulfo-, or p-nitro-substituted ethyl); an electron-withdrawing substituted phenyl (e.g., halo-, sulfo-, cyano-, or nitro-, substituted phenyl); or an electron-withdrawing substituted phenylethyl, methyl, β-cyanoethyl, or 4-nitrophenylethyl. In certain embodiments, phosphate protecting group is methyl, or β-cyanoethyl. Electron-withdrawing substituents of interest include, but are not limited to, halo (e.g., chloro or fluoro), cyano, nitro, sulfo, or mono-, di-, or trihalomethyl, and the like.

The 3'-terminal group of the growing oligonucleotide chain may include a 3'-hydroxyl, a 3'-amino group or a protected version thereof. Any convenient hydroxyl and/or amino protecting groups may be utilized at the 3'-terminal group during oligonucleotide synthesis. In some embodiments, the 3'terminal group is a protected 3'-amino group and the method includes deprotecting or removing the protecting group to produce a free 3'amino group.

As used herein, the term "free amino group" in reference to the monomers and dimers means an amino group available for reacting with the phosphoramidite group of an incoming monomer or dimer. In some embodiments, a free amino group is a primary amine. After the deprotection (e.g., detritylation) step, the amino group may be in the form of a salt (e.g., the salt of a conjugate base of the acid used for detritylation). This salt optionally may be neutralized with a basic solution such as 2% triethylamine or pyridine in acetonitrile after the detritylation step.

In some embodiments, the 3'-terminal group is a protected 3'-hydroxyl group and the method includes deprotecting or removing the protecting group to produce a free 3'-hydroxyl group. In some embodiments, the 3'-terminal group is a protected 3'-amino group and the method includes deprotecting or removing the protecting group to produce a free 3'-amino group. The protected 3'-amino or 3'-hydroxyl group may be protected with a trityl protecting group. In certain embodiments, the trityl protecting group is triphenylmethyl (Tr, Ph$_3$C—). In certain embodiments, the trityl protecting group is 4,4'-dimethoxytrityl (DMT).

Deprotection of the 3'-terminal amino or hydroxyl group may be achieved using any convenient methods. Methods of interest include, but are not limited to, those methods described by Beaucage and Iyer, Tetrahedron 48: 2223-2311 (1992). In some cases, deprotection of the protected 3' amino group of a terminal nucleoside includes detritylation to produce a free 3'terminal group, e.g., acid-catalyzed detritylation.

In general, the dimer or monomer subunit phosphoramidites include a protected 3'-hydroxyl or 3'-amino group that is the same as the 3'terminal group of the terminal nucleoside attached to the solid support. 3'-Protection of the incoming subunit phosphoramidites prevents undesirable polymerization of the chain.

Any convenient solid phase supports may be used in the subject methods. Solid supports of interest include, but are not limited to, microparticles made of controlled pore glass (CPG), highly cross-linked polystyrene (e.g., NittoPhase HL 400 or GE Primer 350), acrylic copolymers, cellulose, nylon, dextran, latex, polyacrolein, and the like, such as those disclosed in the following exemplary references: Meth. Enzymol., Section A, pages 11-147, vol. 44 (Academic Press, New York, 1976); U.S. Pat. Nos. 4,678,814; 4,413,070; and 4,046,720; and Pon, Chapter 19, in Agrawal, editor, Methods in Molecular Biology, Vol. 20, (Humana Press, Totowa, N.J., 1993). Further supports of interest include polystyrene beads; polystyrene grafted with polyethylene glycol (e.g., TentaGel™, Rapp Polymere, Tubingen Germany); and the like. Selection of the support characteristics, such as material, porosity, size, shape, and the like, and the type of linking moiety employed depends on a variety of factors, such as protection groups employed, length of final product, quantity of final product, and the like. Exemplary linking moieties are disclosed in Pon et al, Biotechniques, 6:768-775 (1988); Webb, U.S. Pat. No. 4,659,774; Barany et al, International patent application PCT/US91/06103; Brown et al, J. Chem. Soc. Commun., 1989: 891-893; Damha et al, Nucleic Acids Research, 18: 3813-3821 (1990); Beattie et al, Clinical Chemistry, 39: 719-722 (1993); Maskos and Southern, Nucleic Acids Research, 20: 1679-1684 (1992); and the like.

In some embodiments, the solid supports that find use in the subject methods include CPG and polystyrene grafted with polyethylene glycol and possessing a terminal amino group (e.g., TentaGel-NH$_2$™, Rapp Polymere, Tubingen Germany). The aminopropyl group may be used as a spacer between CPG and the nucleoside linkage. In some cases, the linkage to the 5'-hydroxyl of the first nucleoside is a succinyl group which provides a base-labile ester linkage that may be cleaved after synthesis with aqueous ammonia.

Following deprotection, the support-bound nucleoside is capable of reacting with a dimer or monomer subunit phosphoramidite to form an internucleoside linkage. It is understood that the support-bound nucleoside may refer to a single residue attached to a solid support or may refer to the terminal residue of an oligonucleotide chain that is attached to the support.

Any convenient coupling chemistry, coupling reagents and methods may be utilized in the subject methods. Considerable guidance in making selections concerning coupling conditions, protecting groups, solid phase supports, linking groups, deprotection reagents, reagents to cleave products from solid phase supports, purification of product, and the like, in the context of the subject methods can be found in literature, e.g. Gait, editor, Oligonucleotide Synthesis: A Practical Approach (IRL Press, Oxford, 1984); Amarnath and Broom, Chemical Reviews, Vol. 77, pgs. 183-217 (1977); Pon et al, Biotechniques, Vol. 6, pgs. 768-775 (1988); Ohtsuka et al, Nucleic Acids Research, Vol. 10, pgs. 6553-6570 (1982); Eckstein, editor Oligonucleotides. and Analogues: A Practical Approach (IRL Press, Oxford, 1991), Greene and Wuts "Protective Groups in Organic Synthesis", Third edition, Wiley, New York 1999, Narang, editor, Synthesis and Applications of DNA and RNA (Academic Press, New York, 1987), Beaucage and Iyer, Tetrahedron 48: 2223-2311 (1992), and like references.

The coupling step of the subject methods may be carried out in the temperature range of −20 to 200 degrees Centigrade. In some instances, the reaction is carried out at ambient temperature (about 15-30 degrees Centigrade). The reaction may be performed by adding a solution of the phosphoramidite dimer or monomer and a solution of an activator (or a solution containing the phosphoramidite dimer or monomer and the activator) to the reaction vessel containing the free amino group of an (oligo)nucleotide covalently attached to a solid support. Generally, activators of interest include nucleophilic catalysts that displace the more stable phosphoramidite amino group to form a highly reactive (and less stable) intermediate which, in turn, reacts with the free 3' amino group of a solid supported oligonucleotide N3'→P5' phosphoramidate. The mixture is then mixed by such methods as mechanical vortexing, sparging with an inert gas, etc. Alternately, the solution(s) of dimer or monomer and activator can be made to flow through a reaction vessel (or column) containing the solid supported (oligo)nucleotide with a free 3'-terminal group. The monomer and the activator either can be premixed, mixed in the valve-block of a suitable synthesizer, mixed in a pre-activation vessel and pre-equilibrated if desired, or they can be added separately to the reaction vessel.

Activators of interest that may be utilized in the subject methods include, but are not limited to, tetrazole, 5-(ethylthio)tetrazole, 5-(4-nitrophenyl)tetrazole, 5-(2-thiophene) tetrazole, triazole, pyridinium chloride, and the like, e.g. activating agents as described by Beaucage and Iyer Tetrahedron 48: 2223-2311 (1992); Berner et al, Nucleic Acids Research, 17: 853-864 (1989); Benson, Chem. Rev. 41: 1-61 (1947). As used herein, the term "tetrazole activator" refers to activators which are tetrazole or derivatives of tetrazole. In some embodiments, the activator is tetrazole. Convenient solvents include, but are not limited to, acetonitrile, tetrahydrofuran, methylene chloride, and the like. Care may be exercised to use dry (free from water) dimer or monomer, activator, and solvent for the coupling step and for the solvent used to wash the solid support immediately before the coupling step.

After coupling, the unreacted 3'-amino groups of the support-bound growing chain of the oligonucleotide may be optionally capped with a convenient capping agent before the next deprotection step (e.g., detritylation step) to render them inert to subsequent coupling steps. This capping step may improve the HPLC profile of the preparation to make purification more facile, and may also improve the overall yield of product. Capping reagents useful in the subject methods include electrophilic reagents such as acetic anhydride and isobutyric anhydride, acid chlorides such as adamantyl carbonyl chloride, pivaoyl chloride, and the like, isothiocyanates, chloroformates, etc. Also useful are phosphoramidites in conjunction with an activator and followed by oxidation, and H-phosphonate salts such as triethylammonium isopropyl-H-phosphonate used in conjunction with an acid chloride such as pivaoyl chloride or adamantyl carbonyl chloride.

In some embodiments, the method includes oxidizing an internucleoside N3'→P5' phosphoramidite linkage. As used herein, the terms "oxidize," "oxidation," "oxidizing", and the like, in reference to a phosphorus-containing internucleosidic linkage means a process or treatment for converting the phosphorus atom of the linkage from a phosphorus (III) form to a phosphorus (V) form. Oxidation of the internucleotide linkages may be performed at any convenient point in the synthesis using any convenient methods. In some embodiments, oxidation is performed in a stepwise manner, e.g., during every coupling cycle. In other embodiments, oxidation of multiple internucleotide linkages is performed at the end of the synthesis. In some instances, oxidizing a N3'→P5' phosphoramidite linkage (e.g., using an iodine/water based oxidizing agent) produces an oxophosphoramidate linkage. In other instances, oxidizing a N3'→P5' phosphoramidite linkage includes sulfurization to produce a thiophosphoramidate linkage. Sulfurization may be performed using any convenient methods. Sulfurization methods of interest include those described by Gryazonov et al., WO2001018015, the disclosure of which is herein incorporated by reference in its entirety. Sulfurizing agents for use in the invention include elemental sulfur, thiuram disulfides such as tetraethyl thiuram disulfide, acyl disulfides such as phenacyldisulfide, phosphinothioyl disulfides such as S-Tetra™, and 1,1-dioxo-3H-1,2-benzodithiol-3-one. In some embodiments, sulfurization may be performed using elemental sulfur (S8). In certain embodiments, sulfurization may be performed using Beaucage reagent, using methods as described by Iyer et al., J. Organic Chemistry 55:4693-4699, 1990.

Oxidizing agents which are useful in the method include iodine, chlorine, bromine, peracids such as m-chlorobenzoic acid, hydroperoxides such as t-butylhydroperoxide, ethyl hydroperoxide, methyl hydroperoxide and the like, ozone, mixed acyl-sulfinic anhydrides such as 3H-2,1-benzoxathiolan-3-one-1-oxide, salts of persulfates such as sodium, ammonium, and tetrabutylammonium persulfate and the like, monoperoxysulfates such as Oxone™, sodium and/or other hypochlorites, peroxides such as diethyl peroxide or bis(trimethylsilyl)peroxide, or hydrogen peroxide or non aqueous hydrogen peroxide equivalents such as urea/hydrogen peroxide complex, etc. Other useful oxidizing agents which may be used to convert phosphorus (III) to phosphorus (V) are described in Beaucage and Iyer Tetrahedron 48: 2223-2311 (1992).

In some cases, the oxidizing or sulfurizing agent may have a tendency to undergo an undesired Arbuzov side reaction in parallel with the desired oxidation (Beaucage and Iyer, cited above). The Arbuzov side reaction can lead to a deprotected phosphoramidate which is unstable to the acidic conditions of subsequent detritylation steps, and result in oligonucleotide fragmentation. In certain embodiments, hydrogen peroxide is used as the oxidizing agent to minimize the Arbuzov side reaction. In certain embodiments, oxidation includes contacting the oligonucleotide with a solution of 1.5% hydrogen peroxide, 3.5% water, 20% pyridine, and 75% THF.

In some embodiments, the method includes the steps of:
(a) deprotecting a protected 3' amino group of a terminal nucleoside attached to a solid phase support, said deprotecting forming a free 3' amino group;
(b) reacting the free 3' amino group with either:
  (i) a 3'-protected amino-dinucleotide phosphoramidate-5'-phosphoramidite dimer; or
  (ii) a 3'-protected aminonucleoside-5'-phosphoramidite monomer; in the presence of a nucleophilic catalyst to form an internucleoside N3'→P5' phosphoramidite linkage;
(c) oxidizing the linkage; and
(d) repeating steps (a) through (c) until the polynucleotide is synthesized, wherein the repeating steps (a) through (c) comprises performing step (b)(i) at least once.

In some embodiments, the repeating steps (a) through (c) comprises performing step (b)(i) twice or more. In certain embodiments, the repeating steps (a) through (c) comprises performing step (b)(i) 3 times or more, such as 4 times or more, 5 times or more, 6 times or more, 7 times or more, 8 times or more, 9 times or more, 10 times or more, 15 times or more, 20 times or more, or even 30 times or more. In certain embodiments, the repeating steps (a) through (c) comprises performing step (b)(i) at every coupling step. In certain embodiments, the repeating steps (a) through (c) comprises performing step (b)(i) at every coupling step except one. In certain embodiments, the repeating steps (a) through (c) comprises performing step (b)(ii) once and only once. In certain embodiments, the repeating steps (a) through (c) comprises performing step (b)(ii) twice and only twice.

As described herein, it is understood that the term phosphoramidate linkage is meant to encompass both oxo-phosphoramidate and thiophosphoramidate linkages (e.g., as depicted in Formula I). In certain embodiments of the method, oxidizing the internucleoside N3'→P5' phosphoramidite linkage produces an oxo-phosphoramidate linkage. In some embodiments of the method, oxidizing the internucleoside N3'→P5' phosphoramidite linkage includes sulfurization to produce a thiophosphoramidate linkage.

In some embodiments of the method, the oligonucleotide is described by Formula (I):

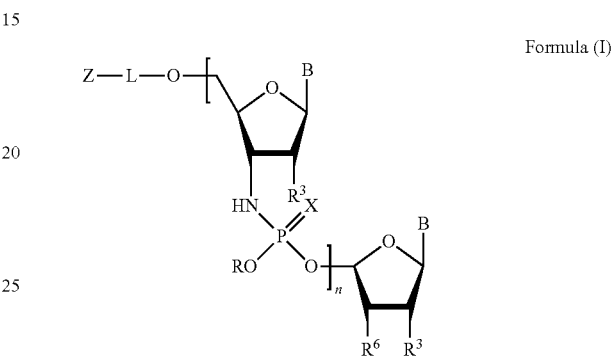

Formula (I)

wherein:
each B is independently a purine, a protected purine, a pyrimidine or a protected pyrimidine, or an analog thereof;
each X is independently oxygen or sulfur;
each $R^3$ is hydrogen, fluoro, hydroxyl, an alkoxy, a substituted alkoxy or a protected hydroxyl;
$R^6$ is amino, hydroxyl, a protected amino, a protected hydroxy, —O-L-Z or —NH-L-Z;
each L is independently an optional linker;
each Z is independently H, a lipid, a support, a carrier, an oligonucleotide, a polymer, a polypeptide, a detectable label, or a tag;
R is hydrogen, an alkyl, a substituted alkyl, an aryl, a substituted aryl or a phosphate protecting group; and
n is an integer of 1 to 1000. When R is hydrogen, an alkyl, a substituted alkyl, an aryl, a substituted aryl or a phosphate protecting group, it is understood that some of the oligonucleotides of Formula (I), may also exist in a salt form. Such forms in so far as they may exist, are intended to be included within the scope of the present disclosure.

In some embodiments of Formula (I), each $R^3$ is hydrogen. In some embodiments of Formula (I), each $R^3$ is fluoro. In some embodiments of Formula (I), each $R^3$ is hydroxyl. In some embodiments of Formula (I), $R^6$ is amino. In certain embodiments of Formula (I), $R^6$ is hydroxyl.

In some embodiments of Formula (I), each R is hydrogen. It is understood that when R is hydrogen, the phosphate linkage may be charged under aqueous conditions, such as physiological conditions. As such, it is understood that oligonucleotides of Formula (I) may also include any convenient salt forms of the linkage. As such, the internucleoside linkage of Formula (I) may be in a salt form that includes any convenient counterion. In some embodiments of Formula (I), each R is an alkyl or a substituted alkyl. In some embodiments of Formula (I), each R is an aryl or a substituted aryl. In some embodiments of Formula (I), each R is a phosphate protecting group.

In some embodiments of Formula (I), Z is H. In some embodiments of Formula (I), Z is a lipid (e.g., as described herein). In certain cases, the lipid is a fatty acid (e.g., as described herein). In some embodiments of Formula (I), Z is a support. In some embodiments of Formula (I), Z is a carrier. In some embodiments of Formula (I), Z is an oligonucleotide. In some embodiments of Formula (I), Z is a polymer. In certain cases, the polymer is a PEG. In some embodiments of Formula (I), Z is a polypeptide. In some embodiments of Formula (I), Z is a detectable label. In some embodiments of Formula (I), Z is a tag.

In some embodiments of Formula (I), L is absent.

In some embodiments, each B is independently selected from A, C, G, T and U or a protected version thereof.

In certain embodiments of Formula (I), n is an integer of between 1 and 500, such as between 1 and 100, between 1 and 75, between 1 and 50, between 1 and 40, between 1 and 30, between 1 and 20, between 1 and 15, between 1 and 10, or between 4 and 10. In certain embodiments, n is an integer of between 1 and 100, such as between 5 and 50, between 10 and 50, between 10 and 40, between 10 and 30, between 10 and 25, between 10 and 20, between 12 and 18, or between 12 and 16. In certain embodiments, n is 4, 5, 6, 7, 8, 9, 10, 11, 12, 13, 14, 15, 16, 17, 18, 19, 20, 21, 22, 23, 24 or 25.

In certain embodiments of the method, the oligonucleotide comprises a sequence of nucleoside subunits complementary to the RNA component of human telomerase, and wherein at least two of the nucleoside subunits are joined by a N3'→P5' phosphoramidate inter-subunit linkage.

In some embodiments of the method, the oligonucleotide includes a sequence of between 3 and 50 nucleoside contiguous subunits complementary to the RNA component of human telomerase, such as between 5 and 40, between 10 and 40, between 10 and 30, between 10 and 25, between 10 and 20, between 12 and 18, or between 12 and 16 nucleoside subunits. In certain embodiments, the oligonucleotide includes a sequence of 10 or more contiguous nucleoside subunits complementary to the RNA component of human telomerase. In certain embodiments, the oligonucleotide includes a sequence of 7 or more contiguous nucleoside subunits, such as 7, 8, 9, 10, 11, 12, 13, 14, 15, 16 or 17 contiguous nucleoside subunits. In certain embodiments, the oligonucleotide includes a sequence of between 11 and 18, such as between 11 and 16 contiguous nucleoside subunits complementary to the RNA component of human telomerase.

In some instances of the method, the N3'→P5' thiophosphoramidate inter-subunit linkage is described by the following structure:

3'-NH—P(S)(OR)—O-5'

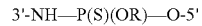

where R is selected from the group consisting of hydrogen, an alkyl, a substituted alkyl, an aryl, a substituted aryl and a phosphate protecting group. It is understood that, when R is selected from the group consisting of hydrogen, an alkyl, a substituted alkyl, an aryl, a substituted aryl and a phosphate protecting group, some of the internucleoside subunit linkages described by the formula above may also exist in a salt form. Such forms in so far as they may exist, are intended to be included within the scope of the present disclosure.

In some instances of the method, the N3'→P5' thiophosphoramidate inter-subunit linkage is described by the following structure:

3'-NH—P(S)(OR)—O-5'

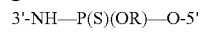

where R is hydrogen. It is understood that for any of the oligonucleotides described herein that includes such an inter-subunit linkage, such oligonucleotides may also include any convenient salt forms of the linkage. As such, the inter-subunit linkage may be in a salt form that includes any convenient counterion.

In some embodiments of the method, the oligonucleotide includes the sequence TAGGGTTAGACAA (SEQ ID NO:3). In certain embodiments, all of the internucleotide inter-subunit linkages of the TAGGGTTAGACAA (SEQ ID NO:3) sequence are N3'→P5' phosphoramidate inter-subunit linkages. In certain instances, all of the N3'→P5' phosphoramidate inter-subunit linkages of the sequence are N3'→P5' thiophosphoramidate inter-subunit linkages (e.g., nps linkages). In certain instances, all of the N3'→P5' phosphoramidate inter-subunit linkages of the sequence are N3'→P5' oxo-phosphoramidate inter-subunit linkages (e.g., np linkages).

In some embodiments of the method, the polynucleotide includes a 3'-amino or a 3'-hydroxyl terminal group. In certain embodiments of the method, the polynucleotide includes a 3'-amino terminal group. In certain embodiments of the method, the polynucleotide includes a 3'-hydroxyl terminal group.

In some embodiments of the method, the oligonucleotide is described by the structure:

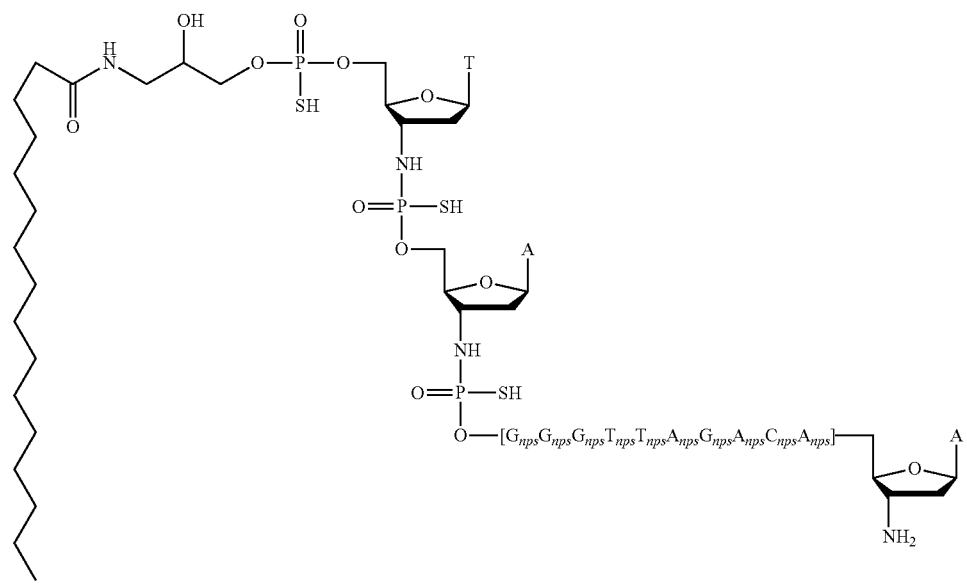

where "nps" represents a thiophosphoramidate linkage (e.g., —NH—P(=O)(SH)—O— or a tautomer thereof), connecting the 3'-carbon of one nucleoside to the 5'-carbon of the adjacent nucleoside.

It is understood that all embodiments referring to an oligonucleotide are also applicable to the salt forms of said oligonucleotide.

In some embodiments of the method, the oligonucleotide is described by the structure:

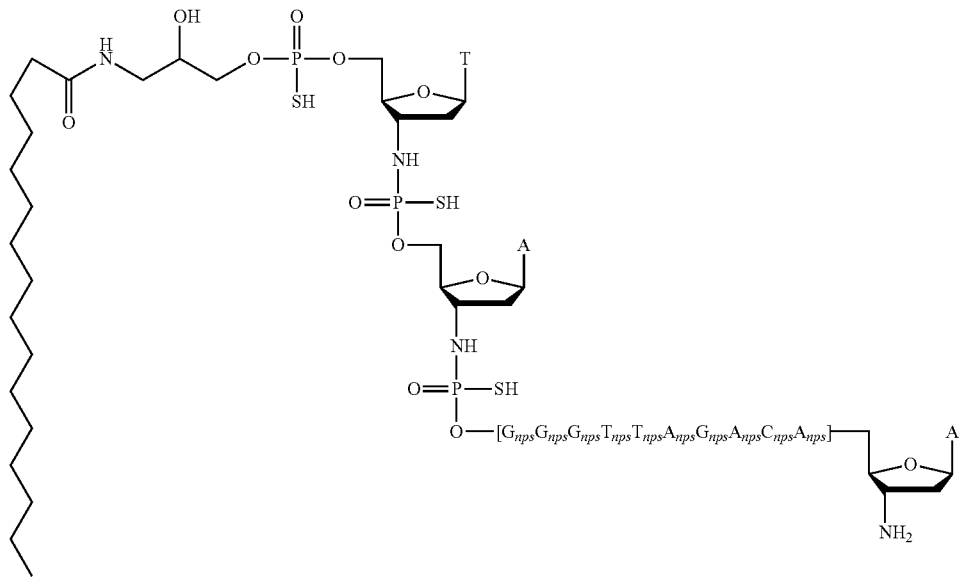

or a salt thereof;
where "nps" represents a thiophosphoramidate linkage (e.g., —NH—P(=O)(SH)—O— or a tautomer thereof, or a salt thereof), connecting the 3'-carbon of one nucleoside to the 5'-carbon of the adjacent nucleoside. In certain embodiments, the composition includes a pharmaceutically acceptable salt of the compound. In certain instances, the composition includes a sodium salt of the compound. In certain embodiments, the composition includes a divalent cation salt of the compound, such as a magnesium salt of the compound. In certain embodiments, the composition includes a trivalent cation salt of the compound, such as an aluminium salt of the compound.

In certain embodiments of the method, the oligonucleotide is described by the following structure, where each $M^{x+}$ is independently hydrogen or any convenient counterion of a salt, each x is independently 1, 2 or 3 and n is an integer from 5 to 13, such as 5, 6, 7, 8, 9, 10, 11, 12 or 13, such as n is 13:

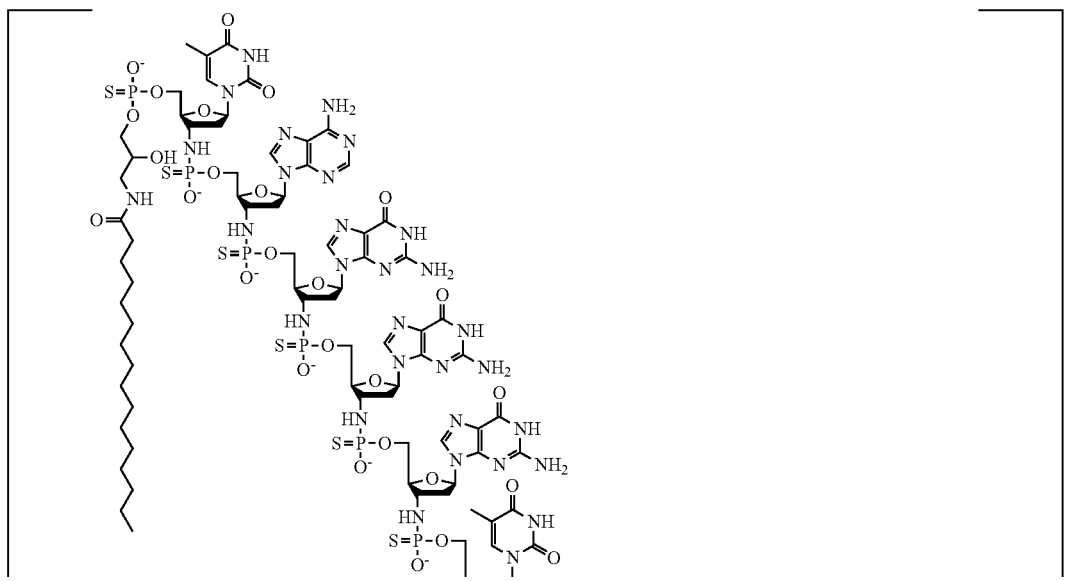

-continued

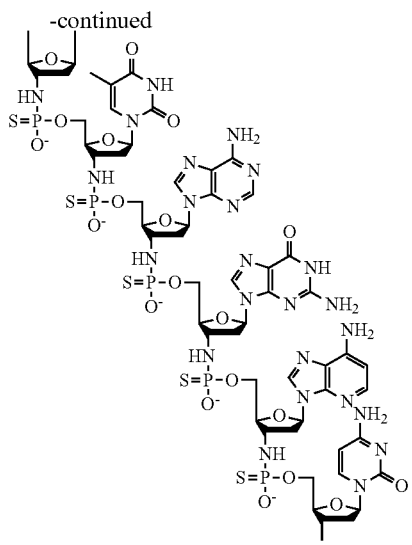

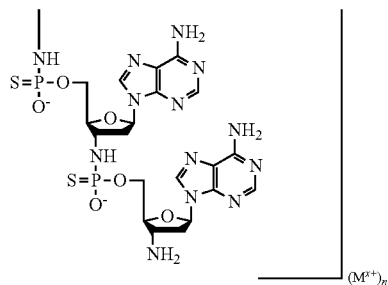

In certain instances, each x is 1. In certain instances, each x is independently 1 or 2. In certain instances, each x is independently 1 or 3. In certain instances, $M^{x+}$ is hydrogen.

In certain embodiments of the method, the oligonucleotide is described by the following structure and may include any convenient cationic counterions of a salt:

In certain embodiments of the method, the oligonucleotide is described by the structure:

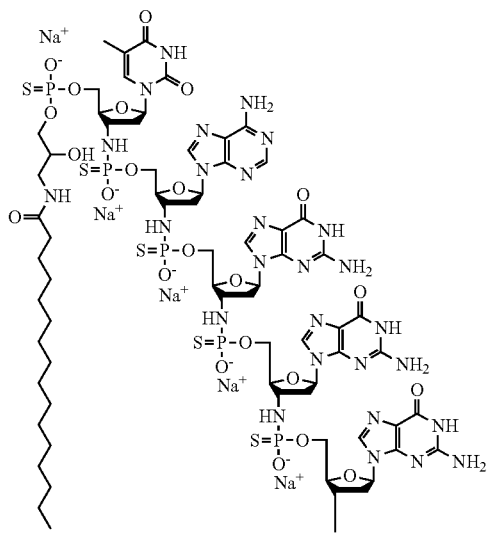

-continued

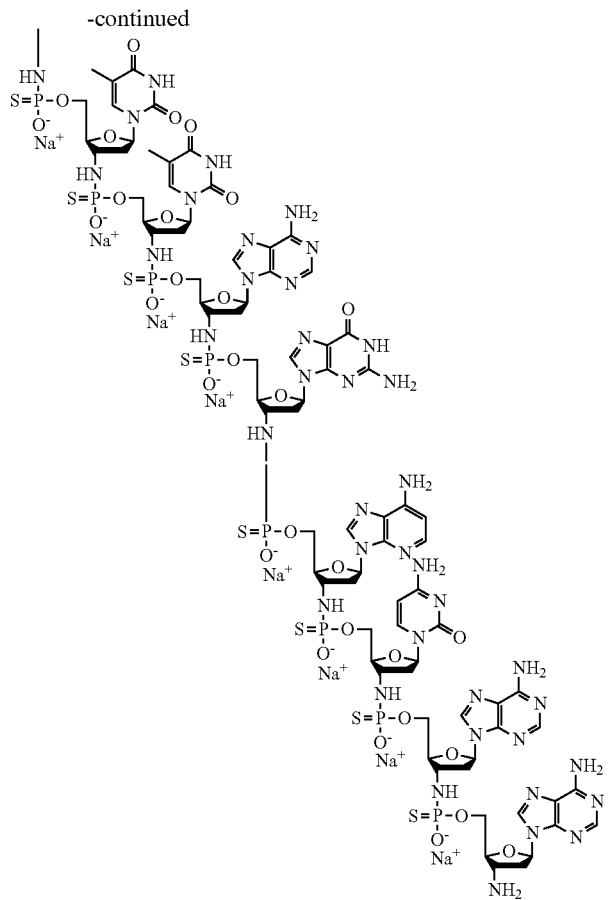

In certain embodiments of the method, the C11 nucleotide residue of the TAGGGTTAGACAA (SEQ ID NO:3) sequence derives from a 3'-protected aminonucleoside-5'-phosphoramidite monomer. By "derives from" is meant that the residue of interest is introduced during synthesis via a particular subunit. In certain instances, the T1 to A10, A12 and A13 residues of the TAGGGTTAGACAA (SEQ ID NO:3) sequence derive from 3'-protected amino-dinucleotide thiophosphoramidate-5'-phosphoramidite dimers.

In some cases, the method includes sequential coupling of the following 3'-protected amino-dinucleotide thiophosphoramidate-5'-phosphoramidite dimers and 3'-protected aminonucleoside-5'-phosphoramidite monomer to a terminal group of a solid phase support: TA, GG, GT, TA, GA, C and AA. It is understood that for simplicity, a protected phosphoramidite subunit that finds use in couplings of the subject methods may be depicted via the symbols $X^1$ or $X^1X^2$, where $X^1$ and $X^2$ are independently any convenient nucleosides linked via any convenient internucleoside linkage (e.g., as described herein). Any convenient synthetic strategies may be utilized in the subject methods. Some strategies of interest are shown below to demonstrate how the preparation of an oligonucleotide target sequence may be allocated to particular dimer and/or monomer subunits.

Exemplary retrosynthetic strategies represented by the following lists of sequential dimer and/or monomer subunits are provided for an exemplary target oligonucleotide sequence TAGGGTTAGACAA (SEQ ID NO:3). It is understood that this list of strategies is not exhaustive, and may be adapted for application to any convenient target oligonucleotide synthesis. In some embodiments, the method includes sequential coupling of one of the following series of 3'-protected amino-dinucleotide thiophosphoramidate-5'-phosphoramidite dimers and/or 3'-protected aminonucleoside-5'-phosphoramidite monomers to a terminal group of a solid phase support:

TA, G, G, G, T, T, A, G, A, C, A, A
T, AG, G, G, T, T, A, G, A, C, A, A
T, A, GG, G, T, T, A, G, A, C, A, A
T, A, G, GG, T, T, A, G, A, C, A, A
T, A, G, G, GT, T, A, G, A, C, A, A
T, A, G, G, G, TT, A, G, A, C, A, A
T, A, G, G, G, T, TA, G, A, C, A, A
T, A, G, G, G, T, T, AG, A, C, A, A
T, A, G, G, G, T, T, A, GA, C, A, A
T, A, G, G, G, T, T, A, G, AC, A, A
T, A, G, G, G, T, T, A, G, A, CA, A
T, A, G, G, G, T, T, A, G, A, C, AA
TA, GG, G, T, T, A, G, A, C, A, A
TA, G, GG, T, T, A, G, A, C, A, A
TA, G, G, GT, T, A, G, A, C, A, A
TA, G, G, G, TT, A, G, A, C, A, A
TA, G, G, G, T, TA, G, A, C, A, A
TA, G, G, G, T, T, AG, A, C, A, A
TA, G, G, G, T, T, A, GA, C, A, A
TA, G, G, G, T, T, A, G, AC, A, A
TA, G, G, G, T, T, A, G, A, CA, A
TA, G, G, G, T, T, A, G, A, C, AA
T, AG, GG, T, T, A, G, A, C, A, A
T, AG, G, GT, T, A, G, A, C, A, A

T, AG, G, G, TT, A, G, A, C, A, A
T, AG, G, G, T, TA, G, A, C, A, A
T, AG, G, G, T, T, AG, A, C, A, A
T, AG, G, G, T, T, A, GA, C, A, A
T, AG, G, G, T, T, A, G, AC, A, A
T, AG, G, G, T, T, A, G, A, CA, A
T, AG, G, G, T, T, A, G, A, C, AA
T, A, GG, GT, T, A, G, A, C, A, A
T, A, GG, G, TT, A, G, A, C, A, A
T, A, GG, G, T, TA, G, A, C, A, A
T, A, GG, G, T, T, AG, A, C, A, A
T, A, GG, G, T, T, A, GA, C, A, A
T, A, GG, G, T, T, A, G, AC, A, A
T, A, GG, G, T, T, A, G, A, CA, A
T, A, GG, G, T, T, A, G, A, C, AA
T, A, G, GG, TT, A, G, A, C, A, A
T, A, G, GG, T, TA, G, A, C, A, A
T, A, G, GG, T, T, AG, A, C, A, A
T, A, G, GG, T, T, A, GA, C, A, A
T, A, G, GG, T, T, A, G, AC, A, A
T, A, G, GG, T, T, A, G, A, CA, A
T, A, G, GG, T, T, A, G, A, C, AA
T, A, G, G, GT, TA, G, A, C, A, A
T, A, G, G, GT, T, AG, A, C, A, A
T, A, G, G, GT, T, A, GA, C, A, A
T, A, G, G, GT, T, A, G, AC, A, A
T, A, G, G, GT, T, A, G, A, CA, A
T, A, G, G, GT, T, A, G, A, C, AA
T, A, G, G, G, TT, AG, A, C, A, A
T, A, G, G, G, TT, A, GA, C, A, A
T, A, G, G, G, TT, A, G, AC, A, A
T, A, G, G, G, TT, A, G, A, CA, A
T, A, G, G, G, TT, A, G, A, C, AA
T, A, G, G, G, T, TA, GA, C, A, A
T, A, G, G, G, T, TA, G, AC, A, A
T, A, G, G, G, T, TA, G, A, CA, A
T, A, G, G, G, T, TA, G, A, C, AA
T, A, G, G, G, T, T, AG, AC, A, A
T, A, G, G, G, T, T, AG, A, CA, A
T, A, G, G, G, T, T, AG, A, C, AA
T, A, G, G, G, T, T, A, GA, CA, A
T, A, G, G, G, T, T, A, GA, C, AA
TA, GG, GT, T, A, G, A, C, A, A
TA, GG, G, TT, A, G, A, C, A, A
TA, GG, G, T, TA, G, A, C, A, A
TA, GG, G, T, T, AG, A, C, A, A
TA, GG, G, T, T, A, GA, C, A, A
TA, GG, G, T, T, A, G, AC, A, A
TA, GG, G, T, T, A, G, A, CA, A
TA, GG, G, T, T, A, G, A, C, AA
TA, G, GG, TT, A, G, A, C, A, A
TA, G, GG, T, TA, G, A, C, A, A
TA, G, GG, T, AG, A, C, A, A
TA, G, GG, T, T, A, GA, C, A, A
TA, G, GG, T, T, A, G, AC, A, A
TA, G, GG, T, T, A, G, A, CA, A
TA, G, GG, T, T, A, G, A, C, AA, etc.
TA, GG, GT, TA, G, A, C, A, A
TA, GG, GT, T, AG, A, C, A, A
TA, GG, GT, T, A, GA, C, A, A
TA, GG, GT, T, A, G, AC, A, A
TA, GG, GT, T, A, G, A, CA, A
TA, GG, GT, T, A, G, A, C, AA, etc
TA, GG, GT, TA, GA, C, A, A
TA, GG, GT, TA, G, AC, A, A
TA, GG, GT, TA, G, A, CA, A
TA, GG, GT, TA, G, A, C, AA, etc TA, G, GG, TT, AG, AC, A, A
TA, G, GG, TT, AG, A, CA, A
TA, G, GG, TT, AG, A, C, AA
TA, G, G, GT, TA, GA, CA, A
TA, G, G, GT, TA, GA, C, AA
TA, G, G, GT, TA, GA, CA, A
TA, G, G, G, TT, AG, AC, AA
TA, G, GG, T, TA, GA, CA, A
TA, G, GG, T, TA, GA, C, AA
TA, G, GG, T, TA, G, AC, AA, etc
T, A, G, GG, TT, AG, AC, AA
T, A, GG, G, TT, AG, AC, AA
T, AG, G, G, TT, AG, AC, AA
TA, G, G, G, TT, AG, AC, AA
T, AG, G, GT, T, AG, AC, AA, etc
T, AG, GG, T, T, AG, AC, AA, etc
T, AG, GG, TT, A, G, AC, AA, etc
T, AG, GG, TT, AG, A, C, AA, etc
T, AG, GG, TT, AG, AC, A, A
T, AG, GG, TT, AG, AC, AA
TA, G, GG, TT, AG, AC, AA
TA, GG, G, TT, AG, AC, AA
TA, GG, GT, T, AG, AC, AA
TA, GG, GT, TA, G, AC, AA
TA, GG, GT, TA, GA, C, AA or
TA, GG, GT, TA, GA, CA, A.

In some embodiments, the method includes sequential coupling of a series of 3'-protected amino-dinucleotide thiophosphoramidate-5'-phosphoramidite dimers and/or 3'-protected aminonucleoside-5'-phosphoramidite monomers to a terminal group of a solid phase support, where at least the final coupling of the synthesis is a dimer coupling. In certain embodiments, the second-to-last coupling and the final coupling are dimer couplings. In certain cases, when N is even, the method includes N/2 dimer couplings. In certain instances, when N is even, the method includes N/2-1 dimer couplings. In certain instances, when N is even, the method includes N/2-2 dimer couplings. In certain instances, when N is even, the method includes N/2-3 dimer couplings. In certain instances, when N is even, the method includes N/2-4 dimer couplings. In certain instances, when N is even, the method includes N/2-5 dimer couplings. In certain cases, when N is odd, the method includes N/2-1 dimer couplings. In certain instances, when N is odd, the method includes N/2-2 dimer couplings. In certain instances, when N is odd, the method includes N/2-3 dimer couplings. In certain instances, when N is odd, the method includes N/2-4 dimer couplings. In certain instances, when N is odd, the method includes N/2-5 dimer couplings. In certain instances, when N is odd, the method includes N/2-6 dimer couplings. For example, a sequential coupling of the following series of 3'-protected amino-dinucleotide thiophosphoramidate-5'-phosphoramidite dimers and/or 3'-protected aminonucleoside-5'-phosphoramidite monomers to a terminal group of a solid phase support:

T, A, G, G, G, T, T, A, G, A, C, AA
T, A, G, G, G, T, T, A, G, AC, AA
T, A, G, G, G, T, T, A, GA, C, AA
T, A, G, G, G, T, T, AG, A, C, AA
T, A, G, G, G, T, TA, G, A, C, AA
T, A, G, G, G, TT, A, G, A, C, AA
T, A, G, G, GT, T, A, G, A, C, AA
T, A, G, GG, T, T, A, G, A, C, AA
T, A, GG, G, T, T, A, G, A, C, AA
T, AG, G, G, T, T, A, G, A, C, AA
TA, G, G, G, T, T, A, G, A, C, AA, etc
T, A, G, G, G, T, T, AG, AC, AA T, A, G, G, G, TT, AG, AC, AA
T, A, G, GG, TT, AG, AC, AA
T, AG, GG, TT, AG, AC, AA
TA, G, GG, TT, AG, AC, AA
TA, GG, G, TT, AG, AC, AA
TA, GG, GT, T, AG, AC, AA
TA, GG, GT, TA, G, AC, AA
TA, GG, GT, TA, GA, C, AA.

In some embodiments of the method, the 3'-protected amino-dinucleotide thiophosphoramidate-5'-phosphoramidite dimer is described by the formula $X^1X^2$, where $X^1$ and $X^2$ are independently selected from a protected adenine, a protected cytosine, a protected guanine, thymine and uracil.

Lipid Modified Oligonucleotides

A variety of synthetic approaches can be used to conjugate a lipid moiety L' to the oligonucleotide, depending on the nature of the linkage selected, including the approaches described in Mishra et al., (1995) Biochemica et Biophysica Acta, 1264:229-237, Shea et al., (1990) Nucleic Acids Res. 18:3777-3783, and Rump et al., (1998) Bioconj. Chem. 9:341-349. The synthesis of compounds in which the lipid moiety is conjugated at the 5' or 3' terminus of the oligonucleotide can be achieved through use of suitable functional groups at the appropriate terminus, in some cases an amino group, which can be reacted with carboxylic acids, acid chlorides, anhydrides and active esters. Thiol groups may also be used as functional groups (see Kupihar et al., (2001) Bioorganic and Medicinal Chemistry 9:1241-1247). Both amino- and thiol-modifiers of different chain lengths are commercially available for oligonucleotide synthesis. Oligonucleotides having N3'→P5' phosphoramidate (e.g., N3'→P5' thiophosphoramidate) linkages contain 3'-amino groups (rather than 3'-hydroxy found in most conventional oligonucleotide chemistries), and hence these oligonucleotides provide a unique opportunity for conjugating lipid groups to the 3'-end of the oligonucleotide.

Various approaches can be used to attach lipid groups to the termini of oligonucleotides with the N3'→P5' phosphoramidate (e.g., N3'→P5' thiophosphoramidate) chemistry (see e.g., 3-palmitoylamido-1-O-(4,4'-dimethoxytrityl)-2-O-succinyl propanediol linker of Table 2). For attachment to the 3' terminus, the conjugated compounds can be synthesized by reacting the free 3'-amino group of the fully protected solid support bound oligonucleotide with the corresponding acid anhydride followed by deprotection with ammonia and purification. Alternatively, coupling of carboxylic acids of lipids to the free 3'-amino group of the support bound oligonucleotide using coupling agents such as carbodiimides, HBTU or 2-chloro-1-methylpyridinium iodide can be used to conjugate the lipid groups. These two methods form an amide bond between the lipid and the oligonucleotide. Lipids may also be attached to the oligonucleotide chain using a phosphoramidite derivative of the lipid coupled to the oligonucleotides during chain elongation. This approach yields a phosphoramidate (e.g., thiophosphoramidate) linkage connecting the lipid and the oligonucleotide (exemplified by propyl-palmitoyl and 2-hydroxy-propyl-palmitoyl compounds). Still another approach involves reaction of the free 3'-amino group of the fully protected support bound oligonucleotide with a suitable lipid aldehyde, followed by reduction with sodium cyanoborohydride, which produces an amine linkage.

For attachment to the 5' terminus, the oligonucleotide can be synthesized using a modified, lipid-containing solid support, followed by synthesis of the oligonucleotide in the 5' to 3' direction as described in Pongracz & Gryaznov (1999).

An example of the modified support is provided below. In the instance where n=14, the fatty acid is palmitic acid: reaction of 3-amino-1,2-propanediol with palmitoyl chloride, followed by dimethoxytritylation and succinylation provided the intermediate used for coupling to the solid support. R may be long chain alkyl amine controlled pore glass.

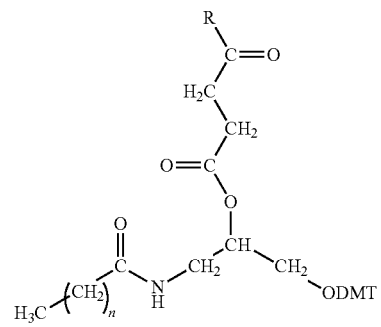

Dimers Useful for Making Oligonucleotides

In some embodiments of the method of making an oligonucleotide, the method includes contacting a support-bound free 3'-terminal group (e.g., a 3'-hydroxyl or 3'-amino group) with a dinucleotide dimer subunit to form an intersubunit linkage. In general, the dinucleotide dimer is 3'-protected and includes a 5'-group capable of coupling with the 3'-terminal group. In some embodiments, the dinucleotide dimer includes a 5'-phosphoramidite. The dinucleotide dimer may include a 3'-protected amino group or a 3'-protected hydroxyl group. In some embodiments, the dinucleotide is described by the formula $X^1X^2$, where $X^1$ and $X^2$ are independently any convenient nucleosides (e.g., A, C, G, T or U or a protected version thereof) linked via any convenient internucleoside linkage (e.g., as described herein). The dinucleotide may include any convenient internucleoside linkage between the two nucleosides. Internucleoside linkages of interest that find use in the dinucleotide dimers include, but are not limited to, a phosphodiester, a phosphotriester, a methylphosphonate, a phosphoramidate (e.g., a thiophosphoramidate) and a phosphorothioate linkage.

In some cases, the dinucleotide dimer is a 3'-protected-dinucleotide-5'-phosphoramidite dimer, or a synthetic precursor thereof, where the dinucleotide is described by the formula $X^1X^2$, where $X^1$ and $X^2$ are independently selected from A, C, G, T and U or a protected version thereof, and where $X^1$ and $X^2$ are linked via a phosphodiester, a phosphotriester, a methylphosphonate, a phosphoramidate (e.g., a thiophosphoramidate) or a phosphorothioate linkage, or a protected version thereof.

In some embodiments of the method of making an oligonucleotide, the method includes contacting a support-bound free 3'-amino group with a 3'-protected amino-dinucleotide phosphoramidate-5'-phosphoramidite dimer to form an internucleoside N3'→P5' phosphoramidite linkage. Any convenient 3'-protected amino-dinucleotide phosphoramidate-5'-phosphoramidite dimer, or synthetic precursors thereof, may find use in the subject methods. In some cases, the dimer may be represented by the one of the following sequences: AA, AC, AG, AT, AU, CA, CC, CG, CT or CU, GA, GC, GG, GT or GU, TA or UA, TC or UC, TG or UG and TT or UU. In some cases, the dimer includes protected 2'-hydroxyl groups.

In certain embodiments, the dinucleotide dimer is a dinucleotide thiophosphoramidate compound described by Formula (II):

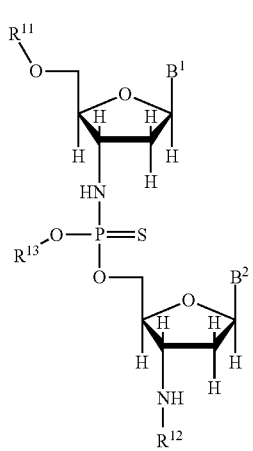

Formula (II)

wherein $B^1$ and $B^2$ are each independently a purine, a protected purine, a pyrimidine or a protected pyrimidine, or an analog thereof; $R^{11}$ is hydrogen, a protecting group or a phosphoramidite group; $R^{12}$ is hydrogen or a protecting group; and $R^{13}$ is hydrogen, an alkyl, a substituted alkyl, an aryl, a substituted aryl or a protecting group. In some cases, $B^1$ and/or $B^2$ include a nucleobase protecting group. It is understood that, when $R^{13}$ is hydrogen, an alkyl, a substituted alkyl, an aryl, a substituted aryl or a protecting group, some of the dinucleotide dimers described by Formula (II) may also exist in a salt form. Such forms in so far as they may exist, are intended to be included within the scope of the present disclosure.

In some embodiments of Formula (II), $R^{11}$ is hydrogen. In some embodiments of Formula (II), $R^{11}$ is a protecting group. Any convenient protecting groups may find use in the subject dimers of Formula (II). In some embodiments of Formula (II), $R^{11}$ is a levulinate-based protecting group. In some embodiments of Formula (II), $R^{11}$ is a levulinate protecting group (i.e., —COCH$_2$CH$_2$COCH$_3$). In some embodiments of Formula (II), $R^{11}$ is a 5'-phosphoramidite group.

In some embodiments of Formula (II), $R^{12}$ is hydrogen. In some embodiments of Formula (II), $R^{12}$ is a protecting group. In certain embodiments, $R^{12}$ is a trityl group (e.g., a triphenylmethyl (Trt), a monomethoxytrityl (MMT), or a dimethoxytrityl (DMT)). In some embodiments of Formula (II), $R^{12}$ is a Trt protecting group.

In some embodiments of Formula (II), $R^{12}$ is a photocleavable protecting group. Any convenient photocleavable protecting groups may find use in the preparation of the subject dinucleotide dimers and synthetic precursors thereof. In some embodiments of Formula (II), $R^{12}$ is a substituted pixyl protecting group, such as a nitro, fluoro, methyl, trifluoromethyl, and/or methoxy-substituted pixyl protecting group. In some embodiments of Formula (II), $R^{12}$ is a pixyl protecting group (i.e., a 9-(9-phenyl)xanthenyl).

In some embodiments of Formula (II), $R^{11}$ is a levunyl protecting group and $R^{12}$ is a trityl protecting group.

In some embodiments of Formula (II), $R^{13}$ is hydrogen. In some embodiments of Formula (II), $R^{13}$ is a protecting group. In certain embodiments, $R^{13}$ is a 2-cyano-ethyl group.

In certain embodiments, the 3'-protected amino-dinucleotide phosphoramidate-5'-phosphoramidite dimer is described by Formula (III):

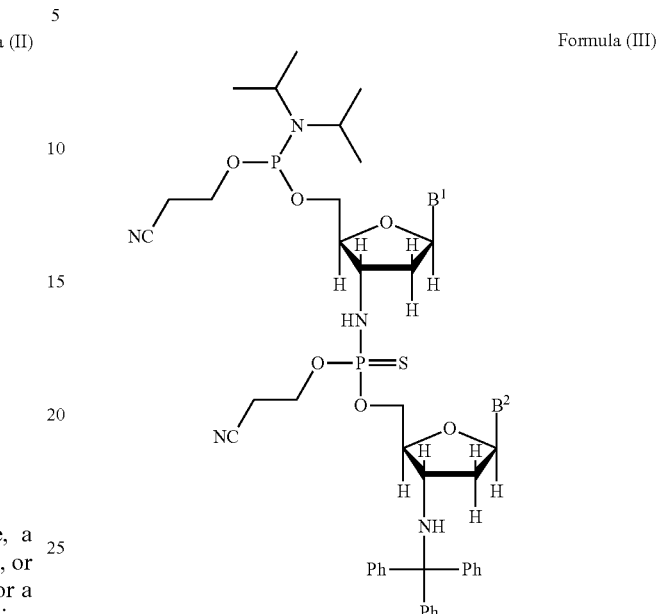

Formula (III)

wherein $B^1$ and $B^2$ are each independently a purine, a protected purine, a pyrimidine or a protected pyrimidine, or an analog thereof. In some cases, $B^1$ and/or $B^2$ include a nucleobase protecting group.

In certain embodiments, the 3'-protected amino-dinucleotide phosphoramidate-5'-phosphoramidite dimer is described by Formula (III):

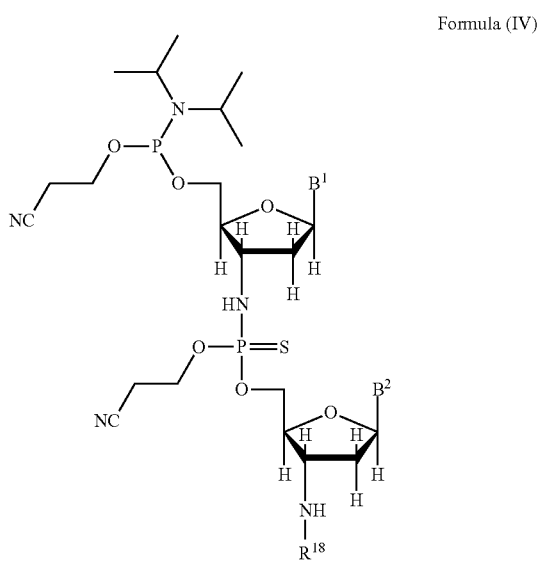

Formula (IV)

wherein $B^1$ and $B^2$ are each independently a purine, a protected purine, a pyrimidine or a protected pyrimidine, or an analog thereof; and $R^{18}$ is a trityl protecting group (such as a Trt, a DMT or a MMT) or a pixyl protecting group.

In some embodiments of Formulae (II) or (III), $B^1$ and $B^2$ are each independently selected from a protected adenine, a protected cytosine, a protected guanine, thymine and uracil.

In some embodiments of Formulae (II) or (III), $B^1$ and $B^2$ are each independently selected from A(Bz), A(DMF), C(Bz), G(isobutyryl), T and U. In some embodiments of Formulae (II) or (III), $B^1$ is A(Bz). In some embodiments of Formulae (II) or (III), $B^1$ is A(DMF). In some embodiments of Formulae (II) or (III), $B^1$ is C(Bz). In some embodiments of Formulae (II) or (III), $B^1$ is G(isobutyryl). In some embodiments of Formulae (II) or (III), $B^1$ is T or U. In some embodiments of Formulae (II) or (III), $B^2$ is A(Bz) or A(DMF). In some embodiments of Formulae (II) or (III), $B^2$ is C(Bz). In some embodiments of Formulae (II) or (III), $B^2$ is G(isobutyryl). In some embodiments of Formulae (II) or (III), $B^2$ is T or U.

In some embodiments of Formulae (II) or (III), $B^2$ is A(Bz) or A(DMF) and $B^2$ is A(Bz) or A(DMF). In some embodiments of Formulae (II) or (III), $B^1$ is A(Bz) or A(DMF) and $B^2$ is C(Bz). In some embodiments of Formulae (II) or (III), $B^1$ is A(Bz) or A(DMF) and $B^2$ is G(isobutyryl). In some embodiments of Formulae (II) or (III), $B^1$ is A(Bz) or A(DMF) and $B^2$ is T or U.

In some embodiments of Formulae (II) or (III), $B^1$ is C(Bz) and $B^2$ is A(Bz) or A(DMF). In some embodiments of Formulae (II) or (III), $B^1$ is C(Bz) and $B^2$ is C(Bz). In some embodiments of Formulae (II) or (III), $B^1$ is C(Bz) and $B^2$ is G(isobutyryl). In some embodiments of Formulae (II) or (III), $B^1$ is C(Bz) and $B^2$ is T or U.

In some embodiments of Formulae (II) or (III), $B^1$ is G(isobutyryl) and $B^2$ is A(Bz) or A(DMF). In some embodiments of Formulae (II) or (III), $B^1$ is G(isobutyryl) and $B^2$ is C(Bz). In some embodiments of Formulae (II) or (III), $B^1$ is G(isobutyryl) and $B^2$ is G(isobutyryl). In some embodiments of Formulae (II) or (III), $B^1$ is G(isobutyryl) and $B^2$ is T or U.

In some embodiments of Formulae (II) or (III), $B^1$ is T or U and $B^2$ is A(Bz) or A(DMF). In some embodiments of Formulae (II) or (III), $B^1$ is T or U and $B^2$ is C(Bz). In some embodiments of Formulae (II) or (III), $B^1$ is T or U and $B^2$ is G(isobutyryl). In some embodiments of Formulae (II) or (III), $B^1$ is T or U and $B^2$ is T or U. It is understood that any of the embodiments of Formulae (II) or (III) described herein, can also be applied to Formula (IV).

Any of the dimers described herein may be adapted for use in the subject methods. The subject dimers may be prepared according to any convenient methods from any convenient nucleoside monomers. Nucleoside monomers of interest that find use in the preparation of the subject nucleoside dimers include, but are not limited to, monomers 16, 17, 12 and 13 which are depicted in the synthetic schemes disclosed herein. Dinucleotide dimers of interest include non-phosphitylated dimers that find use in the preparation of the subject phosphitylated dinucleotide dimers, such as dimers 18 and 19 which find use in the preparation of phosphitylated dinucleotide dimers such as 20, or dimer 14 which finds use in the preparation of phosphitylated dinucleotide dimers such as 15.

In some embodiments, the dimers of Formulae (III) and (IV) are prepared via the method depicted in the following scheme:

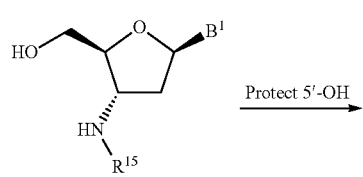

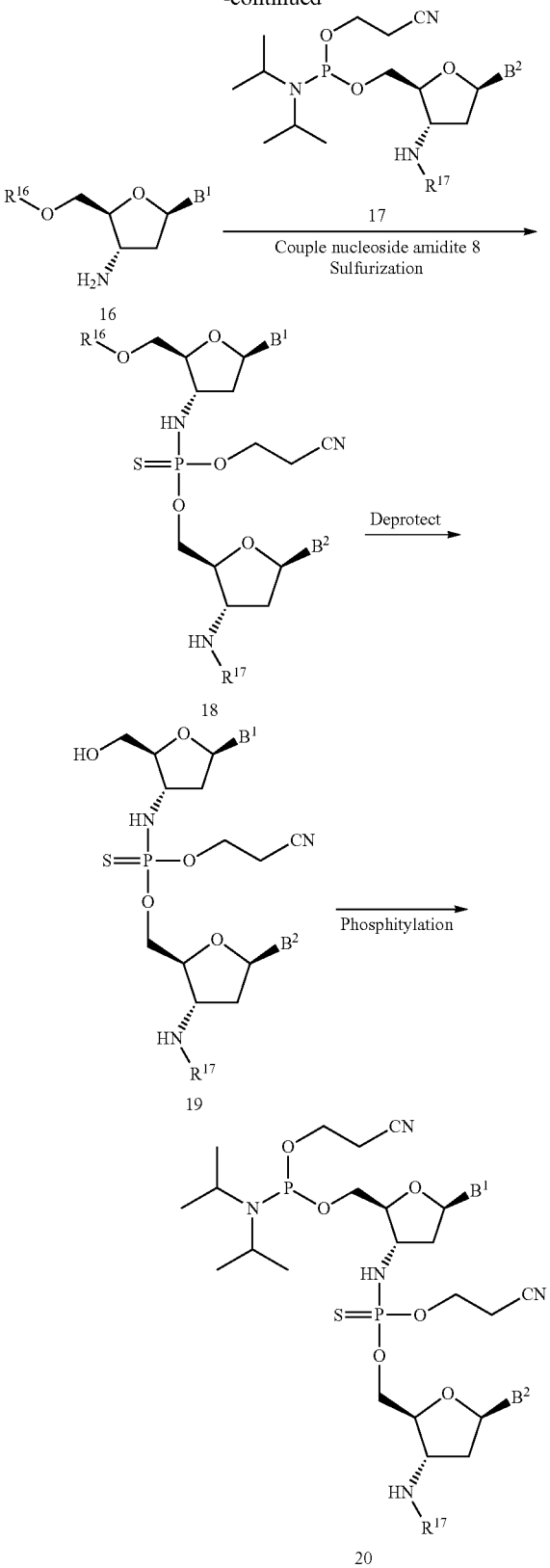

where $B^1$ and $B^2$ are each independently a purine, a protected purine, a pyrimidine or a protected pyrimidine, or an analog thereof; $R^{15}$ is hydrogen or an amino protecting group; $R^{17}$ is an amino protecting group; and $R^{16}$ is a hydroxyl protecting group. In certain embodiments, $R^{15}$ is hydrogen. In certain embodiments of monomer 16, $R^{16}$ is a silyl. In certain embodiments of monomer 16, $R^{16}$ is TBDMS (tert-butyldimethylsilyl). In certain embodiments of monomer 17, $R^{17}$ is a trityl (Trt). In certain embodiments of monomer 17, $R^{17}$ is a monomethoxytrityl (MMT).

In certain embodiments of monomer 17, $R^{17}$ is a dimethoxytrityl (DMT). In certain embodiments of monomer 17, $R^{17}$ is a pixyl. In certain embodiments of dimers 18-20, $R^{17}$ is a trityl (Trt). In certain embodiments of dimers 18-20, $R^{17}$ is a monomethoxytrityl (MMT). In certain embodiments of dimers 18-20, $R^{17}$ is a dimethoxytrityl (DMT). In certain embodiments of dimers 18-20, $R^{17}$ is a pixyl.

In some embodiments, the dimers of Formulae (III) and (IV) are prepared via the method depicted in the following scheme, where the monomer 13 is prepared from 11 via monomer 12 and coupled with a nucleoside amidite to produce dimers 14 which is converted to dimer 15:

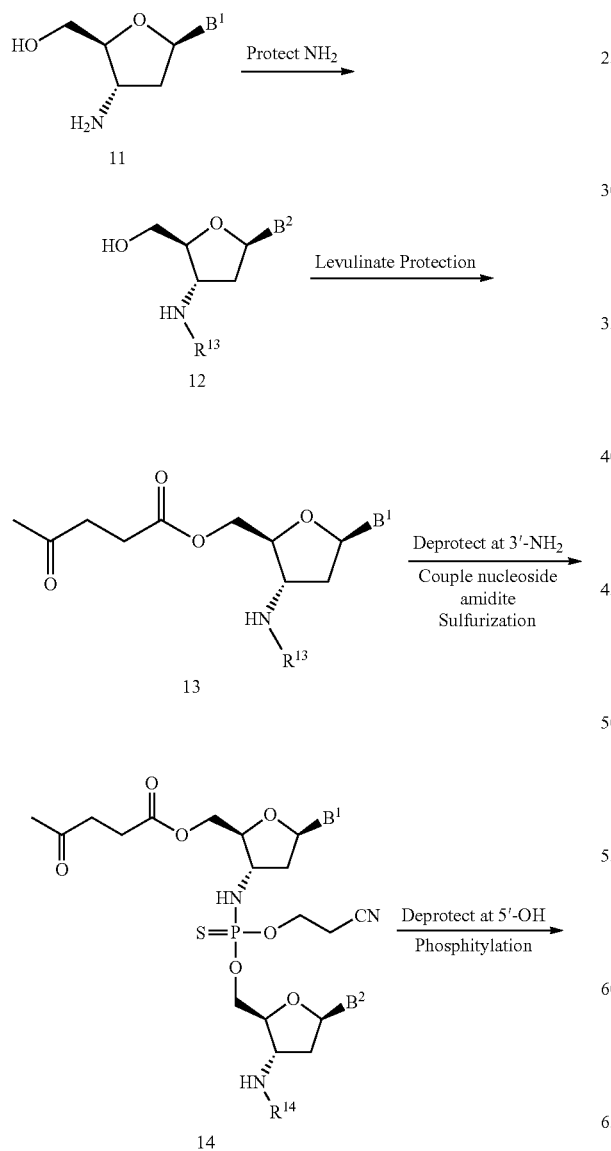

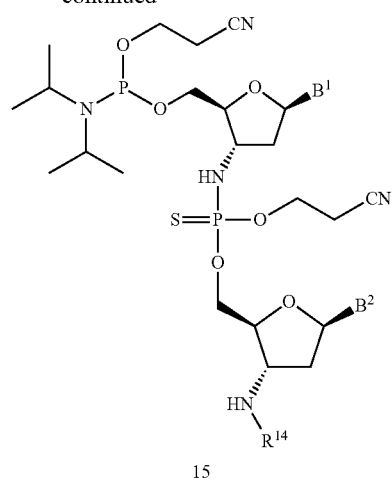

where $B^1$ and $B^2$ are each independently a purine, a protected purine, a pyrimidine or a protected pyrimidine, or an analog thereof; and $R^{13}$ and $R^{14}$ are each independently a protecting group. In certain embodiments of monomers 12 and 13, $R^{13}$ is a trityl. In certain embodiments of monomers 12 and 13, $R^{13}$ is a pixyl. In certain embodiments of dimers 14 and 15, $R^{14}$ is a trityl. In certain embodiments of dimers 14 and 15, $R^{14}$ is a dimethoxytrityl. In certain embodiments of dimers 14 and 15, $R^{14}$ is a monomethoxytrityl. In certain embodiments of dimers 14 and 15, $R^{14}$ is a pixyl.

Monomers of interest that find use in preparation of the subject dinucleotide dimers according to the methods described herein include, but are not limited to:

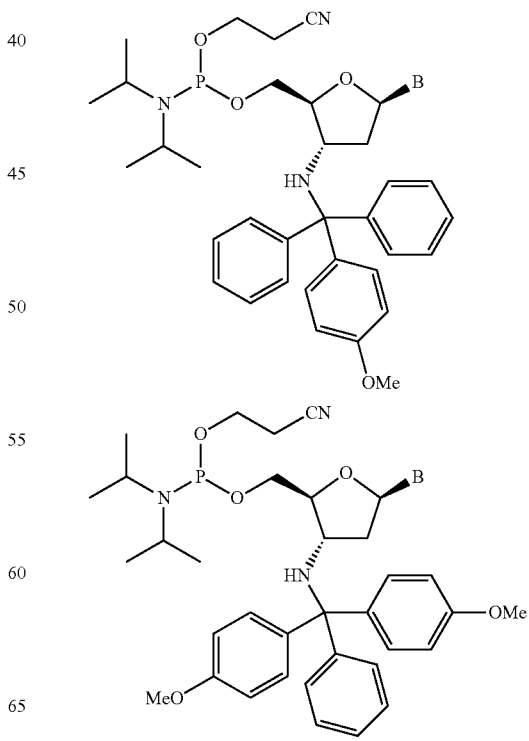

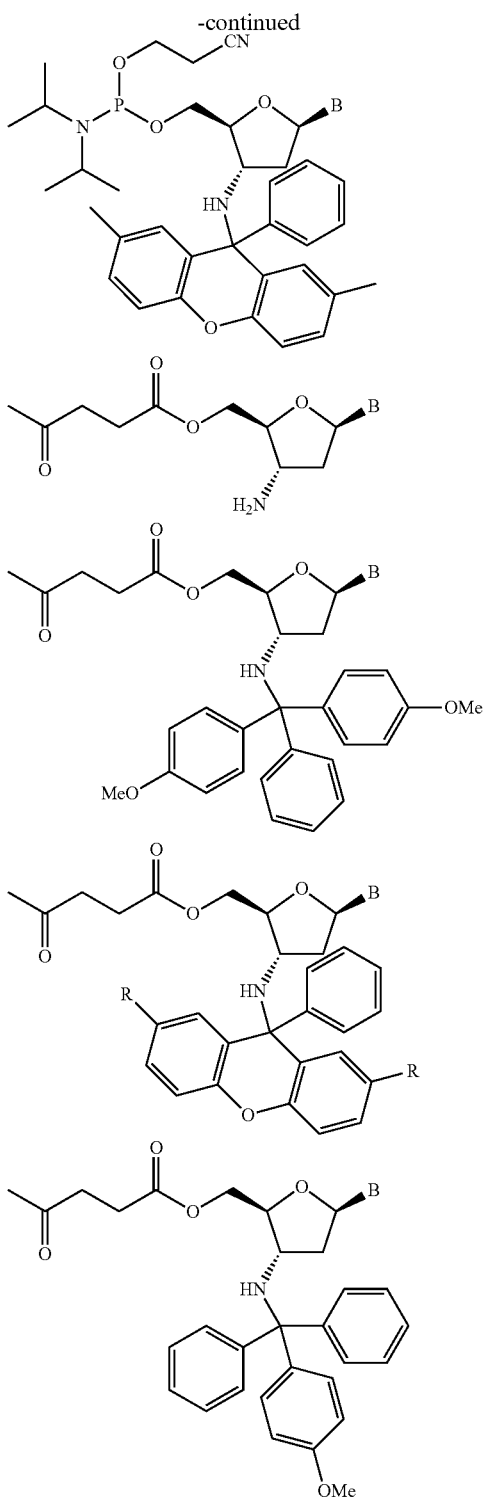

where B is a purine, a protected purine, a pyrimidine or a protected pyrimidine, or an analog thereof and R is hydrogen or an alkyl (e.g., methyl) or a halogen (e.g., bromo). In certain cases, B is selected from A(Bz), G(iBu), T, A(DMF), C(Bz), or U.

Oligonucleotide Compositions

In addition to a target oligonucleotide, a variety of non-target oligonucleotide synthesis products may be produced during oligonucleotide synthesis. Minor products that may be present in oligonucleotide preparations include, but are not limited to, deletion products (e.g., products lacking one or more nucleoside residues), products that include one or more protecting groups, terminated products (e.g., products that include a capped oligonucleotide chain), products that lack one or more nucleobases, products that include partially oxidized phosphoramidite linkages and products that include partially sulfurized linkages. As used herein, target oligonucleotide refers to an oligonucleotide sequence of interest, which is the target product of the method of preparation. As used herein, the terms "non-target product" and "minor product" are used interchangeably and refer to any oligonucleotide-containing product that is not the target product, and which may occur during and after the cycles of the target oligonucleotide synthesis.

The subject methods provide for compositions that include an improved purity of target oligonucleotide. In some embodiments, the composition includes 50% or more by weight of the target oligonucleotide, such as about 55% or more, about 60% or more, about 65% or more, about 70% or more, about 75% or more, about 80% or more, about 85% or more, about 90% or more, or even about 95% or more by weight of the target oligonucleotide. In certain embodiments, the composition includes 50% or more by weight of the target oligonucleotide. In certain embodiments, the composition includes 55% or more by weight of the target oligonucleotide. In certain embodiments, the composition includes 60% or more by weight of the target oligonucleotide. In certain embodiments, the composition includes 65% or more by weight of the target oligonucleotide. In certain embodiments, the composition includes 70% or more by weight of the target oligonucleotide. In certain embodiments, the composition includes 75% or more by weight of the target oligonucleotide. In certain embodiments, the composition includes 80% or more by weight of the target oligonucleotide. In certain embodiments, the composition includes 85% or more by weight of the target oligonucleotide. In certain embodiments, the composition includes 90% or more by weight of the target oligonucleotide. In certain embodiments, the composition includes 95% or more by weight of the target oligonucleotide.

In some embodiments, the subject methods provide for a coupling efficiency of 95% or more, such as 96% or more, 97% or more, 98% or more, or even 98% or more.

In some embodiments, the subject methods provide for a mean coupling efficiency that is 0.5% or more, such as 0.75% or more, 1.0% or more, 1.25% or more, 1.5% or more, 1.75% or more, 2.0% or more, 2.5% or more, or even 3.0% or more, than the mean coupling efficiency of a control synthesis performed using only monomer subunits. In certain embodiments, the subject methods provided for a 96% or greater coupling efficiency. In certain embodiments, the subject methods provides for a coupling efficiency that is 2% or greater than the coupling efficiency of a control synthesis performed using only monomer subunits.

After synthesis, the subject compositions may undergo one or more purification steps (e.g., HPLC chromatography, affinity chromatography, ion exchange chromatography, gel filtration, etc.), e.g., to remove one or more minor products from the target oligonucleotide. It is understood that, in the subject compositions, the reduced amounts of minor products and/or increased amount of target oligonucleotide provided by the subject methods of preparation may refer to such amounts and purities obtained immediately post synthesis and before any further purification or separation steps (e.g., HPLC chromatography) have been performed. As such, in some cases, the subject compositions may be referred to as synthesis preparations, e.g., unpurified synthesis preparations. By unpurified is meant that no chromatography purification steps have been performed on the composition. Chromatography purification refers to any convenient purification method that includes absorption of target polynucleotide to a chromatography support and subsequent elution of the target polynucleotide. In some cases, chromatography purification refers to reverse phase chromatography purification.

The subject methods provide for compositions including a reduced amount of one or more minor products. By reduced amount is meant that the amount by weight of the minor product in the composition relative to the target oligonucleotide is reduced relative to a control synthesis, e.g., a synthesis where the oligonucleotide is prepared using only monomer couplings. In some embodiments, the reduced amount of minor product is about 20% or less of the amount by weight of the target oligonucleotide, such as about 15% or less, about 10% or less, or about 5% or less of the amount by weight of the target oligonucleotide. In certain embodiments, the reduced amount of minor product is 20% or less of the amount by weight of the target oligonucleotide, such as 15% or less, 10% or less, 9% or less, 8% or less, 7% or less, 6% or less, 5% or less, 4% or less, 3% or less, 2% or less, or even 1% or less of the amount by weight of the target oligonucleotide. In certain embodiments, the minor product is a (N−x) product.

The subject methods of preparation may provide for compositions having a reduced amount of one or more (N−x) products relative to a target oligonucleotide of interest, where x is an integer from 1 to N−1 and N is the number of nucleoside residues in the target oligonucleotide. As such, (N−1) product may refer to any and all oligonucleotide products that lack any one nucleotide residue in comparison to a target oligonucleotide (e.g, a N product). As such, a (N−2) product refers to any and all oligonucleotide products that lack any two nucleotide residues in comparison to a target oligonucleotide (e.g, a N product). In certain embodiments, the minor product is a (N−1) product. In certain embodiments, the minor product is a (N−2) product. In certain embodiments, the minor product is a (N−3) product. In certain embodiments, the minor product is a (N−4) product. In certain embodiments, the minor product is a (N−5) product. In certain embodiments, the minor product is a (N−6) product. In certain embodiments, the minor product is a (N−7) product.

In certain embodiments, any of the compositions described herein that have a reduced amount of one or more (N−x) products relative to a target oligonucleotide of interest are unpurified.

In some embodiments, the subject compositions include a low ratio of (N−1) product to target oligonucleotide product. In some cases, the low ratio is less than (2.0×N) parts to 100 parts by weight of (N−1) product relative to target oligonucleotide, where N refers to the number of nucleotide residues in the target oligonucleotide sequence. In certain embodiments, the ratio is less than (1.9×N) parts to 100 parts by weight of (N−1) product relative to target oligonucleotide, such as less than (1.8×N) parts to 100, less than (1.7×N) parts to 100, less than (1.6×N) parts to 100, less than (1.5×N) parts to 100, less than (1.4×N) parts to 100, less than (1.3×N) parts to 100, less than (1.2×N) parts to 100, less than (1.1×N) parts to 100, less than (1.0×N) parts to 100, less than (0.9×N) parts to 100, less than (0.8×N) parts to 100, less than (0.7×N) parts to 100, less than (0.6×N) parts to 100, less than (0.5×N) parts to 100, less than (0.4×N) parts to 100, less than (0.3×N) parts to 100, less than (0.2×N) parts to 100, or even less than (0.1×N) parts to 100 parts by weight of (N−1) product relative to target oligonucleotide. In certain embodiments, the subject compositions include a low ratio of less than (1.5×N) parts to 100 parts by weight of (N−1) product relative to target oligonucleotide. In certain embodiments, the subject compositions include a low ratio of less than (1.2×N) parts to 100 parts by weight of (N−1) product relative to target oligonucleotide. In certain embodiments, the subject compositions include a low ratio of less than (1.0×N) parts to 100 parts by weight of (N−1) product relative to target oligonucleotide. In certain embodiments, the subject compositions include a low ratio of less than (0.5×N) parts to 100 parts by weight of (N−1) product relative to target oligonucleotide.

In some embodiments, the subject compositions include a low ratio of (N−2) product to target oligonucleotide product. In some cases, the low ratio is less than (2.0×N) parts to 100 parts by weight of (N−2) product relative to target oligonucleotide, where N refers to the number of nucleotide residues in the target oligonucleotide sequence. In certain embodiments, the ratio is less than (1.9×N) parts to 100 parts by weight of (N−2) product relative to target oligonucleotide, such as less than (1.8×N) parts to 100, less than (1.7×N) parts to 100, less than (1.6×N) parts to 100, less than (1.5×N) parts to 100, less than (1.4×N) parts to 100, less than (1.3×N) parts to 100, less than (1.2×N) parts to 100, less than (1.1×N) parts to 100, less than (1.0×N) parts to 100, less than (0.9×N) parts to 100, less than (0.8×N) parts to 100, less than (0.7×N) parts to 100, less than (0.6×N) parts to 100, less than (0.5×N) parts to 100, less than (0.4×N) parts to 100, less than (0.3×N) parts to 100, less than (0.2×N) parts to 100, or even less than (0.1×N) parts to 100 parts by weight of (N−2) product relative to target oligonucleotide. In certain embodiments, the subject compositions include a low ratio of less than (1.5×N) parts to 100 parts by weight of (N−2) product relative to target oligonucleotide. In certain embodiments, the subject compositions include a low ratio of less than (1.2×N) parts to 100 parts by weight of (N−2) product relative to target oligonucleotide. In certain embodiments, the subject compositions include a low ratio of less than (1.0×N) parts to 100 parts by weight of (N−1) product relative to target oligonucleotide. In certain embodiments, the subject compositions include a low ratio of less than (0.5×N) parts to 100 parts by weight of (N−2) product relative to target oligonucleotide.

In some embodiments, the subject compositions include (N−1) product in an amount of 20% or less of the total non-target oligonucleotides in the composition, such as 15% or less, 10% or less or even 5% or less of the total non-target oligonucleotides.

Any of a wide variety of oligonucleotide compositions can be prepared using the methods described herein. A variety of classes and types of oligonucleotides are of interest for preparation using the subject methods (e.g., as described herein). Oligonucleotides suitable for preparation according to the subject methods include, but are not limited to, anti-sense oligonucleotides, RNA oligonucelotides, siRNA oligonucleotides, RNAi oligonucleotides, DNA aptamers, micro RNA, and the like.

Oligonucleotides Complementary to RNA Component of Telomerase

Aspects of the disclosure include compounds and compositions including oligonucleotides complementary to the RNA component of human telomerase, and methods for making the same. The compounds may inhibit telomerase activity in cells with a high potency and have cellular uptake characteristics.

As summarized above, the subject methods provide for reduced amounts of non-target oligonucleotide products of the synthesis. In certain cases, the subject methods provide for increase amounts of target oligonucleotide product of the synthesis. In some embodiments, the subject methods provide for the preparation of compositions that have a reduced amount of one or more (N–x) products relative to a target oligonucleotide of interest. Table 1 sets forth amounts of interest of some non-target oligonucleotide products.

In certain embodiments, any of the compositions described herein that have a reduced amount of one or more (N–x) products relative to a target oligonucleotide of interest are unpurified.

TABLE 1

Levels of oligonucleotide products in compositions of interest. The subject compositions may include one or more of the following components at one of the levels indicated in Table 1.

| Product | % of composition (by weight) | Threshold Amounts relative to target (by weight) | Range relative to target (by weight) Oligos | Range relative to target (by weight) imetelstat |
|---|---|---|---|---|
| target | 50% or more, 55% or more, 60% or more, 65% or more, 70% or more, 75% or more, 80% or more, 85% or more, 90% or more, 95% or more | N/A | N/A | N/A |
| (N-1) products (including derivatives thereof such as Phenylacetyl and iBu derivatives) (e.g., post peak 1 (N-1) product) | less than 11% less than 10% less than 9% less than 8% less than 7% less than 6% less than 5% less than 4% less than 3% less than 2% less than 1% less than 0.5% | less than (1.9 × N) parts to 100, less than (1.8 × N) parts to 100, less than (1.7 × N) parts to 100, less than (1.6 × N) parts to 100, less than (1.5 × N) parts to 100, less than (1.4 × N) parts to 100, less than (1.3 × N) parts to 100, less than (1.2 × N) parts to 100, less than (1.1 × N) parts to 100, less than (0.9 × N) parts to 100, less than (0.8 × N) parts to 100, less than (0.7 × N) parts to 100, less than (0.6 × N) parts to 100, less than (0.5 × N) parts to 100, less than (0.4 × N) parts to 100, less than (0.3 × N) parts to 100, less than (0.2 × N) parts to 100, less than (0.1 × N) parts to 100 | from about (0.1 × N) to about (0.5 × N) parts in 100, from about (0.1 × N) to about (0.4 × N) parts in 100, from about (0.2 × N) to about (0.3 × N) parts in 100, about (0.1 × N) parts in 100, about (0.2 × N) parts in 100, about (0.3 × N) parts in 100, about (0.4 × N) parts in 100, about (0.5 × N) parts in 100, | from about 1 to about 20 parts in 100, from about 1 to about 10 parts in 100, from about 1 to about 8 parts in 100, from about 1 to about 6 parts in 100, from about 1 to about 5 parts in 100, from about 2 to about 4 parts in 100, about 1 parts in 100, about 2 parts in 100, about 3 parts in 100, about 4 parts in 100, about 5 parts in 100 less than 1 part in 4, less than 1 part in 5, less than 1 part in 6, less than 1 part in 7, less than 1 part in 8, less than 1 part in 9, less than 1 part in 10, less than 1 part in 20, less than 1 part in 25, less than 1 part in 100 |
| (N-2) and (N-3) products individually or combined (including derivatives thereof such as Phenylacetyl and iBu derivatives) (e.g., Post Peaks 2 + 3 + 4, or Post Peaks 3 + 4, or post Peak 2, 3 or 4) | 4% or more 6% or more 8% or more 10% or more 12% or more 14% or more 16% or more 18% or more 20% or more 25% or more less than 25% less than 20% less than 18% less than 16% less than 14% less than 12% less than 10% | at least (1.0 × N) parts to 100, at least (1.5 × N) parts to 100, at least (2.0 × N) parts to 100, at least (2.5 × N) parts to 100, at least (3.0 × N) parts to 100, at least (3.3 × N) parts to 100 less than (3.3 × N) parts to 100, less than (3.0 × N) parts to 100, less than (2.5 × N) parts to 100, less than (2.0 × N) parts to 100, less than (1.5 × N) parts to 100, less than (1.0 × N) parts to 100 | from about (1.0 × N) to about (5.0 × N) parts in 100, from about (2.0 × N) to about (5.0 × N) parts in 100, from about (2.5 × N) to about (4.0 × N) parts in 100, from about (3.0 × N) to about (4.0 × N) parts in 100, from about (3.0 × N) to about (3.5 × N) parts in 100 about (1.0 × N) parts in 100, about (1.5 × N) parts in 100, about (2.0 × N) parts in 100, about (2.5 × N) parts in 100, about | from about 5 to about 50 parts in 100, from about 10 to about 50 parts in 100, from about 20 to about 50 parts in 100, from about 30 to about 50 parts in 100, from about 5 to about 40 parts in 100, from about 5 to about 30 parts in 100, from about 5 to about 20 parts in 100, from about 10 to about 20 parts in 100 about 10 parts in 100, about 15 parts in 100, about 20 parts in 100, about 25 parts in 100, |

TABLE 1-continued

Levels of oligonucleotide products in compositions of interest. The subject compositions may include one or more of the following components at one of the levels indicated in Table 1.

| Product | % of composition (by weight) | Threshold Amounts relative to target (by weight) | Range relative to target (by weight) Oligos | Range relative to target (by weight) imetelstat |
|---|---|---|---|---|
| | | | (3.0 × N) parts in 100, about (3.3 × N) parts in 100, about (3.5 × N) parts in 100 | about 30 parts in 100, about 35 parts in 100, about 40 parts in 100, about 45 parts in 100, about 50 parts in 100 at least 5 parts in 100, at least 10 parts in 100, at least 12 parts in 100, at least 14 parts in 100, at least 15 parts in 100, at least 20 parts in 100, at least 30 parts in 100, at least 40 parts in 100 |
| Total non-target oligonucleotides | 45% or less, 40% or less, 35% or less, 30% or less, 25% or less, 20% or less | less than (8.5 × N) parts to 100, less than (8.0 × N) parts to 100, less than (7.5 × N) parts to 100, less than (7.0 × N) parts to 100, less than (6.5 × N) parts to 100, less than (6.0 × N) parts to 100, less than (5.5 × N) parts to 100, less than (5.0 × N) parts to 100, less than (4.5 × N) parts to 100, less than (4.0 × N) parts to 100, less than (3.5 × N) parts to 100, less than (3.0 × N) parts to 100, less than (2.5 × N) parts to 100, less than (2.0 × N) parts to 100, less than (1.5 × N) parts to 100, less than (1.0 × N) parts to 100 | from about (0.4 × N) to about (5.0 × N) parts in 100, from about (0.8 × N) to about (4.0 × N) parts in 100, from about (1.6 × N) to about (4.0 × N) parts in 100, from about (1.6 × N) to about (2.5 × N) parts in 100 about (1.9 × N) parts to 100 at least (1.0 × N) parts per 100, at least (1.5 × N) parts per 100, at least (2.0 × N) parts per 100 | from about 5 to about 50 parts in 100, from about 10 to about 50 parts in 100, from about 20 to about 50 parts in 100, from about 20 to about 40 parts in 100, from about 20 to about 30 parts in 100, about 25 parts in 100 at least 10 parts in 100, at least 15 parts in 100, at least 20 parts in 100, at least 25 parts in 100, less than 40 parts in 100, less than 30 parts in 100, less than 25 parts in 100, less than 20 parts in 100, less than 15 parts in 100 |

In certain embodiments, the composition has less than (2.0×N) parts to 100 parts by weight of (N−1) product relative to a compound, wherein the compound includes a polynucleotide having a sequence of N nucleoside subunits complementary to the RNA component of human telomerase, wherein at least two of the nucleoside subunits are joined by a N3'→P5' thiophosphoramidate inter-subunit linkage. In certain embodiments, the ratio is less than (1.9×N) parts to 100 parts by weight of (N−1) product relative to N product, such as less than (1.8×N) parts to 100, less than (1.7×N) parts to 100, less than (1.6×N) parts to 100, less than (1.5×N) parts to 100, less than (1.4×N) parts to 100, less than (1.3×N) parts to 100, less than (1.2×N) parts to 100, less than (1.1×N) parts to 100, less than (1.0×N) parts to 100, less than (0.9×N) parts to 100, less than (0.8×N) parts to 100, less than (0.7×N) parts to 100, less than (0.6×N) parts to 100, less than (0.5×N) parts to 100, less than (0.4×N) parts to 100, less than (0.3×N) parts to 100, less than (0.2×N) parts to 100, or even less than (0.1×N) parts to 100 parts by weight of (N−1) product relative to N product.

In some embodiments, the composition has less than 1 part in 4 by weight of a (N−1) product relative to a compound (such as, less than 1 part in 5, less than 1 part in 6, less than 1 part in 7, less than 1 part in 8, less than 1 part in 9, less than 1 part in 10, less than 1 part in 15, less than 1 part in 20, less than 1 part in 25, less than 1 part in 50, less than 1 part in 100 by weight of a (N−1) product relative to a compound), wherein the compound comprises a polynucleotide having a sequence of 10 or more nucleoside subunits complementary to the RNA component of human telomerase, wherein at least two of the nucleoside subunits are joined by a N3'→P5' thiophosphoramidate or oxophosphoramidate inter-subunit linkage. In certain embodiments, the polynucleotide has a sequence of 10 or more nucleoside subunits complementary to the RNA component of human telomerase, such as 10, 11, 12, 13, 14, 15, 16, 17, 18, 19, 20 or more nucleoside subunits.

In certain instances, the polynucleotide includes a sequence of 13 or more nucleoside subunits complementary to the RNA component of human telomerase, such as 15 or more, 20 or more, 30 or more, 50 or more nucleoside subunits complementary to the RNA component of human telomerase.

In certain embodiments, the polynucleotide includes a sequence of 7 or more nucleoside subunits complementary to the RNA component of human telomerase, such as 7, 8, 9, 10, 11, 12, 13, 14, 15, 16 or 17 nucleoside subunits complementary to the RNA component of human telomerase. In certain embodiments, the polynucleotide includes a sequence of nucleoside subunits complementary to the RNA component of human telomerase of between 11 and 18, such as between 11 and 16 contiguous nucleoside subunits complementary to the RNA component of human telomerase.

In some embodiments, the polynucleotide includes between 3 and 50 contiguous nucleoside subunits complementary to the RNA component of human telomerase, such as between 5 and 40, between 10 and 40, between 10 and 30, between 10 and 25, between 10 and 20, or between 12 and 15 nucleoside subunits. In certain embodiments, the oligonucleotide includes a sequence of 10 or more contiguous nucleoside subunits complementary to the RNA component of human telomerase. In certain embodiments, the composition has less than 1 part in 10 by weight of a (N−1) product relative to the compound. In certain embodiments, the composition has less than 1 part in 20 by weight of a (N−1) product relative to the compound. In certain embodiments, the composition has less than 1 part in 25 by weight of a (N−1) product relative to the compound. In certain embodiments, the composition has less than 1 part in 30 by weight of a (N−1) product relative to the compound. In certain embodiments, the composition has less than 1 part in 50 by weight of a (N−1) product relative to the compound.

In some embodiments, the composition has less that 1 part in 4 by weight of any (N−x) product relative to the compound, such as less than 1 part in 5, less than 1 part in 6, less than 1 part in 7, less than 1 part in 8, less than 1 part in 9, less than 1 part in 10, less than 1 part in 20, less than 1 part in 25, less than 1 part in 30, or even less than 1 part in 50 by weight, of any (N−x) product relative to the compound.

In some embodiments, the composition has less that 40 part in 100 by total weight of (N−x) polynucleotide-containing products relative to the compound, such as less than 35 parts in 100, less than 30 parts in 100, less than 25 parts in 100, less than 20 parts in 100, or even less than 15 parts in 100 by weight, of (N−x) polynucleotide-containing products relative to the compound.

In some embodiments, the composition has at least 5 parts in 100 by weight of (N−2) and (N−3) products relative to the compound, such as, at least 10 parts in 100 by weight, at least 12 parts in 100 by weight, at least 14 parts in 100 by weight, at least 15 parts in 100 by weight, at least 20 parts in 100 by weight, at least 30 parts in 100 by weight, or at least 40 parts in 100 by weight of (N−2) and (N−3) products relative to the compound.

In some embodiments, the composition has the following profile of (N−x) polynucleotide-containing products:

less that 1 part in 4 by weight of a (N−1) product relative to the N product; and at least 10 parts in 100 by weight of (N−2) and (N−3) products relative to the N product.

In certain embodiments, the oligonucleotide N product comprises a 3'-terminal nucleoside subunit that is absent in the (N−1) product.

The oligonucleotide compound may be described by the formula:

$$O\text{-}(x'\text{-}L')_n$$

where O represents the oligonucleotide including a sequence of nucleoside subunits complementary to the RNA component of human telomerase, x' is an optional linker group, L' represents the lipid moiety and n is an integer from 1-5.

Design of the compounds therefore requires the selection of two entities, O and L', and the determination of the structural linkage(s) between these entities, which may involve the optional linker group x'.

In some embodiments, the oligonucleotide compound may be described by the formula:

$$O\text{-}(x'\text{-}L')_n$$

where O represents the oligonucleotide including a sequence of nucleoside subunits complementary to the RNA component of human telomerase, x' is an optional linker group, L' represents the lipid moiety and n is 1, such as an oligonucleotide of Formula (I), or a salt thereof, wherein in Formula (I), Z is the lipid moiety, L is the optional linker and the B groups correspond to the sequence of nucleoside subunits complementary to the RNA component of human telomerase.

The oligonucleotide component O may be regarded as the "effector" component of the compound in that it is this component that effects inhibition of the telomerase enzyme by binding to the RNA component of telomerase. Thus, the sequence of O is selected such that it includes a region that is complementary to the sequence of the telomerase RNA, which is shown in SEQ ID NO:1 The region that is complementary to the telomerase RNA component may in theory be targeted to any portion of the telomerase RNA, but particular regions of the telomerase RNA are preferred target for inhibitory oligonucleotides. One preferred target region is the region spanning nucleotides 30-67 of SEQ ID NO: 1, which includes the "template region," an 11 nucleotide region of sequence 5'-CUAACCCUAAC-3' (SEQ ID NO: 2) that spans nucleotide 46-56 of SEQ ID NO: 1. The template region functions to specify the sequence of the telomeric repeats that telomerase adds to the chromosome ends and is essential to the activity of the telomerase enzyme (see Chen at al., Cell 100:503-514, 2000; Kim et al., Proc. Natl. Acad. Sci., USA 98(14):7982-7987, 2001). Compounds of the invention that contain an oligonucleotide moiety comprising a sequence complementary to all or part of the template region are thus particularly preferred. Another preferred target region is the region spanning nucleotides 137-179 of hTR (see Pruzan et al, Nucl. Acids Research, 30:559-588, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR.

The region of O that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide O is thus selected to include a sequence of at least 5 nucleotides exactly complementary to the telomerase RNA, and enhanced telomerase inhibition may be obtained if increasing lengths of complementary sequence are employed, such as at least 8, at least 10, at least 12, at least 13 or at least 15 nucleotides exactly complementary to the telomerase RNA. In other embodiments, the sequence of the oligonucleotide includes a sequence of from at least 5 to 20, from at least 8 to 20, from at least 10 to 20 or from at least 10 to 15 nucleotides exactly complementary to the telomerase RNA sequence. Optimal telomerase inhibitory activity may be obtained when the full length of the oligonucleotide O is selected to be complementary to the telomerase RNA. However, it is not necessary that the full length of the oligonucleotide component be exactly complementary to the target sequence, and the oligonucleotide sequence may include regions that are not complementary to the target sequence. Such regions may be added, for example, to confer other properties on the compound, such as sequences that facilitate purification. If the oligonucleotide component O is to include regions that are not complementary to the target sequence, such regions may be positioned at one or both of the 5' or 3' termini. In instances where the region of exact complementarity is targeted to the template region, effective telomerase inhibition may be achieved with a short (5-8 nucleotide) region of exact complementarity to which a telomerase-like (G-rich) sequence is joined at the 5' end.

Exemplary sequences that are complementary to the human telomerase RNA and which may be included as part of the oligonucleotide component O, or which may be used as the entire oligonucleotide component O include the following:

hTR complementary sequences (regions of Oligonucleotide sequence SEQ ID NO:1 of U.S. Publication 2012329858)

```
                                                  (SEQ ID NO: 1)
GGGUUGCGGA GGGUGGGCCU GGGAGGGGUG GUGGCCAUUU

UUUGUCUAAC CCUAACUGAG AAGGGCGUAG GCGCCGUGCU

UUUGCUCCCC GCGCGCUGUU UUUCUCGCUG ACUUUCAGCG

GGCGGAAAAG CCUCGGCCUG CCGCCUUCCA CCGUUCAUUC

UAGAGCAAAC AAAAAAUGUC AGCUGCUGGC CCGUUCGCCC

CUCCCGGGGA CCUGCGGCGG GUCGCCUGCC CAGCCCCCGA

ACCCCGCCUG GAGGCCGCGG UCGGCCCGGG GCUUCUCCGG

AGGCACCCAC UGCCACCGCG AAGAGUUGGG CUCUGUCAGC

CGCGGGUCUC UCGGGGCGA GGGCGAGGUU CAGGCCUUUC

AGGCCGCAGG AAGAGGAACG GAGCGAGUCC CCGCGCGCGG

CGCGAUUCCC UGAGCUGUGG GACGUGCACC CAGGACUCGG

CUCACACAUG C
                                                  (SEQ ID NO: 6)
GCTCTAGAATGAACGGTGGAAGGCGGCAGG 137-166

(SEQ ID NO: 7)
GTGGAAGGCGGCAGG 137-151

(SEQ ID NO: 8)
GGAAGGCGGCAGG 137-149

(SEQ ID NO: 9)
GTGGAAGGCGGCA 139-151

(SEQ ID NO: 10)
GTGGAAGGCGG 141-151

(SEQ ID NO: 11)
CGGTGGAAGGCGG 141-153

(SEQ ID NO: 12)
ACGGTGGAAGGCG 142-154
```

```
                                                  (SEQ ID NO: 13)
AACGGTGGAAGGCGGC 143-155

(SEQ ID NO: 14)
ATGAACGGTGGAAGGCGG 144-158

(SEQ ID NO: 15)
ACATTTTTTGTTTGCTCTAG 160-179

(SEQ ID NO: 3)
TAGGGTTAGACAA 42-54

(SEQ ID NO: 4)
GTTAGGGTTAG 46-56

(SEQ ID NO: 16)
GTTAGGGTTAGAC 44-56

(SEQ ID NO: 17)
GTTAGGGTTAGACAA 42-56

GGGTTAGAC 44-52

CAGTTAGGG 50-58

(SEQ ID NO: 18)
CCCTTCTCAGTT 54-65

(SEQ ID NO: 19)
CGCCCTTCTCAG 56-67
```

In some embodiments, the polynucleotide comprises a sequence selected from the group consisting of: GTTAGGGTTAG (SEQ ID NO:4); TAGGGTTAGACAA (SEQ ID NO:3); and CAGTTAGGGTTAG (SEQ ID NO:5).

The choice of the type of inter-nucleoside linkages used in the synthesis of the O component may be made from any of the available oligonucleotide chemistries, including but not limited to, phosphodiester, phosphotriester, methylphosphonate, P3'→N5' phosphoramidate, N3'→P5' phosphoramidate, N3'→P5' thiophosphoramidate, and phosphorothioate linkages.

In some embodiments, the oligonucleotide component O has at least one N3'→P5' phosphoramidate (e.g., N3'→P5' thiophosphoramidate) linkage. In certain embodiments, the nucleoside subunits complementary to the RNA component of human telomerase are all joined by N3'→P5' phosphoramidate inter-subunit linkages. In certain cases, the N3'→P5' phosphoramidate inter-subunit linkages are N3'→P5' thiophosphoramidate inter-subunit linkages. In certain cases, the N3'→P5' phosphoramidate inter-subunit linkages are N3'→P5' oxo-phosphoramidate inter-subunit linkages.

In certain cases, the N3'→P5' thiophosphoramidate inter-subunit linkage has the following structure:

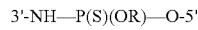

3'-NH—P(S)(OR)—O-5' where R is selected from the group consisting of hydrogen, an alkyl, a substituted alkyl, an aryl, a substituted aryl and a phosphate protecting group. It is understood that some of the oligonucleotide components O including an inter-subunit linkage described by the formula above where R is selected from the group consisting of hydrogen, an alkyl, a substituted alkyl, an aryl, a substituted aryl and a phosphate protecting group, may also exist in a salt form. Such forms in so far as they may exist, are intended to be included within the scope of the present disclosure.

In some instances, the N3'→P5' thiophosphoramidate inter-subunit linkage is described by the following structure:

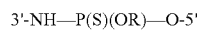

3'-NH—P(S)(OR)—O-5' where R is hydrogen. It is understood that for any of the oligonucleotide components O described herein that include such an inter-subunit linkage, such oligonucleotide components O may also include any convenient salt forms of the linkage. As such, the inter-subunit linkage may be in a salt form that includes any convenient counterion.

The compounds of the invention are more effective in producing telomerase inhibition in cells than corresponding oligonucleotides that are not conjugated to lipid components. The lipid component L' is believed to function to enhance cellular uptake of the compound, particularly in facilitating passage through the cellular membrane. While the mechanism by which this occurs has not been fully elucidated, one possibility is that the lipid component may facilitate binding of the compound to the cell membrane as either a single molecule, or an aggregate (micellar) form, with subsequent internalization. However, understanding of the precise mechanism is not required for the invention to be utilized.

The lipid component may be any lipid or lipid derivative that provides enhanced cellular uptake compared to the unmodified oligonucleotide. Preferred lipids are hydrocarbons, fats (e.g., glycerides, fatty acids and fatty acid derivatives, such as fatty amides) and sterols. Where the lipid component is a hydrocarbons, the L' component may be a substituted or unsubstituted cyclic hydrocarbon or an aliphatic straight chain or branched hydrocarbon, which may be saturated or unsaturated. Preferred examples are straight chain unbranched hydrocarbons that are fully saturated or polyunsaturated. The length of the hydrocarbon chain may vary from C2-C30, but optimal telomerase inhibition may be obtained with carbon chains that are C8-C22. Preferred examples of saturated hydrocarbons (alkanes) are listed below:

Systematic Name/Carbon Chain
Tetradecane $C_{14}H_{30}$
Pentadecane $C_{15}H_{32}$
Hexadecane $C_{16}H_{34}$
Heptadecane $C_{17}H_{36}$
Octadecane $C_{18}H_{38}$
Nonadecane $C_{19}H_{40}$
Eicosane $C_{20}H_{42}$ Mono- and poly-unsaturated forms (alkenes and polyenes, such as alkadienes and alkatrienes) of hydrocarbons may also be selected, with compounds having one to three double bonds being preferred, although compound having more double bonds may be employed. Alkynes (containing one or more triple bonds) and alkenynes (triple bond(s) and double bond(s)) may also be utilized.

Substituted forms of hydrocarbons may be employed in the compounds of the invention, with substituent groups that are inert in vivo and in vitro being preferred. A particularly preferred substituent is fluorine. Exemplary generic structures of polyfluorinated hydrocarbons include: $CF_3(CF_2)_n$—$(CH_2)_m$— where m is at least 1, preferably at least 2, and n=1-30, such as fluorotridecane: $CF_3(CF_2)_9(CH_2)_3$; and $CH_3(CH_2)_a(CF_2)_b(CH_2)_c$— where a, b and c are independently 1-30.

Other suitable lipid components include simple fatty acids and fatty acid derivatives, glycerides and more complex lipids such as sterols, for example cholesterol. Fatty acids and their derivatives may be fully saturated or mono- or poly-unsaturated. The length of the carbon chain may vary from C2-C30, but optimal telomerase inhibition may be obtained with carbon chains that are C8-C22. Preferred examples of saturated fatty acids are listed below:

Systematic Name/Trivial Name/Carbon Chain
Tetradecanoic myristic 14:0
Hexadecanoic palmitic 16:0
Octadecanoic stearic 18:0
Eicosanoic arachidic 20:0

Mono- and poly-unsaturated forms of fatty acids may also be employed, with compounds having one to three double bonds being preferred, although compounds having more double bonds may also be employed. Examples of common mono- and poly-unsaturated fatty acids that may be employed include:

Systematic Name/Trivial Name/Carbon Chain
Cis-9-hexadecanoic palmitoleic 16:1 (n-7)
Cis-6-octadecanoic petroselinic 18:1 (n-12)
Cis-9-octadecanoic oleic 18:1 (n-9)
9,12-octadecadienoic linoleic 18:2 (n-6)
6,9,12-octadecatrienoic gamma-linoleic 18:3 (n-6)
9,12,15-octadecatrienoic alpha-linoleic 18:3 (n-3)
5,8,11,14-eicosatetraenoic arachidonic 20:4 (n-6)

Fatty acids with one or more triple bonds in the carbon chain, as well as branched fatty acids may also be employed in the compounds of the invention. Substituted forms of fatty acids may be employed in the compounds of the invention. As with the hydrocarbon groups, substituent groups that are inert in vivo and in vitro are preferred, with fluorine being a particularly preferred. Exemplary generic structures of polyfluorinated derivatives of fatty acids suitable for use in the invention are: $CF_3(CF_2)_n$—$(CH_2)_m CO$— where m is at least 1, preferably at least 2, and n=1-30, and $CH_3(CH_2)_a(CF_2)_b(CH_2)_c CO$— where a, b and c are independently 1-30.

In some cases, between one and five L' components (n=1-5) are covalently linked to the O component, optionally via a linker. More usually 1 or two L' components are utilized (n=1 or 2). Where more than one L' component is linked to the O component, each L' component is independently selected.

It will be appreciated that compounds of the invention described as having a specified hydrocarbon as the L' moiety and compounds described as having a specified fatty acid (with the same number of carbon atoms as the specified hydrocarbon) are closely related and differ in structure only in the nature of the bond that joins the L' moiety to the oligonucleotide, which in turn is a result of the synthesis procedure used to produce the compound. For example, and as described in more detail below, when compounds are synthesized having the L' moiety conjugated to the 3'-amino terminus of an oligonucleotide (having phosphoramidate or thiophosphoramidate internucleoside linkages), the use of the aldehyde form of a fatty acid (a fatty aldehyde) as the starting material results in the formation of an amine linkage between the lipid chain and the oligonucleotide, such that the lipid group appears as a hydrocarbon. In contrast, use of the carboxylic acid, acid anhydride or acid chloride forms of the same fatty acid results in the formation of an amide linkage, such that the lipid group appears as a fatty acid derivative, specifically in this instance a fatty amide (as noted in the definitions section above, for the sake of simplicity, the term "fatty acid" when describing the conjugated L' group is used broadly herein to include fatty acid derivatives, including fatty amides). This is illustrated in the following schematics which depict the 3'-amino terminus of a phosphoramidate oligonucleotide joined to a C14 lipid component. In schematic A, L' is tetradecanoic acid (myristic acid), in which the connection between L' and O groups is an amide. In schematic B, L' is tetradecane, and the connection between the L' and O groups is an amine.

Schematic A

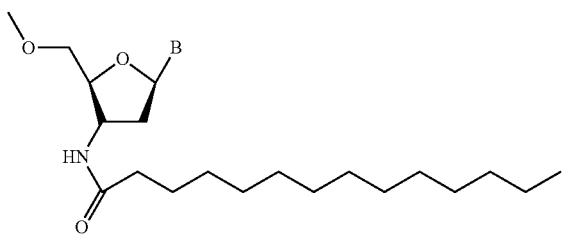

Schematic B

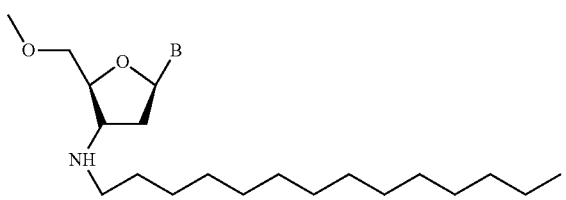

The linkage between the O and L' components may be a direct linkage, or may be via an optional linker moiety, e.g., x' or optional linker L of Formula (I). The linker group may serve to facilitate the chemical synthesis of the compounds. Whether or not a linker group is used to mediate the conjugation of the O and L' components, there are multiple sites on the oligonucleotide component O to which the L' component(s) may be conveniently conjugated. Suitable linkage points include the 5' and 3' termini, one or more sugar rings, the internucleoside backbone and the nucleobases of the oligonucleotide. In some cases, the L' moiety is attached to the 3' or 5' terminus of the oligonucleotide.

If the L' component is to be attached to the 3' terminus, the attachment may be directly to the 3' substituent, which in the case of the preferred phosphoramidate and thiophosphoramidate oligonucleotides is the 3'-amino group, and in other instances, such as conventional phosphodiester oligonucleotides, is a 3-hydroxy group. Alternatively, the L' moiety may be linked via a 3'-linked phosphate group, in which a hexadecane hydrocarbon is linked to the 3' phosphate of a thiophosphoramidate oligonucleotide through an O-alkyl linker. If the L' moiety is to be linked to the 5' terminus, it may be attached through a 5'-linked phosphate group. Attachment to a base on the 0 moiety may through any suitable atom, for example to the N2 amino group of guanosine. Where n>1 such that a plurality of lipid moieties is to be attached to the O component, the individually selected L' components may be attached at any suitable site(s). For example, one L' group may be attached to each terminus, various L' groups may be attached to the bases, or two or more L' groups may be attached at one terminus.

The optional linker component x' may be used to join the O and L' components of the compounds. It is understood that the optional linker (e.g., x', or L of Formula (I)) may be attached to the polynucleotide (e.g., O) through a terminal phosphate group, e.g., a 3'-linked or a 5'-linked phosphate group. If a linker is to be employed, it is incorporated into the synthesis procedures as described herein. Examples of suitable linker groups include amino glycerol and O-alkyl glycerol-type linkers which respectively can be depicted by the generic structures:

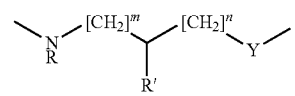

wherein R'=H, OH, NH$_2$ or SH; Y=O, S or NR; R=H, an alkyl or a substituted alkyl; and n and m are independently integers between 1-18.

Specific examples of suitable linkers are the aminoglycerol linker in which R'=OH, Y=O, and m and n are each 1:

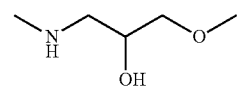

the bis-aminoglycerol linker, in which R'=OH, Y=NH, and m and n are each 1:

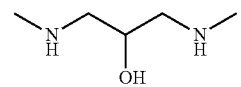

and the O-alkyl glycerol linker in which R=H:

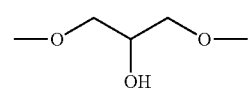

Figure 1B:
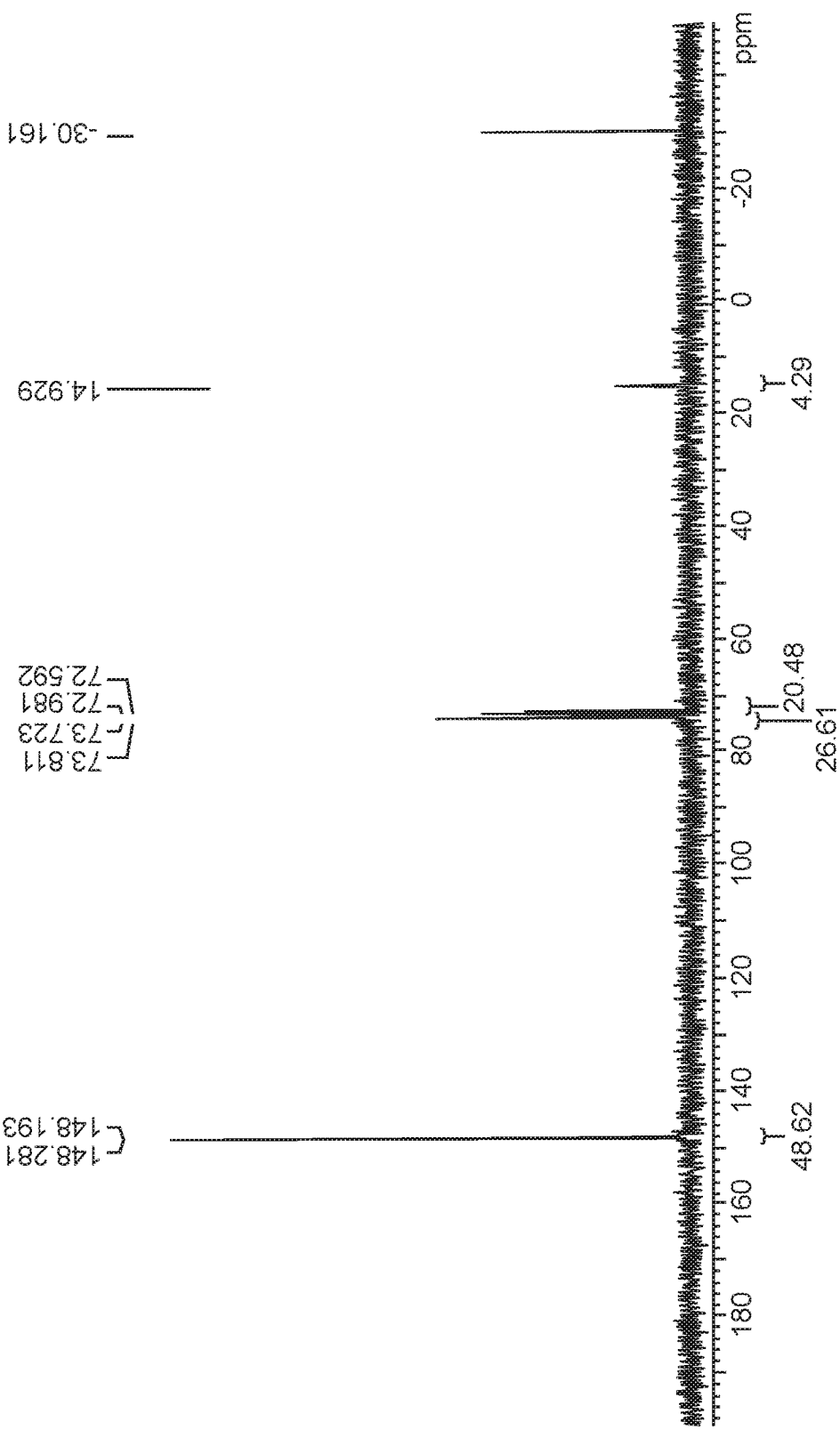
Figure 2B:
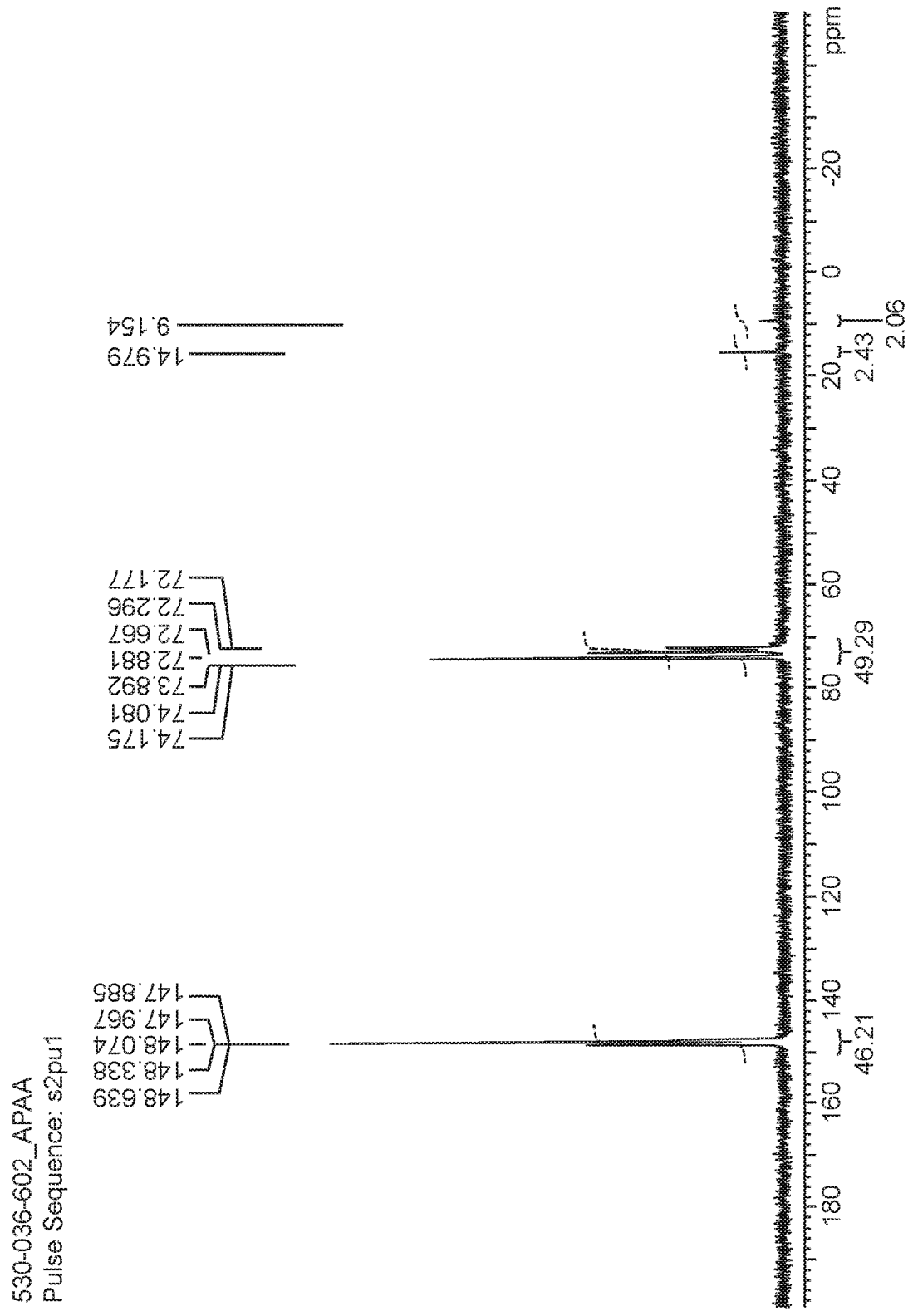
Figure 3A:
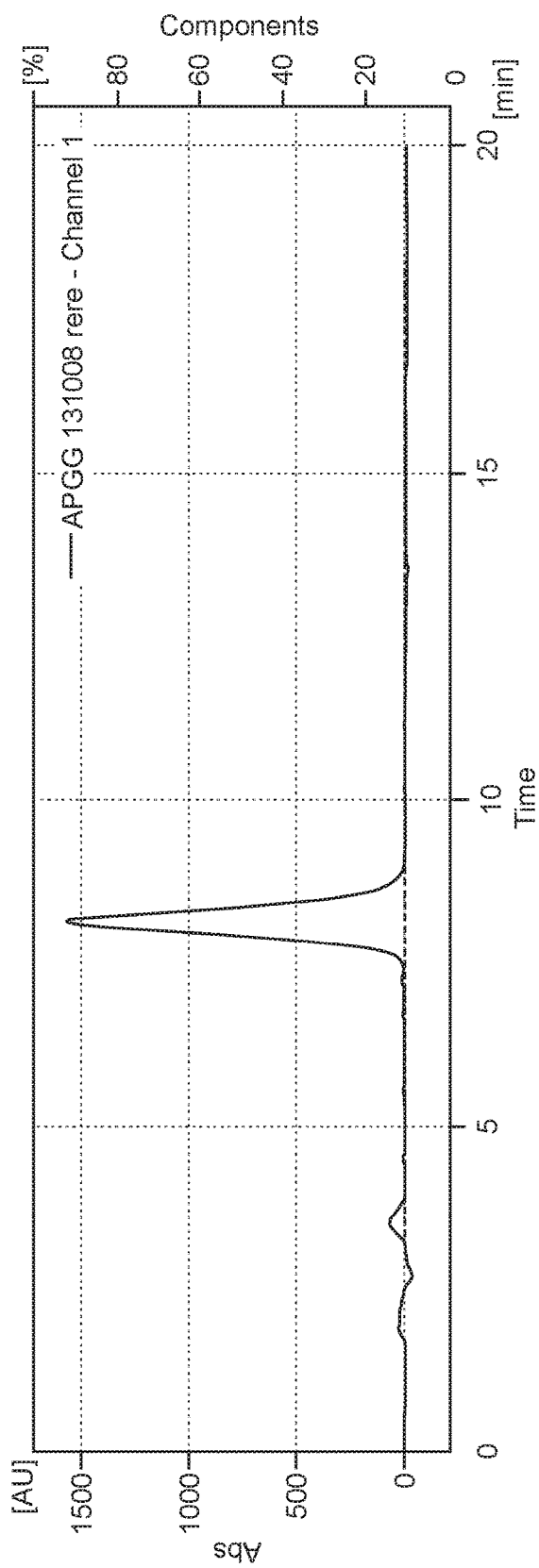
Figure 4A:
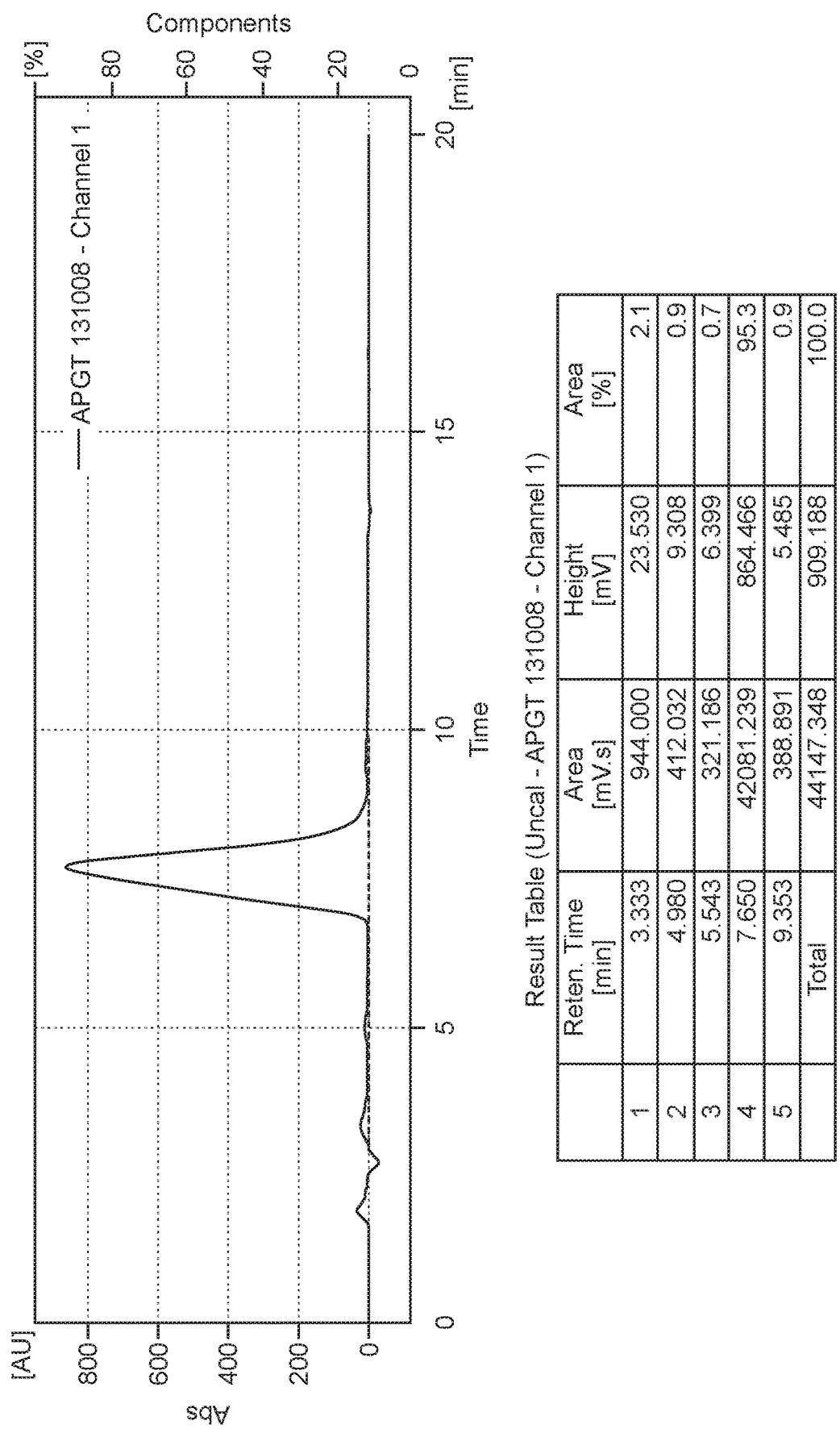
FIGS. 4A and 4B show an HPLC chromatogram (A) and $^{31}$P NMR spectra (B) for a GT dimer thiophosphoramidate (compound 7d, Scheme 1).
Figure 4B:
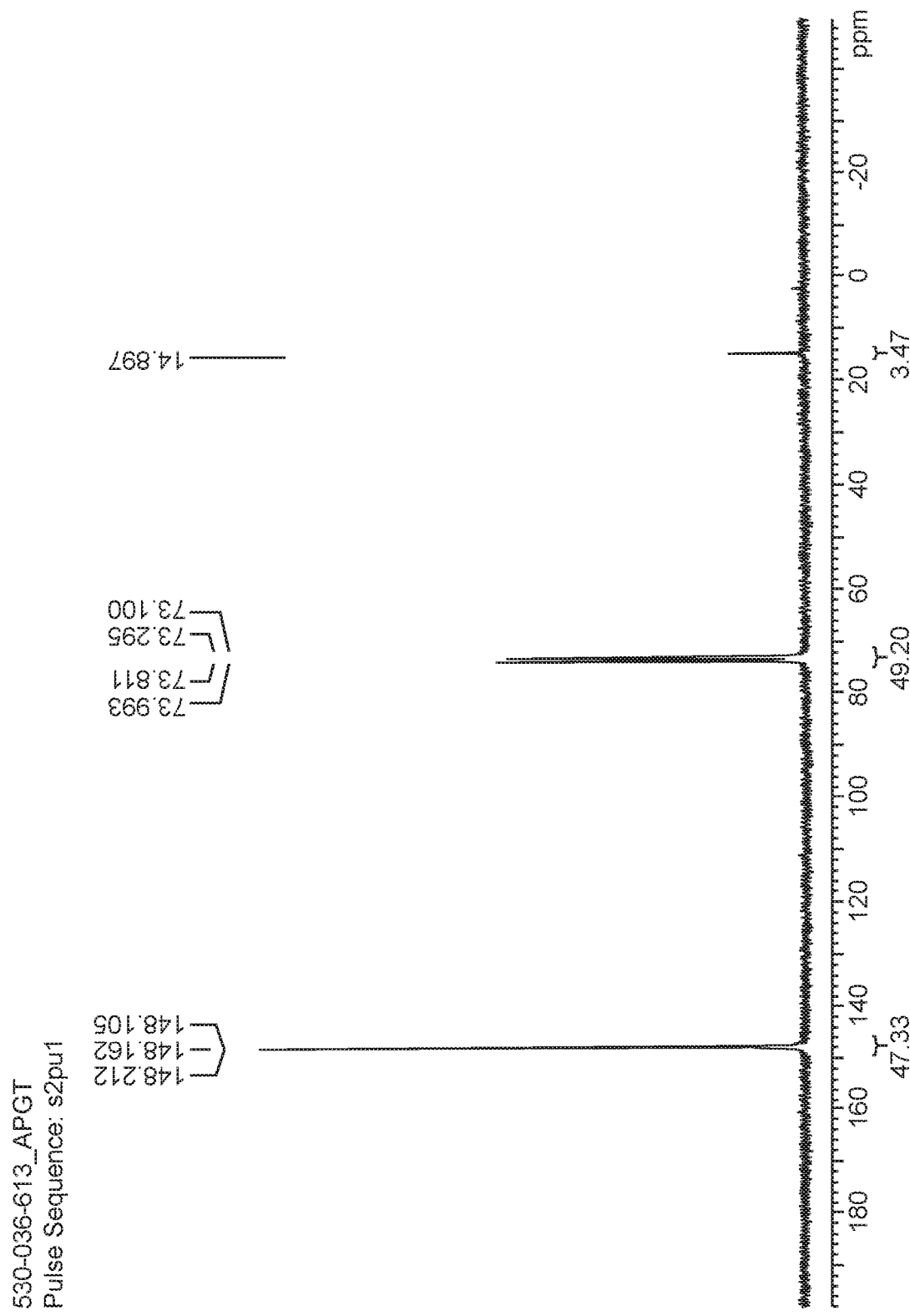
Figure 6A:
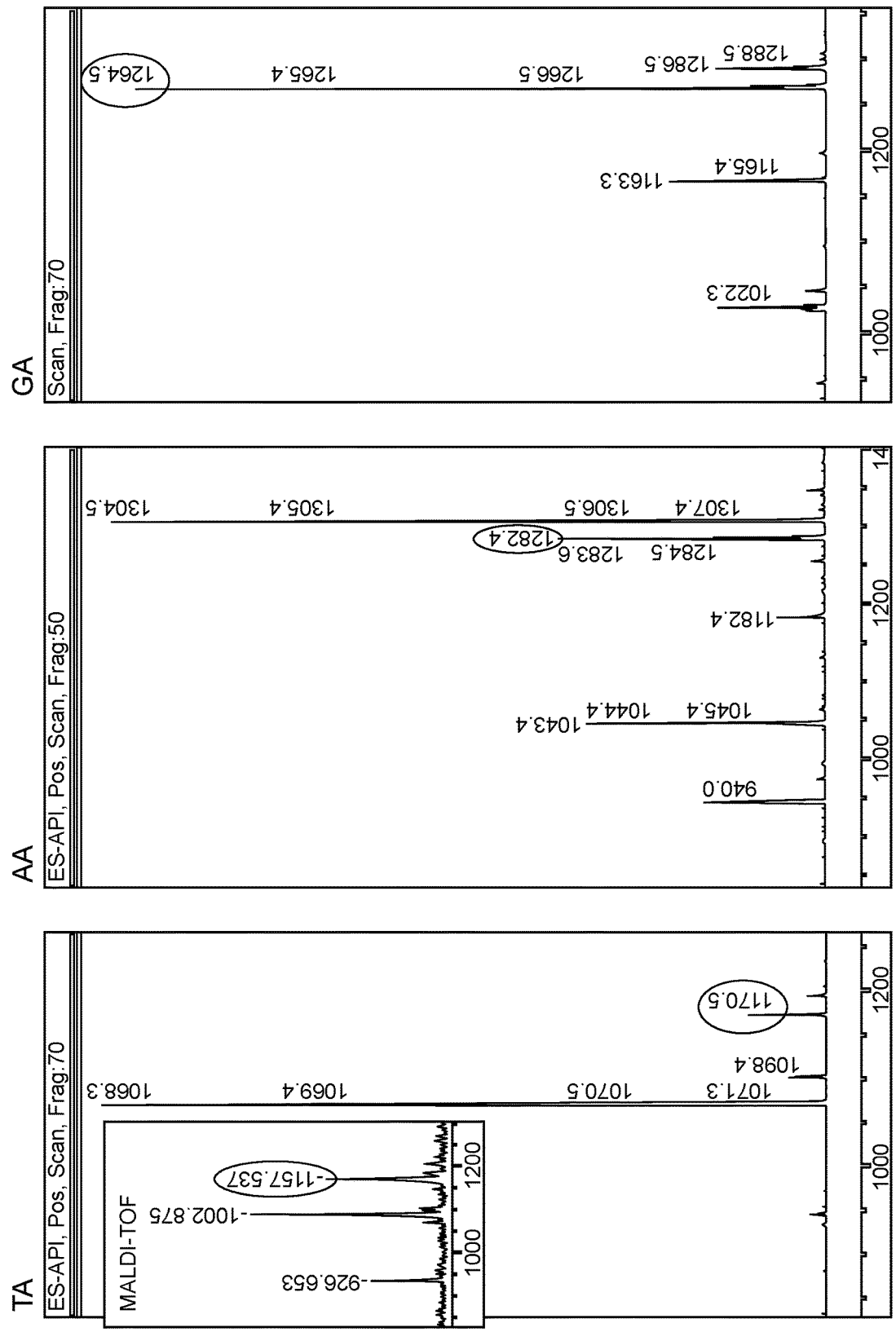

Exemplary lipid-modified oligonucleotides that may be prepared according to the subject methods include those compounds described in FIG. 1 (e.g., FIGS. 1A-1DD) of U.S. Application US20120329858 to Gryaznov et al "Modified oligonucleotides for telomerase inhibition", the disclosure of which is herein incorporated by reference in its entirety.

In certain embodiments, the composition includes a compound described by the structure:

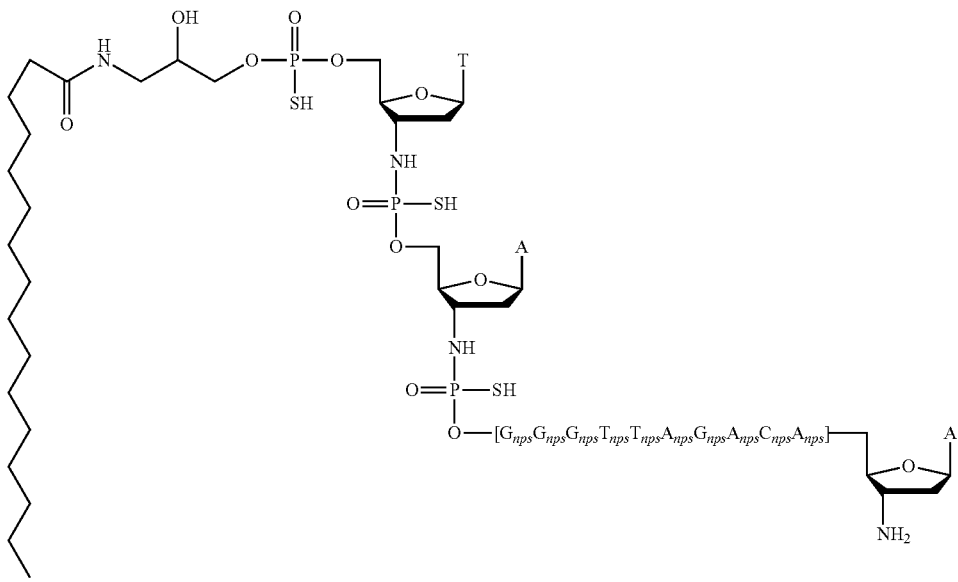

where "nps" represents a thiophosphoramidate linkage (e.g., —NH—P(=O)(SH)—O—), connecting the 3'-carbon of one nucleoside to the 5'-carbon of the adjacent nucleoside.

It is understood that all embodiments referring to a compound are also applicable to the salt forms of said compound.

In certain embodiments, the composition includes a compound described by the structure:

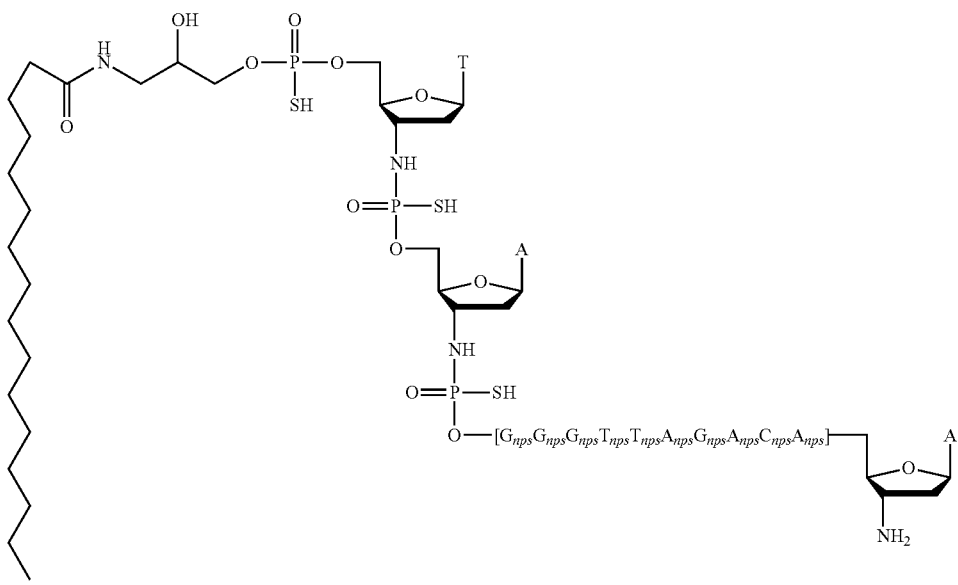

or a salt thereof;
where "nps" represents a thiophosphoramidate linkage (e.g., —NH—P(=O)(SH)—O— or a tautomer thereof, or a salt thereof), connecting the 3'-carbon of one nucleoside to the 5'-carbon of the adjacent nucleoside. In certain embodiments, the composition includes a pharmaceutically acceptable salt of the compound. In certain instances, the composition includes a sodium salt of the compound. In certain embodiments, the composition includes a divalent cation salt of the compound, such as a magnesium salt of the compound. In certain embodiments, the composition includes a trivalent cation salt of the compound, such as an aluminium salt of the compound.

In certain embodiments, the composition includes an oligonucleotide described by the following structure, where each $M^{x+}$ is independently hydrogen or any convenient counterion of a salt, each x is independently 1, 2 or 3 and n is an integer from 5 to 13, such as 5, 6, 7, 8, 9, 10, 11, 12 or 13, such as n is 13:

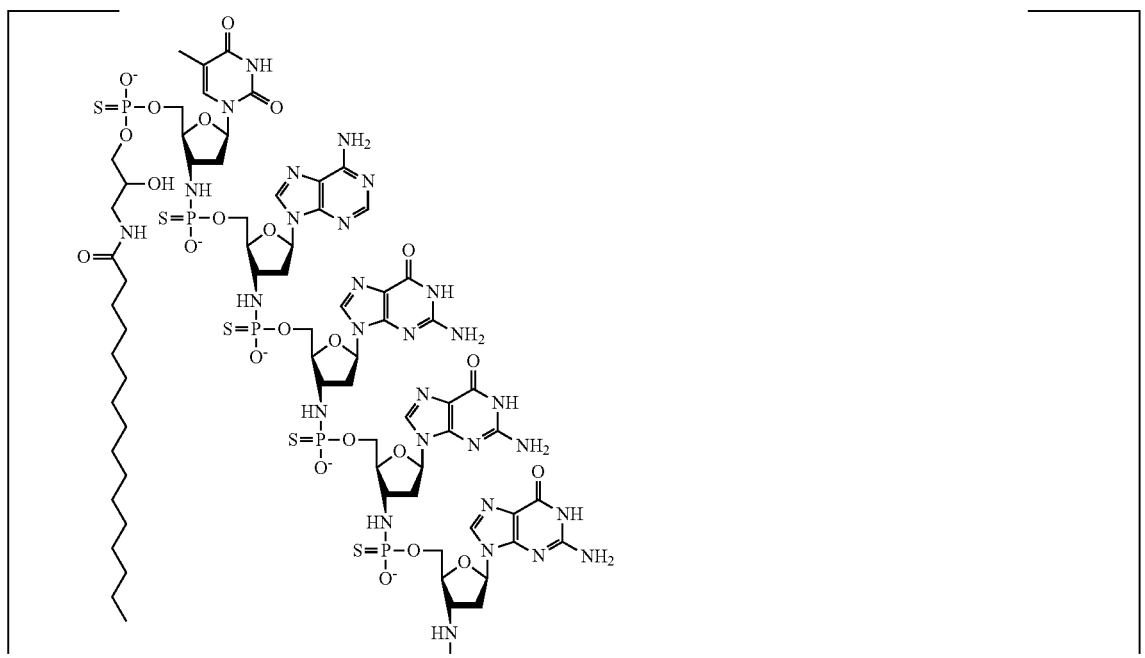
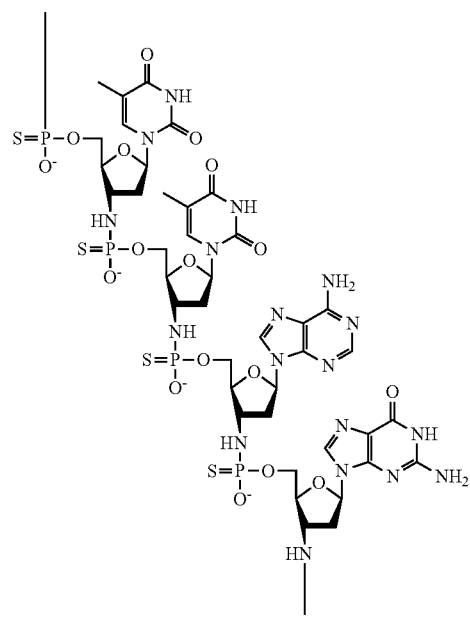

-continued
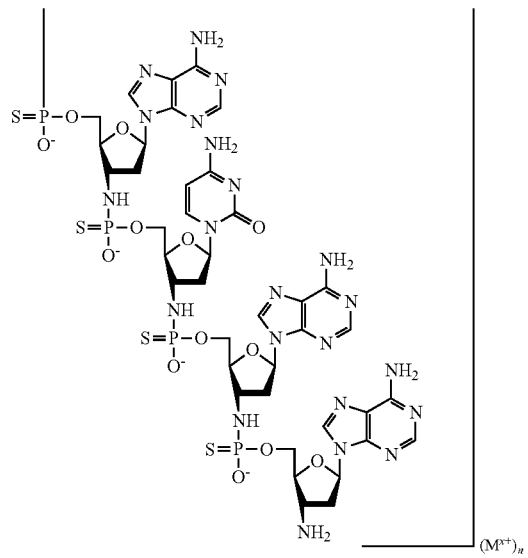
In certain instances, each x is 1. In certain instances, each x is independently 1 or 2. In certain instances, each x is independently 1 or 3. In certain instances, $M^{x+}$ is hydrogen.
In certain embodiments, the composition includes an oligonucleotide described by the following structure and may include any convenient cationic counterions of a salt:
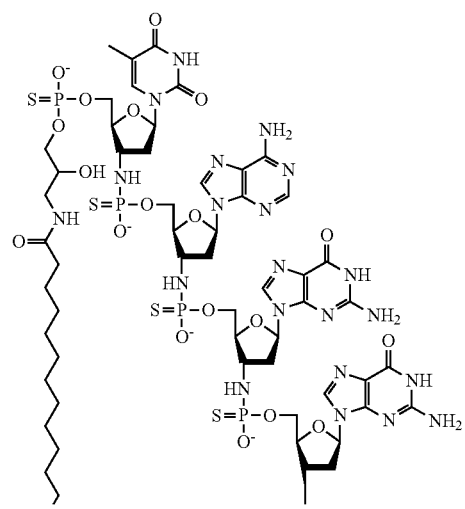

-continued
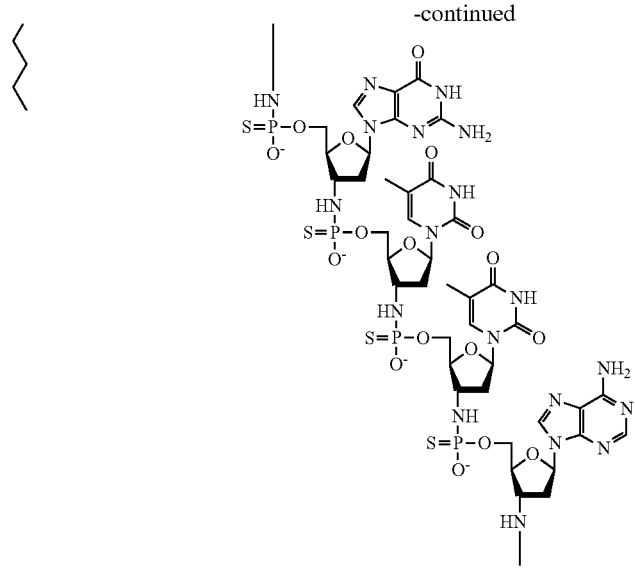
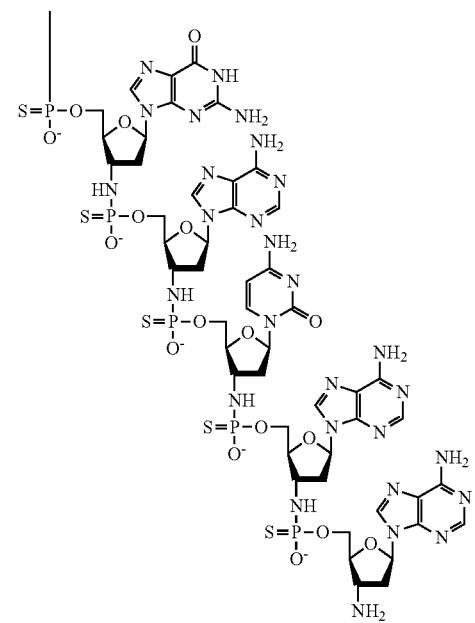

In certain embodiments, the composition includes a compound described by the structure:
Also provided are compound active pharmaceutical ingredient compositions including an oligonucleotide-containing
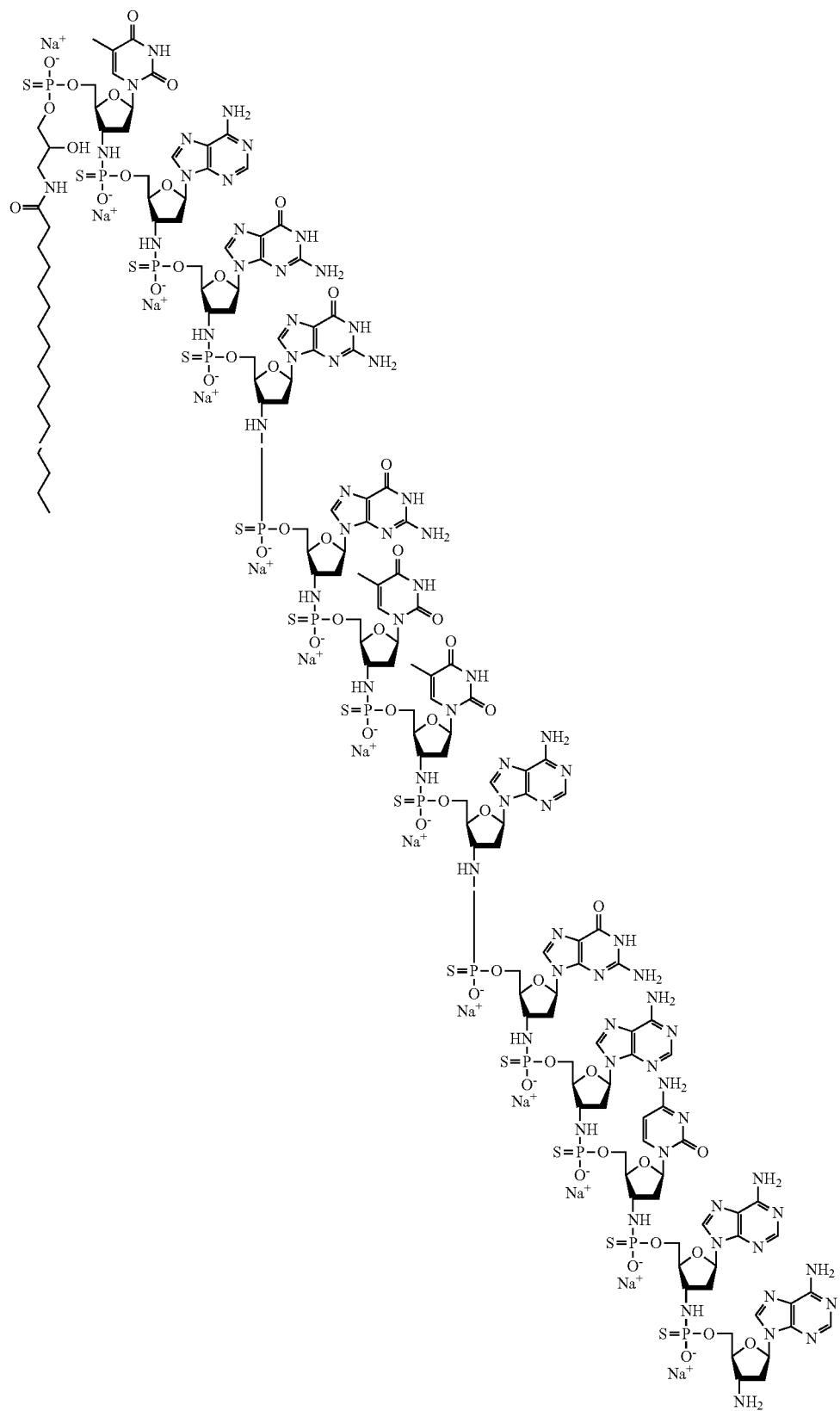

compound. As used herein, an active pharmaceutical ingredient refers to a composition that is produced using the subject methods of preparation, where the composition may optionally be subjected to one or more further purification steps post synthesis. In general, an active pharmaceutical ingredient is a composition suitable for formulation into a pharmaceutical composition. In some cases, the compound active pharmaceutical ingredient composition is not purified post synthesis, such that the oligonucleotide-containing components of the composition reflect those products produced during oligonucleotide synthesis.

In some embodiments, the compound active pharmaceutical ingredient has less than 9% by weight of a (N–1) product, wherein the compound comprises a polynucleotide having a sequence of 10 or more nucleoside subunits complementary to the RNA component of human telomerase, wherein at least two of the nucleoside subunits are joined by a N3'→P5' thiophosphoramidate or oxophosphoramidate inter-subunit linkage (e.g., as described herein).

In some embodiments, the compound active pharmaceutical ingredient has less than 9% by weight of a (N–1) product, wherein the compound or a pharmaceutically acceptable salt thereof comprises a polynucleotide having a sequence of 10 or more nucleoside subunits complementary to the RNA component of human telomerase, wherein at least two of the nucleoside subunits are joined by a N3→P5' thiophosphoramidate or oxophosphoramidate inter-subunit linkage (e.g., as described herein).

In some embodiments of the compound active pharmaceutical ingredient, the nucleoside subunits complementary to the RNA component of human telomerase are all joined by N3'→P5' thiophosphoramidate inter-subunit linkages.

In some embodiments of the compound active pharmaceutical ingredient, the N3'→P5' thiophosphoramidate inter-subunit linkage has the following structure:

3'-NH—P(S)(OR)—O-5' where R is selected from the group consisting of hydrogen, an alkyl, a substituted alkyl, an aryl, a substituted aryl and a phosphate protecting group. When R is selected from the group consisting of hydrogen, an alkyl, a substituted alkyl, an aryl, a substituted aryl and a phosphate protecting group, it is understood that some of the inter-subunit linkages described by the formula above may also exist in a salt form. Such forms in so far as they may exist, are intended to be included within the scope of the present disclosure.

In some embodiments of the compound active pharmaceutical ingredient, the N3'→P5' thiophosphoramidate inter-subunit linkage has the following structure:

3'-NH—P(S)(OR)—O-5' where R is hydrogen. It is understood that for any of the compound active pharmaceutical ingredients described herein that include such an inter-subunit linkage, such compound active pharmaceutical ingredient may also include any convenient pharmaceutically acceptable salt forms of the linkage. As such, the inter-subunit linkage may be in a pharmaceutically acceptable salt form that includes any convenient counterion of the salt.

In some embodiments of the compound active pharmaceutical ingredient, the polynucleotide comprises between 10 and 50 contiguous nucleoside subunits complementary to the RNA component of human telomerase (e.g., as described herein).

In some embodiments of the compound active pharmaceutical ingredient, the polynucleotide comprises a sequence selected from the group consisting of: GTTAGGGTTAG (SEQ ID NO:4); TAGGGTTAGACAA (SEQ ID NO:3); and CAGTTAGGGTTAG (SEQ ID NO:5).

In some embodiments of the compound active pharmaceutical ingredient, the polynucleotide includes a 3'amino or a 3'-hydroxyl terminal group. In certain embodiments of the compound active pharmaceutical ingredient, the polynucleotide includes a 3'amino terminal group. In certain embodiments of the compound active pharmaceutical ingredient, the polynucleotide includes a 3'-hydroxyl terminal group.

In some embodiments of the compound active pharmaceutical ingredient, the compound has the structure:

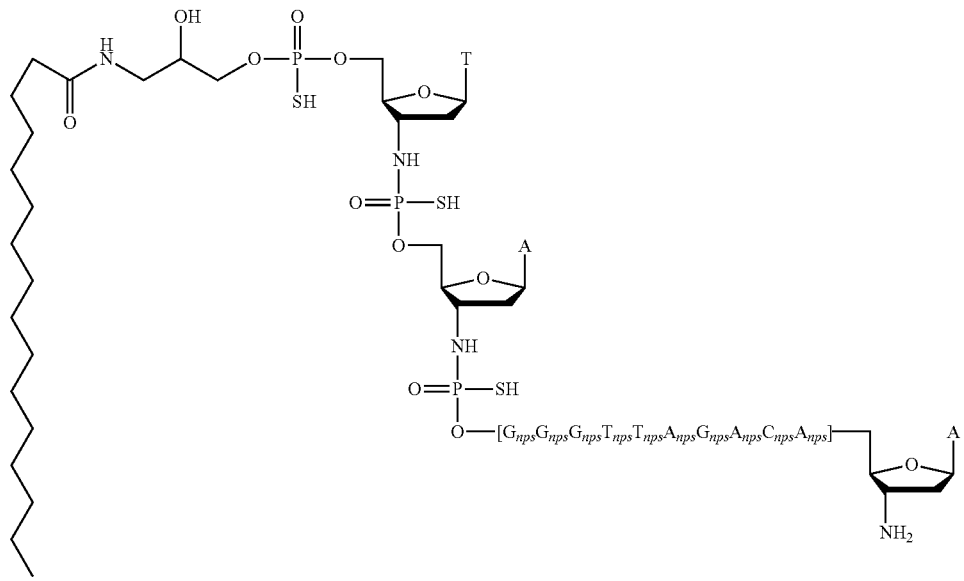

wherein "nps" represents a thiophosphoramidate linkage —NH—P(=O)(SH)—O—, connecting the 3'-carbon of one nucleoside to the 5'-carbon of the adjacent nucleoside.

It is understood that all embodiments referring to a compound active pharmaceutical ingredient are also applicable to the salt forms of said compound active pharmaceutical ingredient.

In some embodiments of the compound active pharmaceutical ingredient, the compound has the structure:

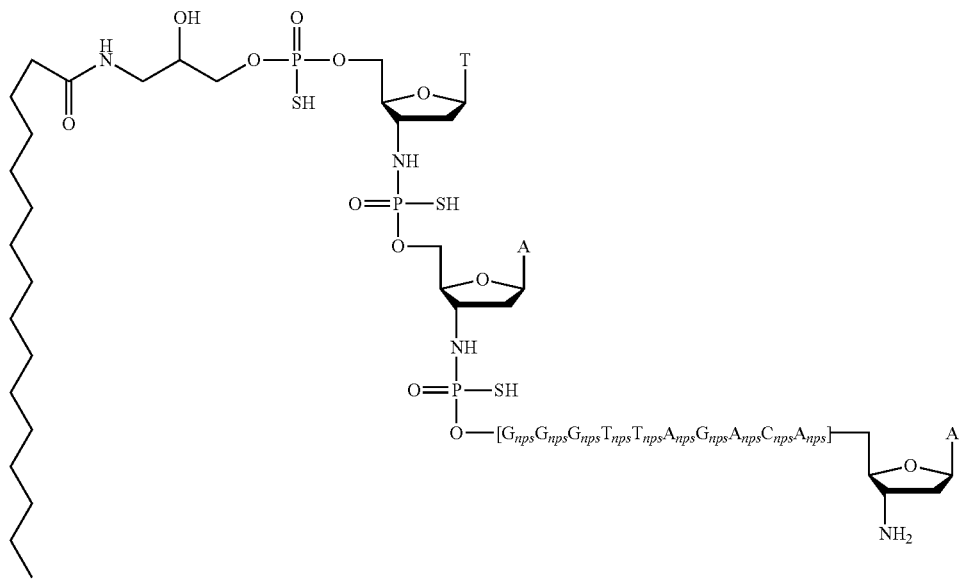

or a pharmaceutically acceptable salt thereof;

wherein "nps" represents a thiophosphoramidate linkage —NH—P(=O)(SH)—O— (or a tautomer thereof or a pharmaceutically acceptable salt thereof, as described herein), connecting the 3'-carbon of one nucleoside to the 5'-carbon of the adjacent nucleoside. In certain embodiments of the compound active pharmaceutical ingredient, the composition includes a sodium salt of the compound. In certain embodiments, the composition includes a divalent cation salt of the compound, such as a magnesium salt of the compound. In certain embodiments, the composition includes a trivalent cation salt of the compound, such as an aluminium salt of the compound.

In certain embodiments of the compound active pharmaceutical ingredient, the compound is described by the following structure, where each $M^{x+}$ is independently hydrogen or any convenient counterion of a salt, each x is independently 1, 2 or 3 and n is an integer from 5 to 13, such as 5, 6, 7, 8, 9, 10, 11, 12 or 13, such as n is 13:

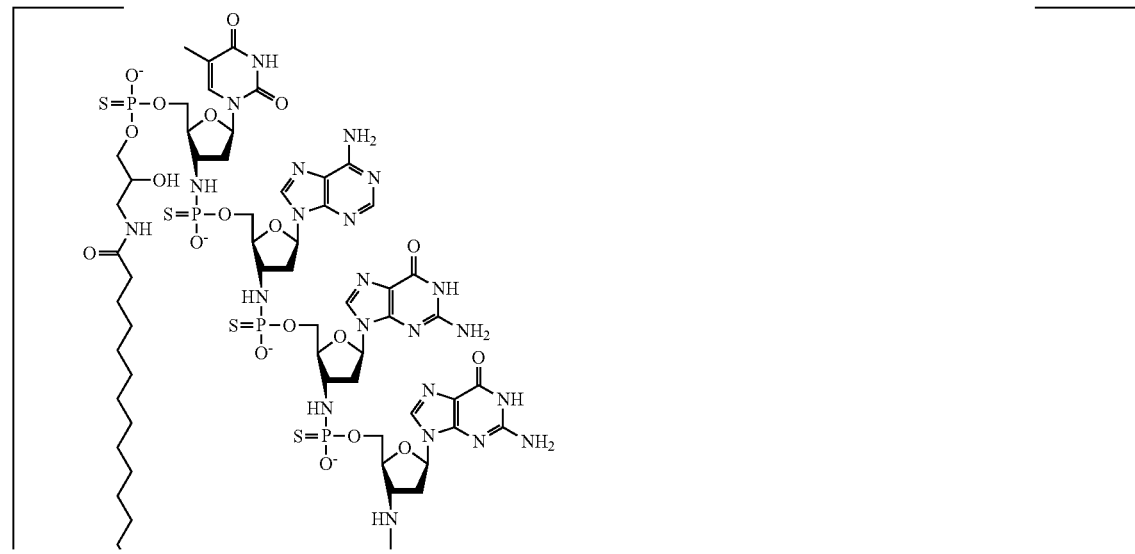

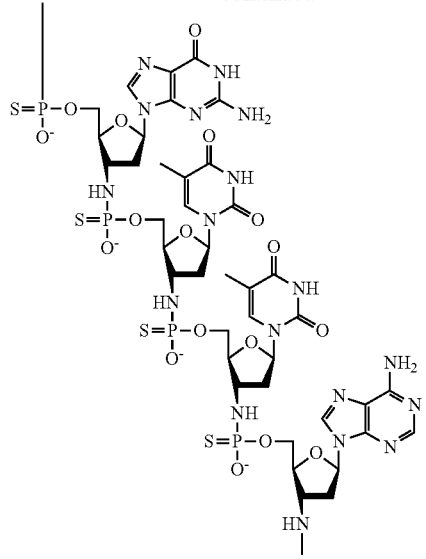
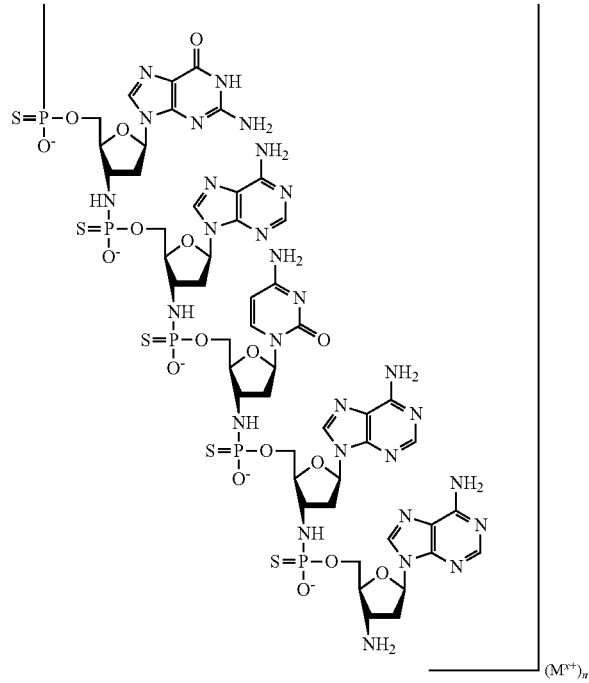
In certain instances, each x is 1. In certain instances, each x is independently 1 or 2. In certain instances, each x is independently 1 or 3. In certain instances, $M^{x+}$ is hydrogen.
In certain embodiments of the compound active pharmaceutical ingredient, the compound is described by the following structure and may include any convenient cationic counterions of a salt:

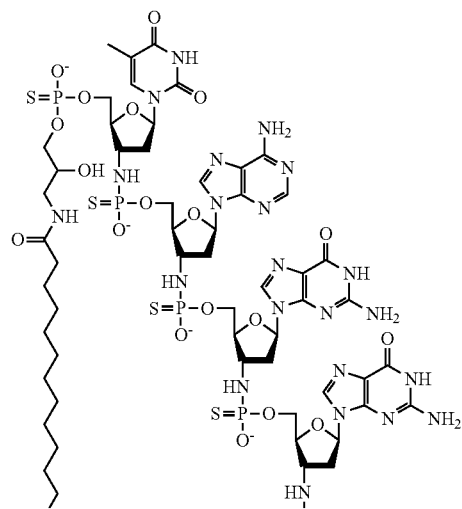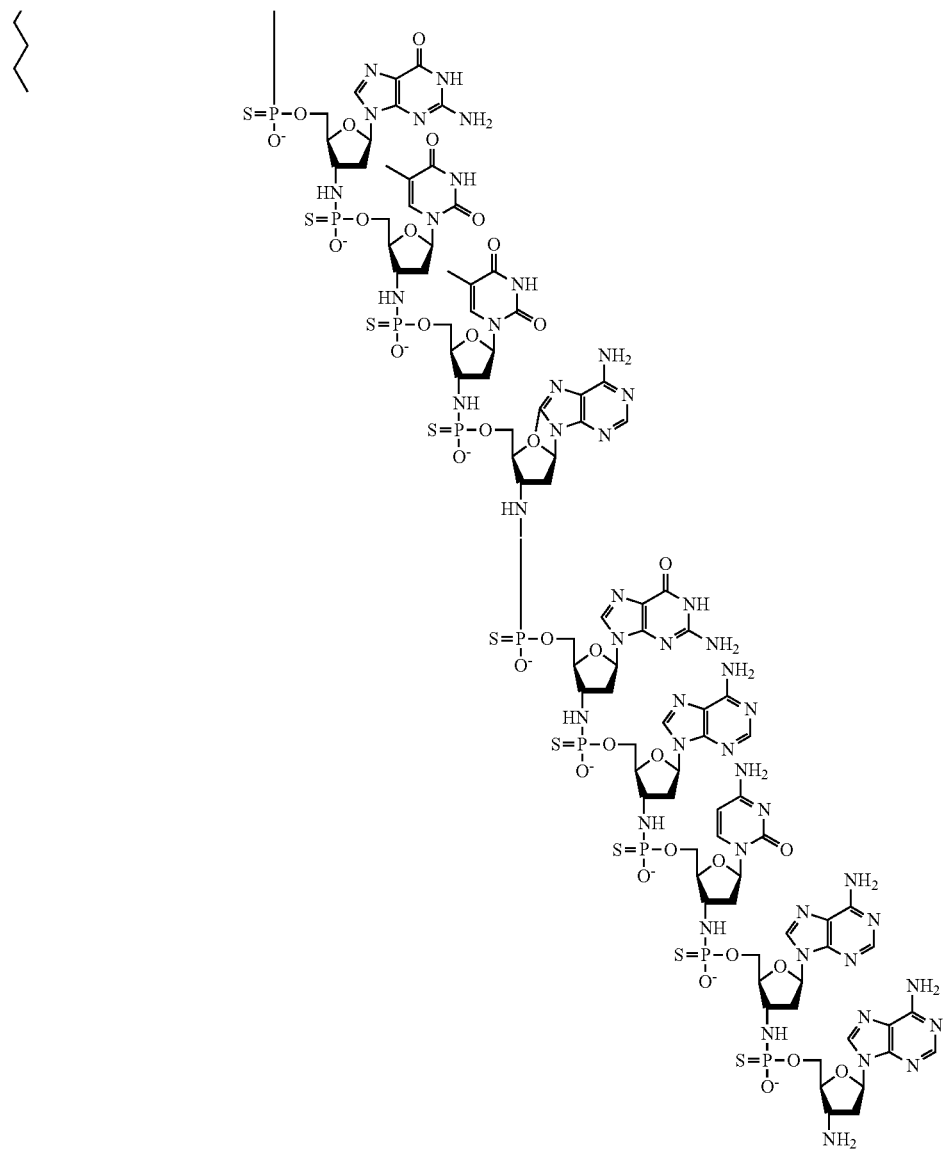

In some embodiments of the compound active pharmaceutical ingredient, the compound is described by the structure:

In certain embodiments, the compound active pharmaceutical ingredient has less that 5% by weight of the (N−1) product. In certain embodiments, the compound active phar-

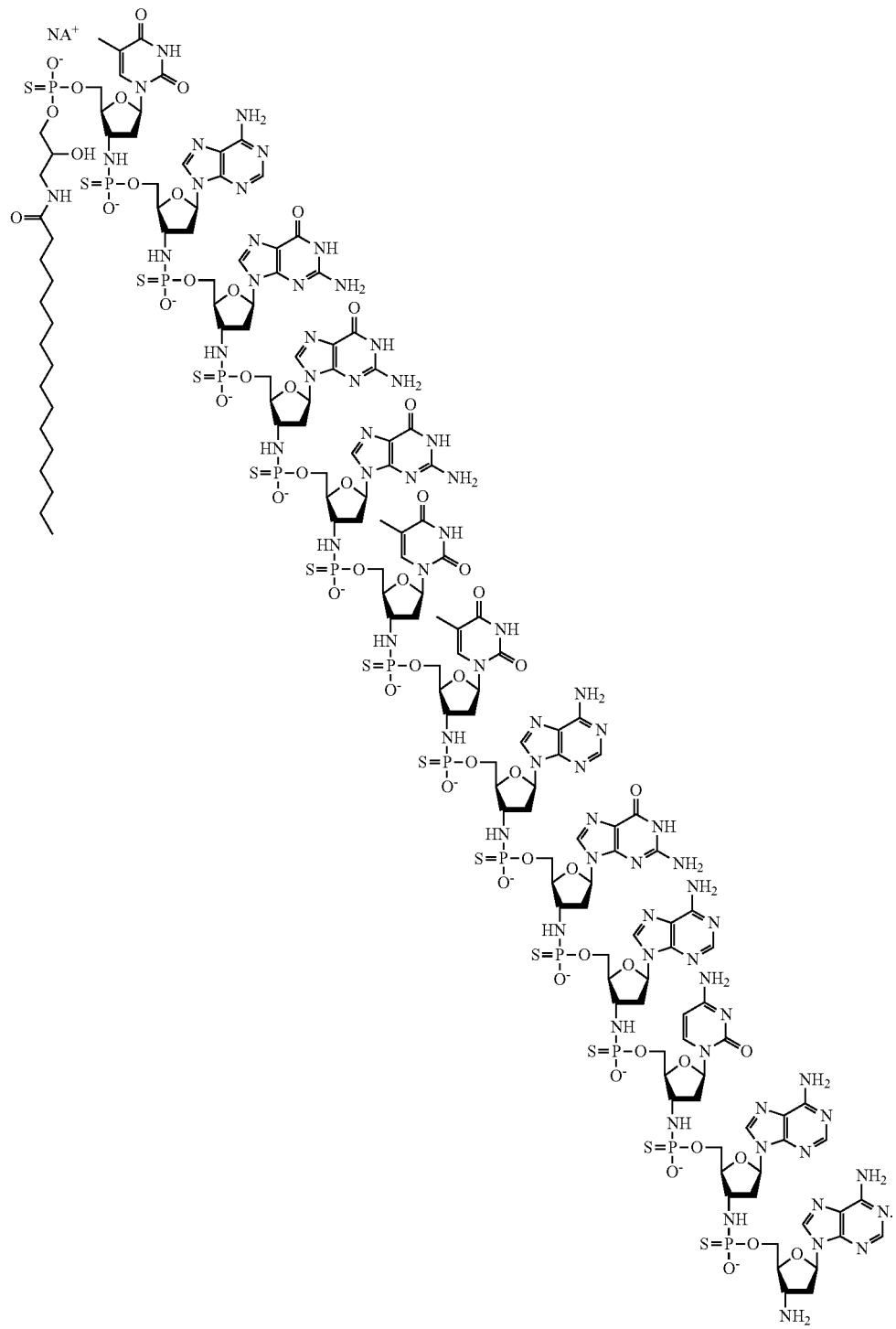

In some embodiments, the compound active pharmaceutical ingredient has less that 9% by weight of the (N−1) product, such as less than 8% by weight, less than 7% by weight, less than 6% by weight, less than 5% by weight, less than 4% by weight, less than 3% by weight, less than 2% by weight, or even less than 1% by weight of the (N−1) product.

maceutical ingredient has less that 2% by weight of the (N−1) product.

In some embodiments, the active pharmaceutical ingredient has less that 9% of any (N−x) product, such as less than 8% by weight, less than 7% by weight, less than 6% by weight, less than 5% by weight, less than 4% by weight, less than 3% by weight, less than 2% by weight, or even less than 1% by weight of any (N−x) product.

In some embodiments, the compound active pharmaceutical ingredient has less that 9% by weight in total of (N−x) polynucleotide-containing products, such as less than 8% by weight, less than 7% by weight, less than 6% by weight, less than 5% by weight, less than 4% by weight, less than 3% by weight, less than 2% by weight, or even less than 1% by weight in total of (N−x) polynucleotide-containing products.

In some embodiments, the compound active pharmaceutical ingredient has the following profile of (N−x) polynucleotide-containing products:

less that 1 part in 4 by weight of a (N−1) product relative to the N product; and at least 10 parts in 100 by weight of (N−2) and (N−3) products relative to the N product.

Formulations

Also provided are pharmaceutical compositions that include an oligonucleotide composition (e.g., as described herein). The oligonucleotide compositions (e.g., as described herein) can also be formulated as a pharmaceutical composition for inhibition of transcription or translation in a cell in a disease condition related to overexpression of the target gene.

In some embodiments, the pharmaceutical composition includes an oligonucleotide composition (e.g., as described herein) formulated in a pharmaceutically acceptable excipient. In certain embodiments, the oligonucleotide composition is a compound active pharmaceutical ingredient having less than 9% by weight of a (N−1) product, wherein the compound comprises a polynucleotide having a sequence of 10 or more nucleoside subunits complementary to the RNA component of human telomerase, wherein at least two of the nucleoside subunits are joined by a N3'→P5' thiophosphoramidate inter-subunit linkage.

The present invention provides compounds that can specifically and potently inhibit telomerase activity, and which may therefore be used to inhibit the proliferation of telomerase-positive cells, such as tumor cells. A very wide variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Cancers of interest include, but are not limited to, myelofibrosis, thrombocythemia, myelodysplasic syndrome and myelogenous leukemia.

The subject compounds can be used to treat hematologic malignancies and myeloproliferative disorders, including but not limited to, essential thrombocythemia (ET), polycythemia vera (PV) chronic myelogenous leukemia (CML), myelofibrosis (MF), chronic neutrophilic leukemia, chronic eosinophilic leukemia, and acute myelogenous leukemia (AML). The subject compounds can be used to treat myelodysplastic syndromes, which include such disease as refractory anemia, refractory anemia with excess blasts, refractory cytopenia with multilineage dysplasia, refractory cytopenia with unilineage dysplasia, and chronic myelomonocytic leukemia (CMML). The subject compounds can be used to treat hematological diseases, such as those described in PCT patent application No. PCT/US13/070437 filed Nov. 15, 2013, the disclosure of which is incorporated herein by reference in its entirety.

Accordingly, the compounds provided herein are broadly useful in treating a wide range of malignancies. More importantly, the compounds of the present invention can be effective in providing treatments that discriminate between malignant and normal cells to a high degree, avoiding many of the deleterious side-effects present with most current chemotherapeutic regimens which rely on agents that kill dividing cells indiscriminately. Moreover, the compounds of the invention are more potent than equivalent unconjugated oligonucleotides, which means that they can be administered at lower doses, providing enhanced safety and significant reductions in cost of treatment. One aspect of the invention therefore is a method of treating cancer in a patient, comprising administering to the patient a therapeutically effective dose of a compound of the present invention. Telomerase inhibitors, including compounds of the invention, may be employed in conjunction with other cancer treatment approaches, including surgical removal of primary tumors, chemotherapeutic agents and radiation treatment. Hence, the invention relates to compounds and compositions provided herein for use as a medicament. The invention also relates to compounds and compositions provided herein for use in treating or preventing any one of the malignancies mentioned hereinbefore.

For therapeutic application, a compound of the invention is formulated in a therapeutically effective amount with a pharmaceutically acceptable carrier. One or more invention compounds (for example, having different L' or O components) may be included in any given formulation. The pharmaceutical carrier may be solid or liquid. Liquid carriers can be used in the preparation of solutions, emulsions, suspensions and pressurized compositions. The compounds are dissolved or suspended in a pharmaceutically acceptable liquid excipient. Suitable examples of liquid carriers for parenteral administration of the oligonucleotides preparations include water (which may contain additives, e.g., cellulose derivatives, preferably sodium carboxymethyl cellulose solution), phosphate buffered saline solution (PBS), alcohols (including monohydric alcohols and polyhydric alcohols, e.g., glycols) and their derivatives, and oils (e.g., fractionated coconut oil and arachis oil). The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators.

For parenteral administration of the compounds, the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. The oligonucleotides can also be administered intravascularly or via a vascular stent.

The liquid carrier for pressurized compositions can be a halogenated hydrocarbon or other pharmaceutically acceptable propellant. Such pressurized compositions may also be lipid encapsulated for delivery via inhalation. For administration by intranasal or intrabronchial inhalation or insufflation, the oligonucleotides may be formulated into an aqueous or partially aqueous solution, which can then be utilized in the form of an aerosol.

The compounds may be administered topically as a solution, cream, or lotion, by formulation with pharmaceutically acceptable vehicles containing the active compound.

The pharmaceutical compositions of this invention may be orally administered in any acceptable dosage including, but not limited to, formulations in capsules, tablets, powders or granules, and as suspensions or solutions in water or non-aqueous media. Pharmaceutical compositions and/or formulations comprising the oligonucleotides of the present invention may include carriers, lubricants, diluents, thickeners, flavoring agents, emulsifiers, dispersing aids or binders. In the case of tablets for oral use, carriers which are commonly used include lactose and corn starch. Lubricating agents, such as magnesium stearate, may also be added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

While the compounds of the invention have superior characteristics for cellular and tissue penetration, they may be formulated to provide even greater benefit, for example in liposome carriers. The use of liposomes to facilitate cellular uptake is described, for example, in U.S. Pat. Nos. 4,897,355 and 4,394,448. Numerous publications describe the formulation and preparation of liposomes. The compounds can also be formulated by mixing with additional penetration enhancers, such as unconjugated forms of the lipid moieties described above, including fatty acids and their derivatives. Examples include oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.).

Complex formulations comprising one or more penetration enhancing agents may be used. For example, bile salts may be used in combination with fatty acids to make complex formulations. Exemplary combinations include chenodeoxycholic acid (CDCA), generally used at concentrations of about 0.5 to 2%, combined with sodium caprate or sodium laurate, generally used at concentrations of about 0.5 to 5%.

Pharmaceutical compositions and/or formulations comprising the oligonucleotides of the present invention may also include chelating agents, surfactants and non-surfactants. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines). Surfactants include, for example, sodium lauryl sulfate, polyoxyethylene-9-lauryl ether and polyoxyethylene-20-cetyl ether; and perfluorochemical emulsions, such as FC-43. Non-surfactants include, for example, unsaturated cyclic ureas, 1-alkyl- and 1-alkenylazacyclo-alkanone derivatives, and non-steroidal anti-inflammatory agents such as diclofenac sodium, indomethacin and phenylbutazone.

Thus, in another aspect of the invention, there is provided a method of formulating a pharmaceutical composition, the method comprising providing a compound as described herein, and combining the compound with a pharmaceutically acceptable excipient. Preferably the compound is provided at pharmaceutical purity, as defined below. The method may further comprise adding to the compound, either before or after the addition of the excipient, a penetration enhancing agent.

The pharmaceutical composition may comply with pharmaceutical purity standards. In some cases, for use as an active ingredient in a pharmaceutical preparation, a subject compound is purified away from reactive or potentially immunogenic components present in the mixture in which they are prepared.

The pharmaceutical composition may be aliquoted and packaged in either single dose or multi-dose units. The dosage requirements for treatment with the oligonucleotide compound vary with the particular compositions employed, the route of administration, the severity of the symptoms presented, the form of the compound and the particular subject being treated.

Pharmaceutical compositions of the invention can be administered to a subject in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor-specific markers such as serum PSA), and improvement in quality of life (as determined by clinical assessment, e.g., Karnofsky score), increased time to progression, disease-free survival and overall survival.

The amount of compound per dose and the number of doses required to achieve such effects will vary depending on many factors including the disease indication, characteristics of the patient being treated and the mode of administration. In some instances, the formulation and route of administration will provide a local concentration at the disease site of between 1 µM and 1 nM of the compound.

In general, the compounds are administered at a concentration that affords effective results without causing any harmful or deleterious side effects. Such a concentration can be achieved by administration of either a single unit dose, or by the administration of the dose divided into convenient subunits at suitable intervals throughout the day.

Utility

The methods and compositions of the invention, e.g., as described above, find use in a variety of applications. Applications of interest include, but are not limited to: therapeutic applications, diagnostic applications, research applications, and screening applications, as reviewed in greater detail below.

The subject compounds find use in a variety of therapeutic applications. In some embodiments, the methods of producing an oligonucleotide are applied to prepare oligonucleotides that provide for a therapeutic benefit. The types of diseases which are treatable using the compositions of the present invention are limitless. For example, the compositions may be used for treatment of a number of genetic diseases. In some embodiments, the subject methods and compositions have antisense applications. In some embodiments, the subject methods and compositions have antigene applications. In certain embodiments, the subject methods and compositions have telomerase inhibition applications, such as those described in U.S. Pat. No. 6,835,826, and U.S. Publication 20120329858, the disclosures of which are herein incorporated by reference in their entirety.

The subject compounds and methods find use in a variety of diagnostic applications, including but not limited to, the development of clinical diagnostics, e.g., in vitro diagnostics or in vivo tumor imaging agents. Such applications are useful in diagnosing or confirming diagnosis of a disease condition, or susceptibility thereto. The methods are also

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, $4^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Synthesis of Imetelstat Sodium Using Dimeric Phosphoramidites.

Imetelstat sodium is synthesized using a solid support (Controlled pore glass or polymeric solid support) and monomer phosphoramidites such as $A^{Bz}$ or $A^{dmf}$, C, $G^{iBu}$ and T amidites in the following sequence:

5'R-TAGGGTTAGACAA-NH$_2$-3' (SEQ ID NO:3) where R=Lipid linker group

TABLE 2

Structure of the Amidites and Solid Support

| Abbreviated Name | Description | Structure |
|---|---|---|
| Amidite $A^{dmf}$ | 3'-Tritylamino-N$_6$-dimethylformamidino-2',3'-dideoxyadenosine-5'-(2-cyanoethyl)-N,N-diisopropyl Phosphoramidite | 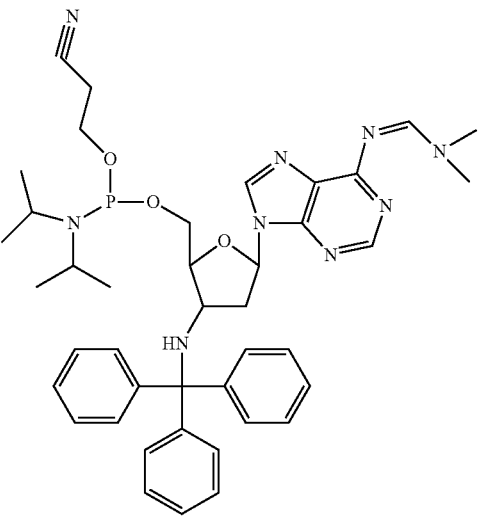 [SMILES: CC(C)N(C(C)C)P(OCCC#N)OCC1OC(n2cnc3c(/N=C\N(C)C)ncnc32)CC1NC(c1ccccc1)(c1ccccc1)c1ccccc1] |

TABLE 2-continued

Structure of the Amidites and Solid Support

| Abbreviated Name | Description | Structure |
|---|---|---|
| Amidite A$^{dmf}$ (MMT) | 3'-Monomethoxytritylamino-N$_6$-dimethylformamidino-2',3'-dideoxyadenosine-5'-(2-cyanoethyl)-N,N-diisopropyl Phosphoramidite | 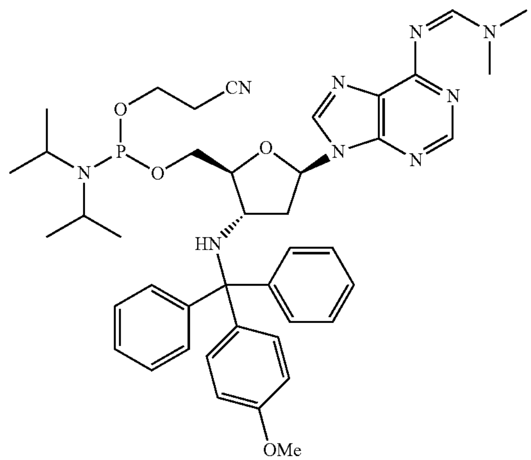 [SMILES: COc1ccc(C(N[C@H]2C[C@H](n3cnc4c(/N=C\N(C)C)ncnc43)O[C@@H]2COP(OCCC#N)N(C(C)C)C(C)C)(c2ccccc2)c2ccccc2)cc1] |
| Amidite A$^{dmf}$ (pixyl) | 3'-(Dimethyl-substituted Pixyl)amino-N$_6$-dimethylformamidino-2',3'-dideoxyadenosine-5'-(2-cyanoethyl)-N,N-diisopropyl Phosphoramidite | 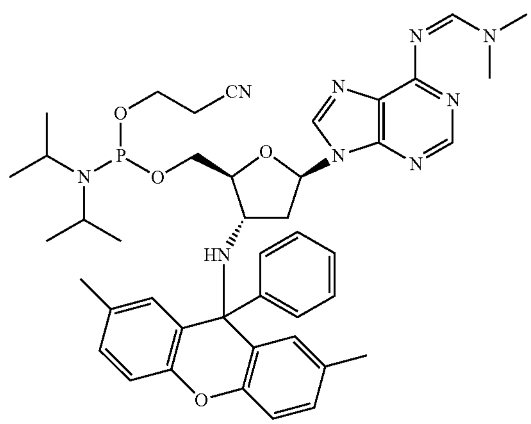 [SMILES: Cc1ccc2c(c1)C(N[C@H]1C[C@H](n3cnc4c(/N=C\N(C)C)ncnc43)O[C@@H]1COP(OCCC#N)N(C(C)C)C(C)C)(c1ccccc1)c1cc(C)ccc1O2] |
| Amidite A$^{dmf}$ (DMT) | 3'-Dimethoxytritylamino-N$_6$-dimethylformamidino-2',3'-dideoxyadenosine-5'-(2-cyanoethyl)-N,N-diisopropyl Phosphoramidite | 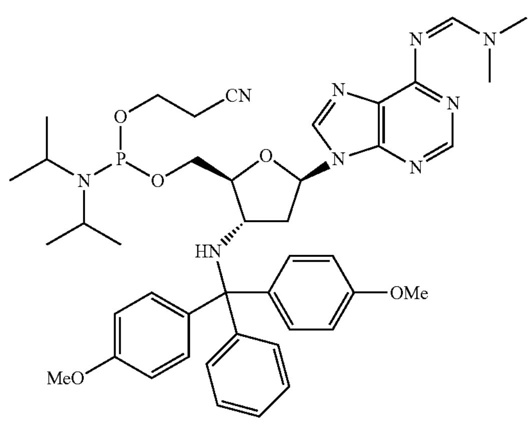 [SMILES: COc1ccc(C(N[C@H]2C[C@H](n3cnc4c(/N=C\N(C)C)ncnc43)O[C@@H]2COP(OCCC#N)N(C(C)C)C(C)C)(c2ccccc2)c2ccc(OC)cc2)cc1] |

TABLE 2-continued

Structure of the Amidites and Solid Support

| Abbreviated Name | Description | Structure |
|---|---|---|
| Amidite A$^{Bz}$ | 3'-Tritylamino-N$_6$-benzoyl-2',3'-dideoxyadenosine-5'-(2-cyanoethyl)-N,N-diisopropyl Phosphoramidite | 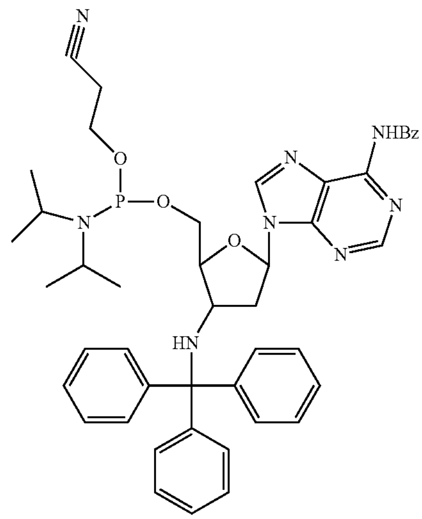 |
| Amidite C(Bz) | 3'-Tritylamino-N-benzoyl-2',3'-dideoxycytidine 5'-(2-cyanoethyl)-N,N-diisopropylphosphoramidite | 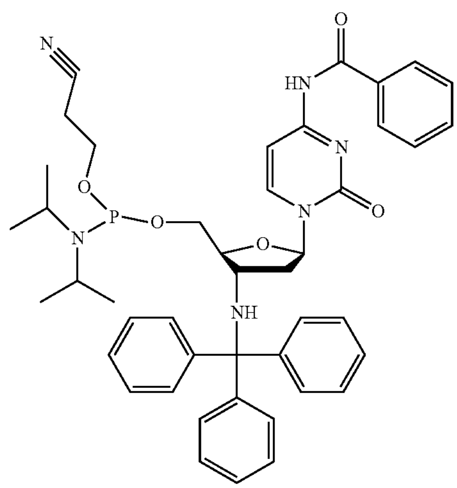 |
| Amidite G(iBu) | 3'-Tritylamino-N2-isobutyryl-2',3'-dideoxyguanosine-5'-(2-cyanoethyl)-N,N-diisopropyl Phosphoramidite | 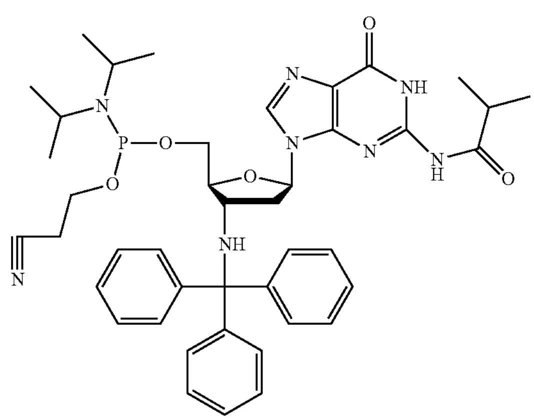 |

TABLE 2-continued

Structure of the Amidites and Solid Support

| Abbreviated Name | Description | Structure |
|---|---|---|
| Amidite T | 3'-Tritylamino-3'-deoxythymidine 5'-(2-cyanoethyl-N,N-diisopropylphosphoramidite | 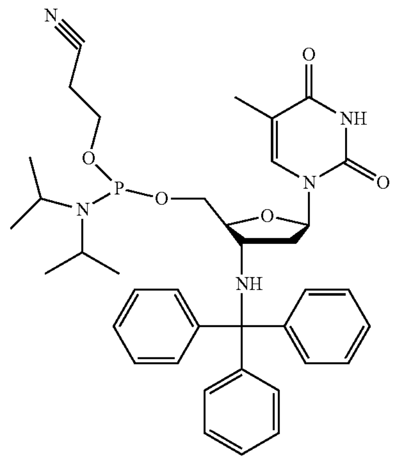 |
| Palmitoyl-aminoglycerol-solid support | 3-palmitoylamido-1-O-(4,4'-dimethoxytrityl)-2-O-succinyl propanediol Controlled Pore Glass Support | 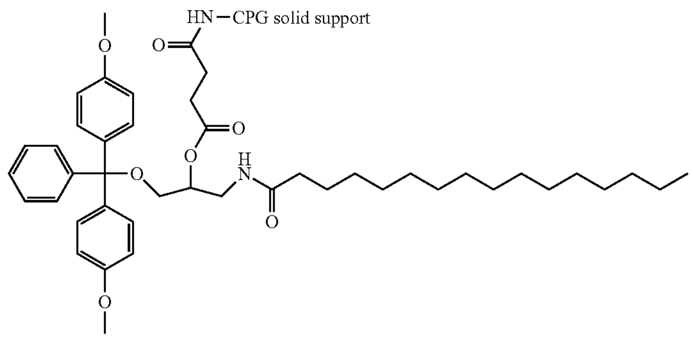 |
| Or | | |
| NittoPhaseHL Palmitoyl 400 Polymeric Solid Support | 3-palmitoylamido-1-O-(4,4'-dimethoxytrityl)-2-O-succinyl propanediol Polymeric Solid Support | 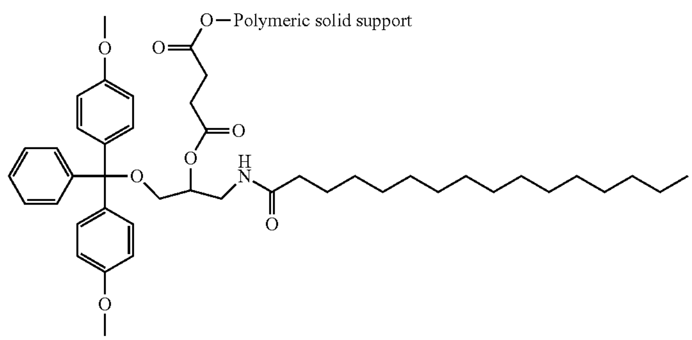 |

The imetelstat backbone is NPS which is similar to starting phosphoramidites and therefore the coupling efficiency is approximately 92%. Utilization of dimer phosphoramidites allows fewer coupling steps which can lead to higher yield and purity at the intermediate stage after synthesis. The following dimer phosphoramidites were prepared as shown below using a method as described in synthetic scheme 1:

TA, AA, GA, GG and GT.

The synthesis of the dimer phosphoramidites required three monomer amidates (4a to 4c, scheme 1) and three 5'-TBDMS-3' amino nucleoside intermediates (3a to 3c, scheme 1) for A, G and T nucleosides. TBDMS is tert-butyldimethylsilyl. The intermediates (3a to 3c, scheme 1) were prepared from two kinds of starting materials, 5'-OH-3'-NH-Tr-2'-deoxy-N-benzoyl adenosine (1a), 5'-OH-3'-NH-Tr-2'-deoxy-N-isobutyryl guanosine (1b), and 5'-OH-3'-amino-thymidine (2). Tr or Trt refer to trityl.

The 5'-hydroxyl group of 1a and 1b were protected with TBDMS groups using t-butyldimethylsilyl chloride and imidazole in DMF (N,N-dimethylformamide), and then the trityl groups at the 3'-amino positions were deprotected by the treatment with acetic acid in water. The resulting intermediates, 3a to 3c were coupled with the corresponding amidates, 4a to 4c, using benzylmercaptotetrazole (BMT) as an activator in dimethylformamide and the subsequent sulfurization (P III to P V) was performed using xanthane hydride and pyridine (scheme 1). In general, the sulfurization reaction was completed easily. The outcomes of the coupling reactions varied depending on moisture, reaction time, and equivalency of amidates. Anhydrous conditions using nitrogen or argon gas and a quick coupling reaction was desirable since a longer reaction time lead to more side products such as P (V) oxidation products. The P (III) intermediates of the dimer have different stabilities. The TA intermediate was stable enough to monitor the reaction completion by TLC and HPLC. Other P (III) intermediates were not stable enough to monitor the coupling reaction and reaction completion was checked after the sulfurization was completed (scheme 1). P(V) species are more stable for dimers AA, GA, GG and GT. For TA dimer (5e), 1.3 equivalent of amidate (4c) was used for the coupling and the other four dimers (5a~5d) required approximately 3 equivalent of amidates (4a and 4b) (scheme 1). Amidate monomers 4a-4c are prepared by adapting methods described in U.S. Pat. No. 5,859,233.

Scheme 1. Synthetic Scheme of Dimer Amidates (P-reagent is cyanoethoxy-bis(N,N, diisopropylamino)phosphine)

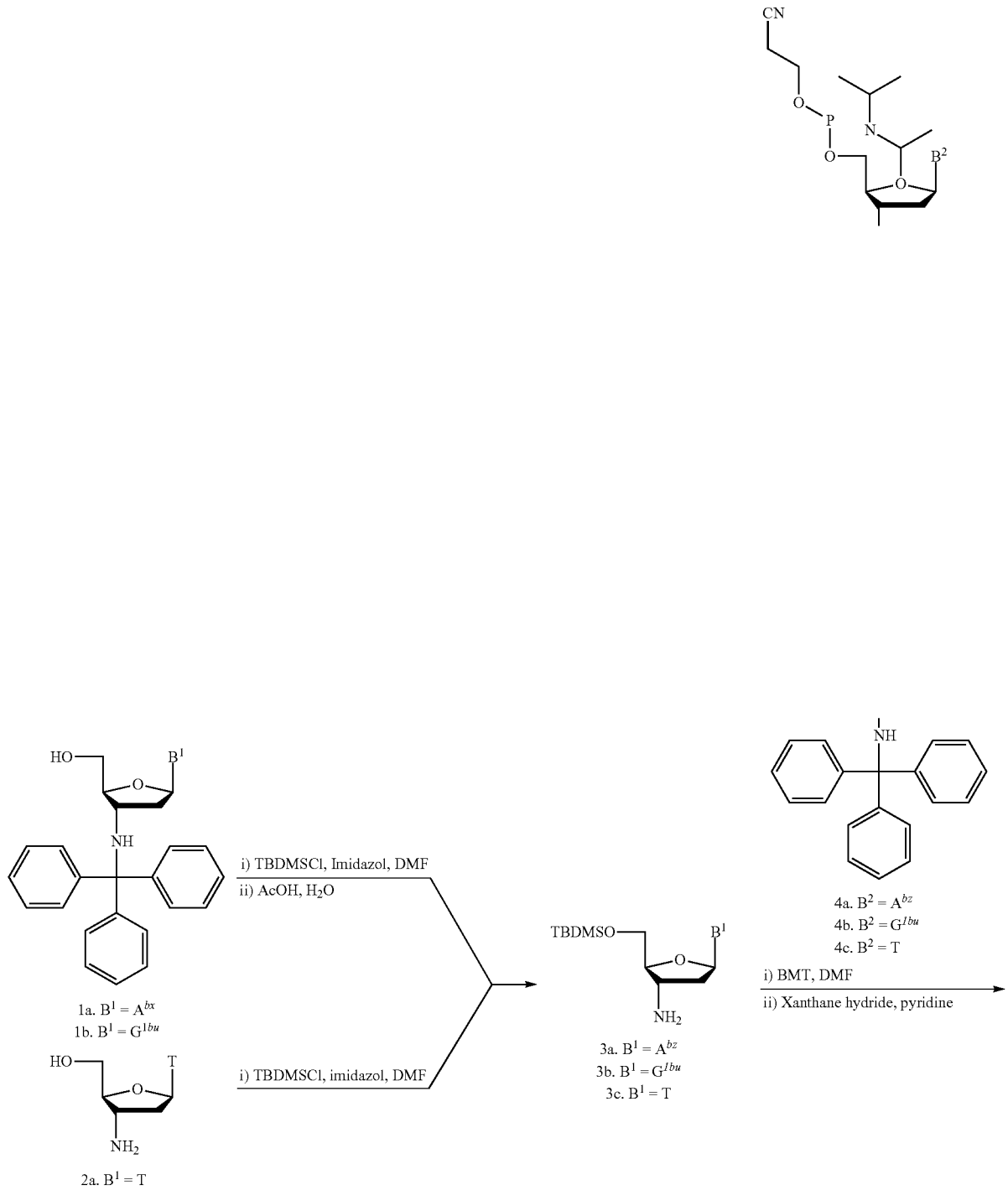

-continued

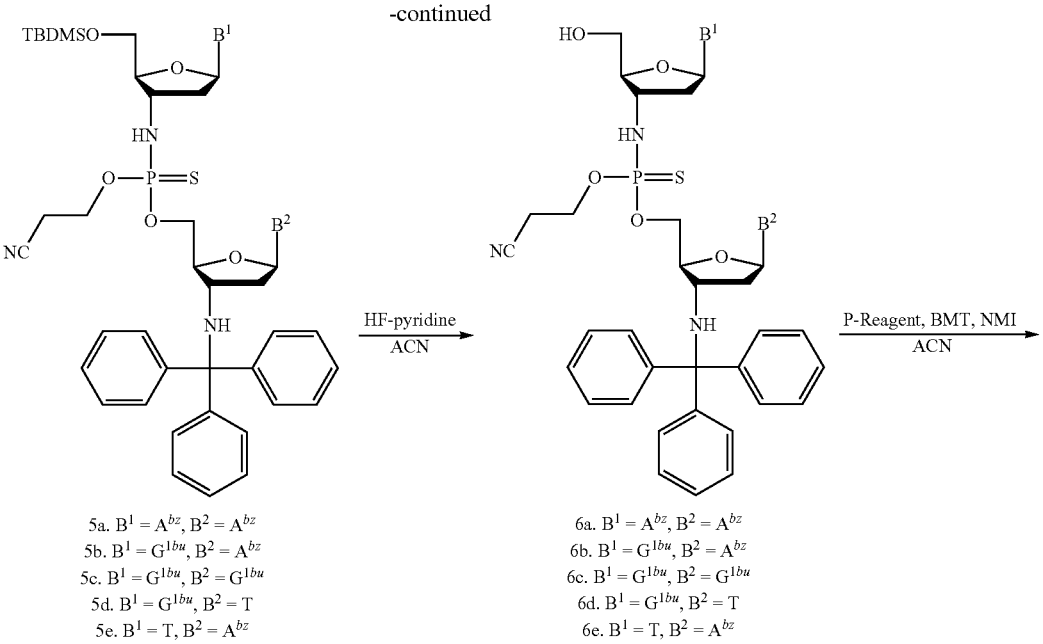

5a. $B^1 = A^{bz}, B^2 = A^{bz}$
5b. $B^1 = G^{ibu}, B^2 = A^{bz}$
5c. $B^1 = G^{ibu}, B^2 = G^{ibu}$
5d. $B^1 = G^{ibu}, B^2 = T$
5e. $B^1 = T, B^2 = A^{bz}$ 6a. $B^1 = A^{bz}, B^2 = A^{bz}$
6b. $B^1 = G^{ibu}, B^2 = A^{bz}$
6c. $B^1 = G^{ibu}, B^2 = G^{ibu}$
6d. $B^1 = G^{ibu}, B^2 = T$
6e. $B^1 = T, B^2 = A^{bz}$

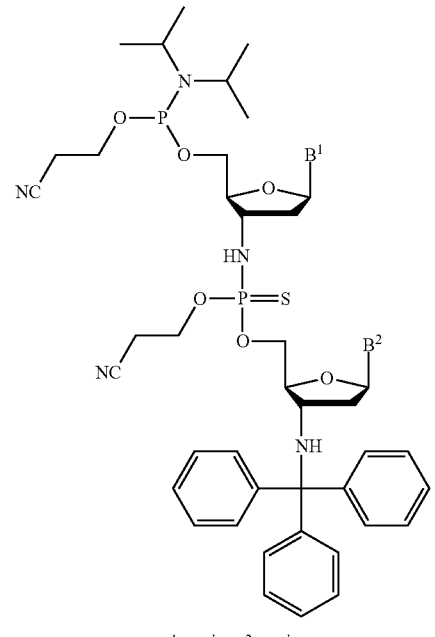

7a. $B^1 = A^{bz}, B^2 = A^{bz}$
7b. $B^1 = G^{ibu}, B^2 = A^{bz}$
7c. $B^1 = G^{ibu}, B^2 = G^{ibu}$
7d. $B^1 = G^{ibu}, B^2 = T$
7e. $B^1 = T, B^2 = A^{bz}$ The TBDMS protecting group at 5'-hydroxyl group was deprotected using HF•pyridine in acetonitrile and the final phosphitylation was performed with phosphitylating reagent in the presence of BMT and N-methylimidazole (NMJ) to make the dimer thiophsophoroamidates, 7a to 7e (Scheme 1). The final products (7) and three intermediates (3, 5, 6) were purified by column chromatography. The step and overall yields of reactions with quantities of final amidates obtained are listed in Table 3. Summary of analysis results for the five dimer amidates are shown in Table 4.

TABLE 3

Yields of Dimer Synthesis

| Dimer (Quantity) | 5'-TBDMS-3'-Amino Nucleoside | 5'-TBDMS-3'-NH-Tr-Dimer | 5'-OH-3'-NH-Tr Dimer | Dimer amidate | Overall yield (%) |
| --- | --- | --- | --- | --- | --- |
| TA (2.9 g) | 58% | 91% | 71% | 51% | 19.1% |
| AA (1.7 g) | 58% | 82% | 70% | 47% | 15.6% |

TABLE 3-continued

Yields of Dimer Synthesis

| Dimer (Quantity) | 5'-TBDMS-3'-Amino Nucleoside | 5'-TBDMS-3'-NH-Tr-Dimer | 5'-OH-3'-NH-Tr Dimer | Dimer amidate | Overall yield (%) |
|---|---|---|---|---|---|
| GA (3.4 g) | 58% | 77% | 60% | 55% | 14.7% |
| GG (1.9 g) | 58% | 67% | 57% | 38% | 8.4% |
| GT (1.8 g) | 58% | 99% | 42% | 38% | 9.2% |

TABLE 4

Summary of Dimer Analysis

| Dimer | Purity by HPLC | $^{31}$P-NMR | LCMS (Calc.) | Amount (g) |
|---|---|---|---|---|
| TA | 96.0% | 148.281(s), 148.193(s), 73.811(s), 73.723(s), 72.981(s), 72.592(s) | 1169.4 (1169.23) | 2.9 |
| AA | 95.8% | 148.262(m), 74.034(m), 72.774(d), 72.267(d) | 1282.5 (1282.35) | 1.7 |
| GG | 94.5% | 148.156(m), 74.244(s), 73.993(s), 72.912(s), 72.761(s) | 1268.5 (Na) (1246.32) | 1.9 |
| GT | 95.3% | 148.159(m), 73.993(s), 73.811(s), 73.295(s), 73.100(s) | 1151.4 (1151.22) | 1.8 |
| GA | 96.2% | 148.168(m), 148.011(s), 74.175(s), 73.942(s), 73.170(s), 72.906(s) | 1264.5 (1264.33) | 3.4 |

Synthesis Procedure of Dimer Thiophosphoroamidates

1) Preparation of 5'-TBDMS-3'-amino nucleoside (for Adenosine and Guanosine).

a) Dissolve 5'-OH-3'-NH-Tr-2'-deoxynucleoside (1.0 eq) and imidazole (5.0 eq) in DMF and heat to 60° C.

b) Add TBDMSCl (1.2 eq) to the heating solution then stir for 1 hr at 60° C.

c) Add saturated aqueous NaHCO₃ solution to reaction mixture then extract with ethyl acetate.

d) The organic layer is washed by saturated aqueous NaHCO₃ solution and brine solution.

e) Add anhydrous Na₂SO₄ to the separated organic layer for drying then filter.

f) The filtrate is concentrated.

g) Add 80% aqueous acetic acid solution to the concentrated reaction mixture then stir for 1 hour at ambient temperature.

h) Remove the product solid by filtration then add saturated aqueous NaHCO₃ solution to the filtrate then extract by ethyl acetate four times.

i) The organic layer is dried over anhydrous Na₂SO₄ then removed the solid by filtration.

j) The filtrate is concentrated then purified by column chromatography (Eluent: Ethyl acetate:Methanol=9:1→5:1).

k) 5'-TBDMS-3'-amino-2'-daoxynucleoside is obtained as white solid.

2) Preparation of 5'-TBDMS-3'-amino Nucleoside (for Thymidine)

a) Dissolve 5'-OH-3'-amino-2'-deoxynucleoside (1.0 eq) and imidazole (5.0 eq) in DMF and heat up to 60° C.

b) Add TBDMSCl (1.2 eq) to the heating solution then stirred for 1 hr at 60° C.

c) Add saturated aqueous NaHCO₃ solution to reaction mixture then extract with ethyl acetate four times.

d) Add anhydrous Na₂SO₄ to the organic layer for drying and filter.

e) The filtrate was concentrated.

f) The concentrated crude mixture is purified by column chromatography (Eluent: Ethyl acetate:Methanol=15:1→5:1).

g) 5'-TBDMS-3'-amino thymidine is obtained as a white solid.

3) Preparation of 5'-TBDMS-3'-NH-Tr Dimer a) To remove the moisture, 5'-TBDMS-3'-amino nucleoside (1.0 eq) and BMT (benzylmercaptotetrazole, 1.0-5.0 eq) are azeotroped by acetonitrile three times then dissolved in DMF at ambient temperature under N₂ atmosphere.

b) Add monomer amidate (3.0 eq) in DMF (using minimum amount to dissolve the monomer amidate) to the reaction solution by drop wise then stir for 1 hour at ambient temperature under nitrogen atmosphere. Monomer amidate is prepared according to methods described in U.S. Pat. No. 5,859,233.

c) Add xanthane hydride (2.0 eq) and pyridine (4.0 eq) to the reaction solution then stir for 1 hour at ambient temperature under nitrogen atmosphere.

d) Add saturated aqueous NaHCO₃ solution to reaction mixture then extract with ethyl acetate.

e) The aqueous layer is extracted with ethyl acetate.

f) The separated organic layers are combined and then washed by saturated aqueous NaHCO₃ solution and brine solution.

g) Add anhydrous Na₂SO₄ to the organic layer for drying and filter, then the filtrate is concentrated.

h) The concentrated crude mixture is purified by column chromatography (Eluent: ethyl acetate:methanol=1.5:1→EA only).

i) 5'-TBDMS-3'-NH-Tr dimer is obtained as a pale yellow solid.

4) Preparation of 5'-OH-3'-NH-Tr Dimer a) Dissolve 5'-TBDMS-3'-NH-Tr dimer (1.0 eq) in ACN (20 mL) under nitrogen atmosphere and then add HF-pyridine solution with stirring at ambient temperature for 1.5 hours.

b) Add saturated aqueous NaHCO₃ solution to reaction mixture then extract with ethyl acetate.

c) The separated organic layer is washed by saturated aqueous NaHCO₃ solution and brine solution.

d) Add anhydrous Na₂SO₄ to the organic layer for drying and filtering then the filtrate is concentrated.

e) The concentrated crude mixture is purified by column chromatography (Eluent: ethyl acetate, methanol, methylene chloride co-solvent)

f) 5'-OH-3'-NH-Tr dimer is obtained as a white solid.

5) Preparation of Dimer Phosphorothioamidate (Dimer Amidate)

A) To remove any moisture, 5'-Hydroxy-3'-NH-Tr dimer is azeotroped by acetonitrile three times then dissolved in ACN at ambient temperature under nitrogen atmosphere.

b) Add BMT (1.3 eq), NMI (N-Methyl imidazole, 0.3 eq) and phosphitylation reagent (2.0 eq) to the reaction solution then stir for 1 hour at ambient temperature.

c) Add saturated aqueous NaHCO$_3$ solution to reaction mixture then extract with ethyl acetate.

d) The separated organic layer is washed by brine solution.

e) Add anhydrous Na$_2$SO$_4$ to the organic layer for drying and filtering, then the filtrate is concentrated.

f) Dissolve concentrated reaction mixture in methylene chloride (10 mL) then add hexane to precipitate the solid.

g) Decant the upper solution layer to remove excess phosphitylation reagent. (Repeat decantation process 5 times).

h) The remaining solid is purified by column chromatography (Eluent: ethyl acetate, acetone, methylene chloride co-solvent)

i) Dimer is obtained as a white solid.

Imetelstat Synthesis Utilizing Dimer Amidates

Five dimer amidates were used in place of monomer amidates as the building blocks for the synthesis of imetelstat and the results were compared with the results obtained from the amidates of monomer. For the coupling of the C nucleoside into imetelstat, the monomer building clock was used as depicted in the sequence below. The synthesis was performed at a 140 µmole scale using an Akta Oligopilot 100.

5'R-<u>TA</u> <u>GG</u> <u>GT</u> <u>TA</u> <u>GA</u> C <u>AA</u>-NH$_2$ 3' (SEQ ID NO: 3)

Dimer amidates were used as building blocks to make imetelstat. Using the reagents and synthesis parameters listed in Tables 5A and 5B, the five dimer amidates (AA, TA, GG, GA, and GT) and one monomer amidate (C), as shown above, are coupled to make the imetelstat sequence on low-loading CPG (PALM 0051, 64.6 µmol/g). The coupling time is 500 sec and the 10 equivalency of the amidites were used. After the solid-phase synthesis, the support is treated with ethanolic ammonium solution (NH$_4$OH:EtOH=3:1 (v/v)) at 65° C. for 15 hours. The crude product is isolated by evaporation of solvents and analyzed by UV spectroscopy and HPLC.

TABLE 5

Exemplary Synthesis Parameters (A) and Reagent Composition (B) for oligonucleotide Synthesis.

A

| Step | Reagenz | Time | RPM | M |
|---|---|---|---|---|
| 1 | Wash | 3.5 | 300 | ☐ |
| 2 | Gas | 4.0 | 400 | |
| 3 | Debl | 3.4 | 250 | ☐ |
| 4 | Debl | 2.0 | 250 | ☐ |
| 5 | DWait | 60.0 | | |
| 6 | Wash | 12.0 | 350 | ☐ |
| 7 | Activ | 3.0 | 250 | |
| 8 | COUPL | | | |
| 9 | Wait | 300.0 | | |
| 10 | COUPL | | | |
| 11 | Activ | 1.3 | 150 | |
| 12 | Wait | 200.0 | | |
| 13 | Wash | 3.0 | 300 | ☐ |
| 14 | Oxid | 10.0 | 350 | |
| 15 | Wait | 300.0 | | |
| 16 | Oxid | 10.0 | 350 | |
| 17 | Wait | 300.0 | | |
| 18 | Wash | 6.0 | 350 | ☐ |
| 19 | CapA | 3.0 | 200 | |
| 20 | CapB | 1.5 | 150 | |
| 21 | DWait | 1.5 | | |
| 22 | CapA | 1.5 | 150 | |
| 23 | CapB | 1.5 | 150 | |
| 24 | DWait | 1.5 | | |
| 25 | Wash | 4.0 | 350 | ☐ |

B

| Reagent Name | Composition |
|---|---|
| Deblock | 5% DCA in toluene |
| Amidite | 0.2M in ACN |
| Activator | 0.5M ETT in ACN |
| Thiolation | 0.2M PADS in ACN:LTD = 1:1 |
| Cap A | 20% NMI on ACN |
| Cap B | IBUA:LTD:ACN = 1:1:8 |
| DEA | 20% DEA in ACN |

ACN is acetonitrile.
DCA is dichloroacetic acid.
PADS is phenylacetyl disulfide.
ETT is 5-Ethylthio-1H-Tetrazole Using an Akta Oligopilot 100, synthesis runs on a 140 µmole scale were conducted using the monomer block method and the dimer block method. The synthesis conditions for the synthesis runs were similar to those listed in Table 5A-B.

TABLE 6

Synthetic Parameters for 140 µmole scale Synthesis (AKTA Oligopilot 100)

| | Parameters | Imetelstat Synthesis using Monomers | Imetelstat Synthesis using Dimers |
|---|---|---|---|
| Deblock (5% DCA in toluene) | CT (min) | 3 min (2nd 6 min) | 3 min |
| | CV | 11.2 CV | |
| | Linear flow (cm/hr) | 450 cm/hr | |
| Coupling | Amidate | 0.1M, 2.5 eq (last 2: 3.0 eq) | 0.1M, 2.5 eq (last AA: 3.0 eq) |

TABLE 6-continued

Synthetic Parameters for 140 µmole scale Synthesis (AKTA Oligopilot 100)

| Parameters | | Imetelstat Synthesis using Monomers | Imetelstat Synthesis using Dimers |
|---|---|---|---|
| | Activator | 0.5M ETT (Amidate:Activator, 4:6) | |
| | 1st Coupling | double coupling | |
| | CT for Flow through (min) | 1.8 min | |
| | CT for Recycle (min) | 1.8 min (1st: 4 min) | |
| Thiolation | CT (min) | 5.27 min | |
| (0.1M PADS | CV | 3.5 CV | |
| in AN:LTD = 9:1) | Linear flow (cm/hr) | 80 cm/hr | |
| Capping | CT (min) | 1 min (1st: 2 min) | |
| (Cap A: 20% NMI in AN, | CV | 1 CV (1st: 2 CV) | |
| CapB: IBUA:LTD:AN = 1:1:8) | Linear flow (cm/hr) | 120 cm/hr | |
| DEA | CT (min) | 10 min | |
| (20% DEA in AN) | CV | 4.3 CV | |
| | Linear flow (cm/hr) | 52 cm/hr | |

Analysis of oligonucleotides by HPLC-MS showed that the FLP (full length product) purity was improved significantly when the five dimer blocks were used for synthesis, giving 72% purity by HPLC as summarized in Tables 7 and 8. The crude oligo prepared using the monomer blocks showed only 45% FLP purity. Further, the total OD (optical density) was increased by more than double from 5,299 to 11,623 affording the crude yield of 3.34 g/mmol. The (N–1) product level and the PO content were decreased to 2.4% from 11.2% and to 5% from 20%, respectively.

An advantage of using dimer blocks includes that the production time is shortened and the amounts of solvents used during the solid-phase synthesis are reduced.

TABLE 7

Analysis Result for 140 µmole Scale Synthesis

| Attributes | | Imetelstat Synthesis using Monomer Amidate | Imetelstat Synthesis using Dimer Amidate |
|---|---|---|---|
| HPLC | FLP | 44.4% | 74.0% |
| | Post-peak1 (N-1) product | 11.0% | 2.4% |
| UV | TOD | 5299 | 11623 |
| | Weight (mg) | 213 mg | 468 mg |
| | g/mmol | 1.52 | 3.34 |
| LC/MS | FLP | 70.3% | 71.9% |
| | n-117 | 3.3% | 16.4% |

TABLE 7-continued

Analysis Result for 140 µmole Scale Synthesis

| Attributes | Imetelstat Synthesis using Monomer Amidate | Imetelstat Synthesis using Dimer Amidate |
|---|---|---|
| n-133 | 6.5% | 6.7% |
| n-16 | 19.9% | 5.0% |

Figure 8:
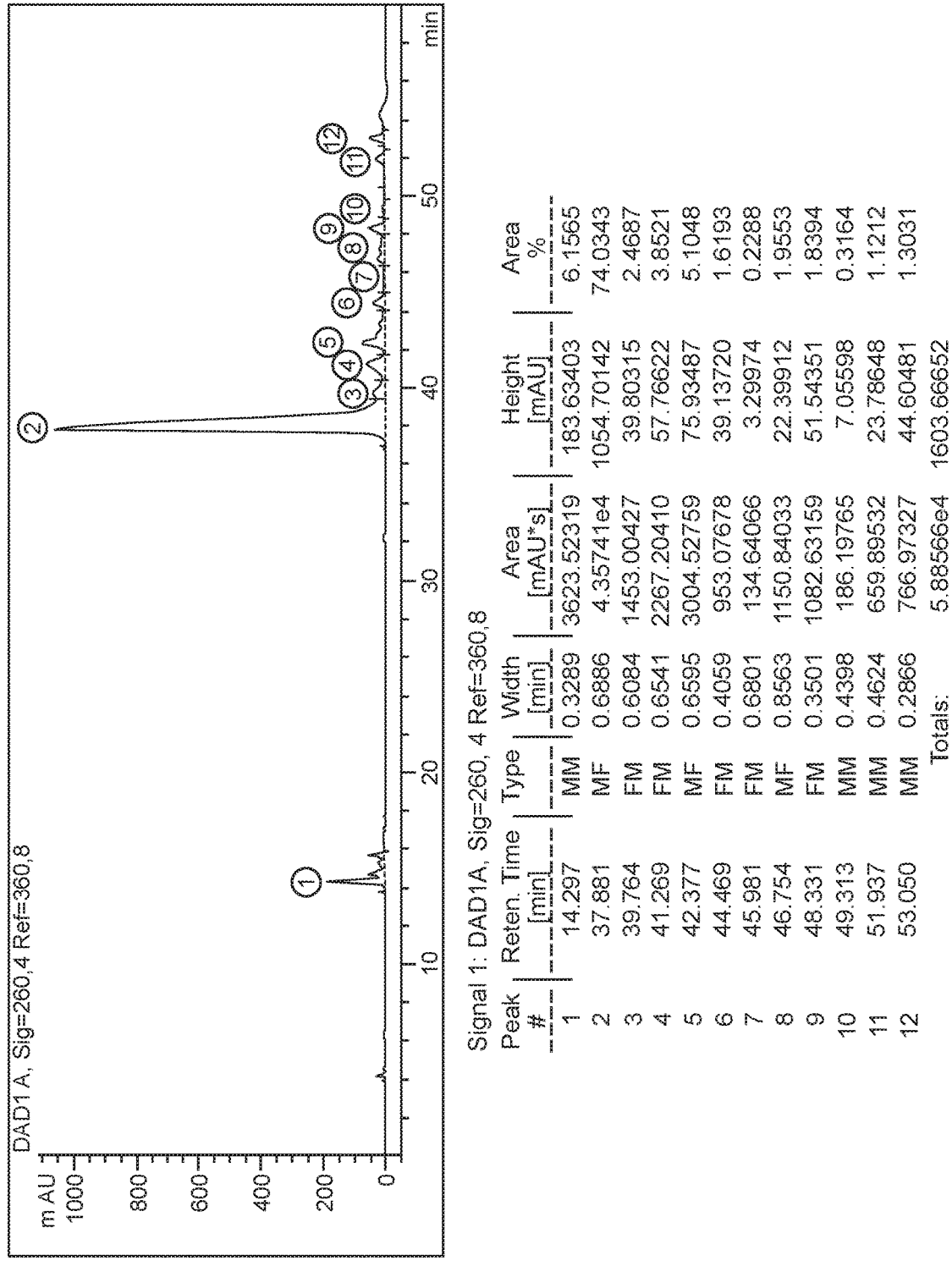
FIG. 8 shows an HPLC chromatogram of the product of a 140 µmole scale synthesis of imetelstat using a dimer block coupling strategy.

The synthesis of five dimer amidates was completed successfully with the yields of 9% to 19% from 5'-hydroxy-3'-amino nucleoside or 5'-hydroxy-3'-tritylamino nucleoside giving 1.7 gram to 3.4 gram. Optimization of reaction conditions for each step was not studied extensively. The dimers block syntheses of imetelstat were conducted on a 140 µmol scale and the results were compared with the data obtained from synthesis using monomer amidates. The dimer blocks strategy for preparation of imetelstat was shown to provide substantial improvements because the purity and yield were improved significantly, e.g., on a 140 µmol scale (HPLC Purity: dimer 74.0% (FIG. 8), monomer 44.4% (FIG. 7), Crude yield by TOD (total optical density): dimer 468 mg, monomer 213 mg). In addition a lower amount of npo linkage was generated since there were fewer coupling steps in the synthesis using dimers.

Coupling efficiency for the dimer (140 mole scale Synthesis) shows that the dimer synthesis had 96% coupling efficiency whereas the monomer synthesis is at 94%. Since there were only seven coupling for the dimer the FLP for dimer was at 71.6% which is close to the theoretically calculated Full Length Product at 72% and the monomer with 13 couplings reported a FLP of 45.6% vs the theoretically predicted at 44%.

TABLE 8

Analysis of Results for 140 µmole Scale Synthesis

| Products of monomer synthesis | Retention time (min) | % area monomer synthesis | Products of dimer synthesis | Retention time (min) | % area dimer synthesis |
|---|---|---|---|---|---|
| target | 38.2 | 44.4 | target | 37.9 | 74.0 |
| Post Peak 1 N-1 (N-G) | 39.8 | 11.0 | Post Peak 1 N-1 (N-C) | 39.8 | 2.5 |
| Post Peak 2 N-2 + iBu, N-2, N-G + Phenylacetyl | 41.2 | 6.3 | Post Peak 2 N-2 + iBu, N-2, N-G + Phenylacetyl | 41.3 | 3.9 |

TABLE 8-continued

Analysis of Results for 140 μmole Scale Synthesis

| Products of monomer synthesis | Retention time (min) | % area monomer synthesis | Products of dimer synthesis | Retention time (min) | % area dimer synthesis |
|---|---|---|---|---|---|
| Post Peak 3 N-2 + Phenylacetyl, N-3 (N-A-A-C) | 42.9 | 6.9 | Post Peak 3 N-2 + Phenylacetyl, N-3 (N-A-A-C) | 42.4 | 5.1 |
| Post Peak 4 N-3 + Phenylacetyl | 44.7 | 6.0 | Post Peak 4 N-3 + Phenylacetyl | 44.5 | 1.6 |
| Total non-target oligonucleotides | 39.8-54.7 | 49.5 | Total non-target oligonucleotides | 39.7-53.1 | 19.8 |

"+ Phenylacetyl" denotes a product derived from reaction with an oxidation reagent Imetelstat synthesis utilizing fewer coupling steps provides for both Full Length Product Purity and Yield that are substantially higher. Resolution of impurities provides easier purification of imetelstat where there are less amounts of minor products closely running near the main peak in HPLC to produce compositions having higher purity of imetelstat. This improvement is desirable for lower cost of goods for manufacture of imetelstat sodium, e.g., the cost of goods can be 30-40% less when implemented at manufacturing scale.

Scheme 2. Synthetic Scheme of GA Dimer Amidate

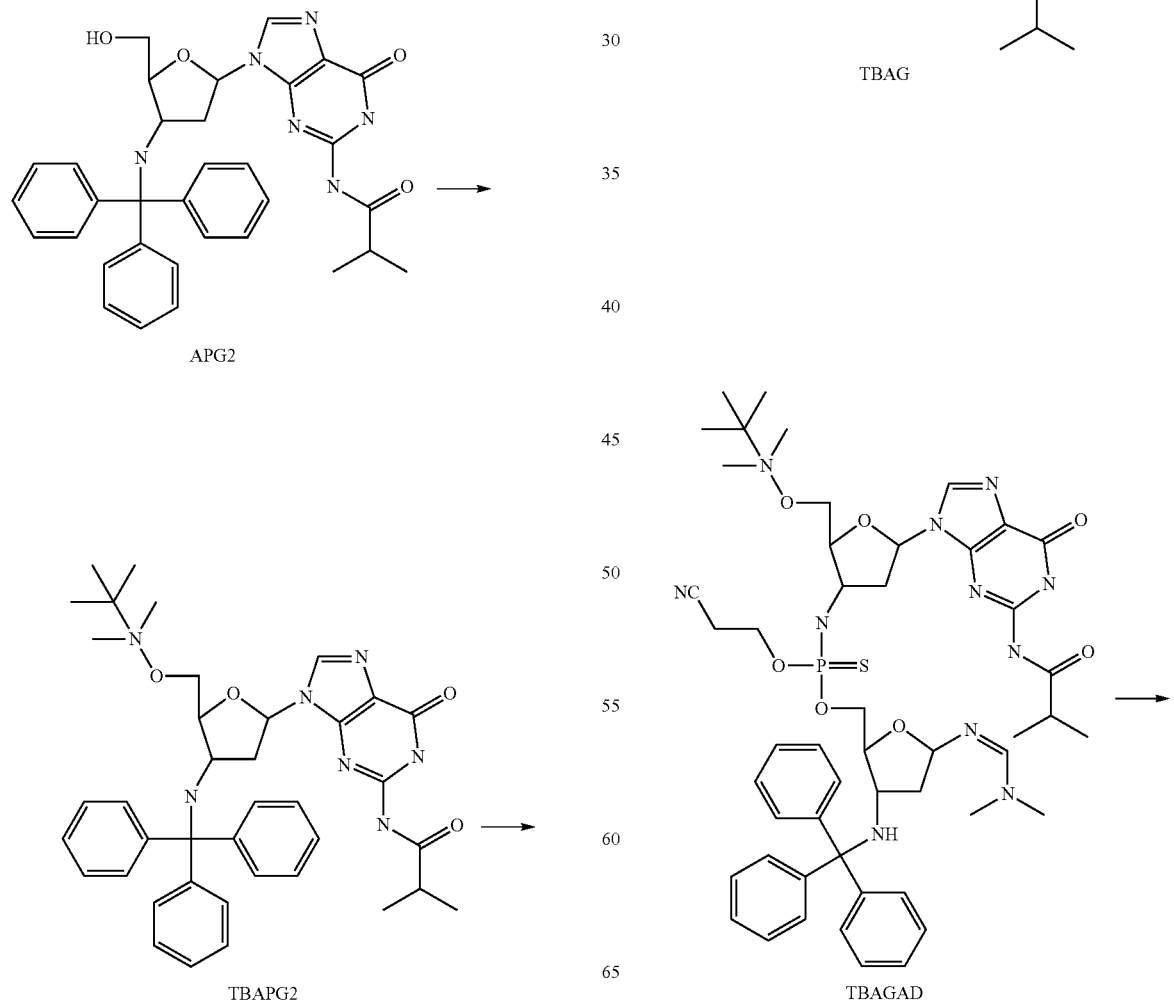

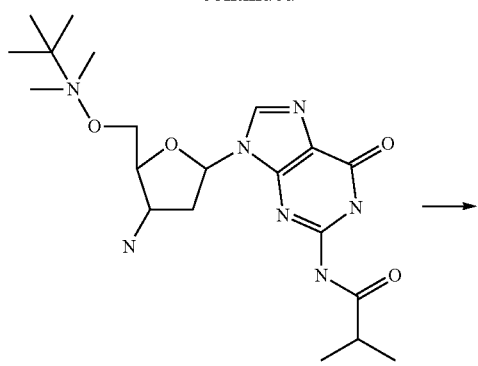

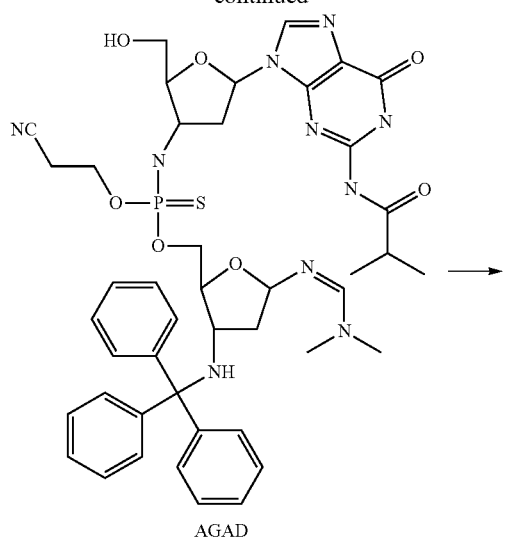
AGAD
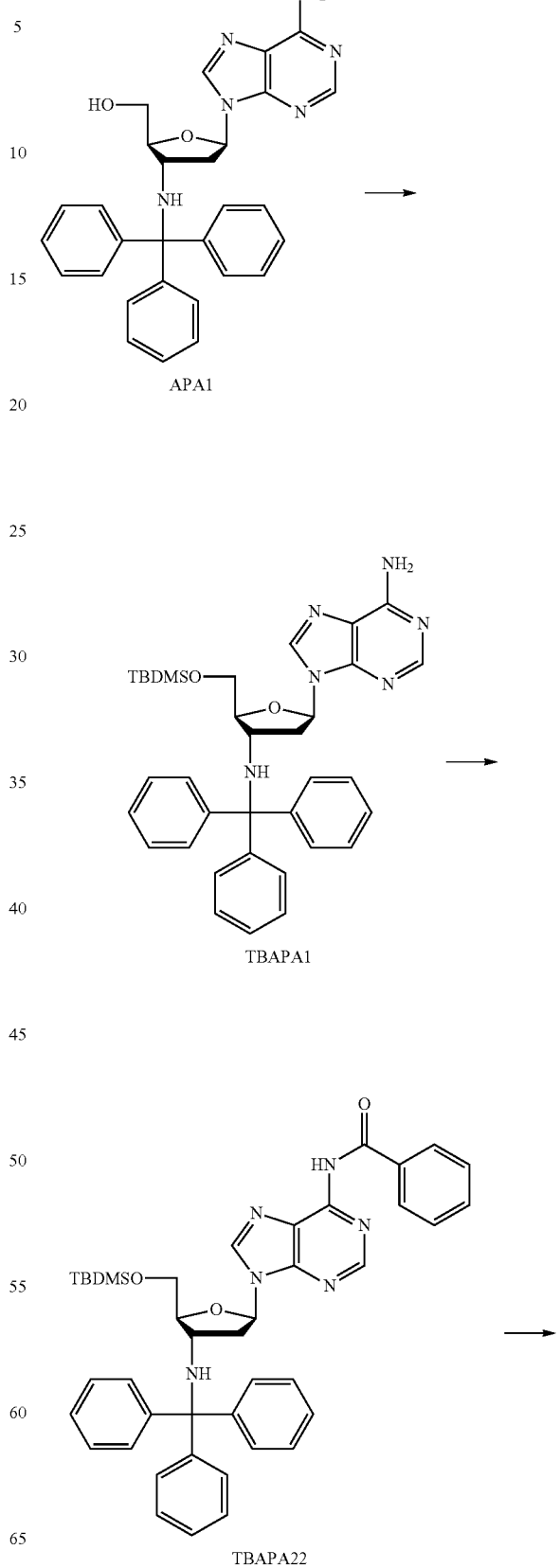
Scheme 3. Synthetic Scheme of AA Dimer Amidate
APGAD
85 g of TBAG was prepared from 300 g of APG2 according to the methods described herein via the steps shown in Scheme 2.

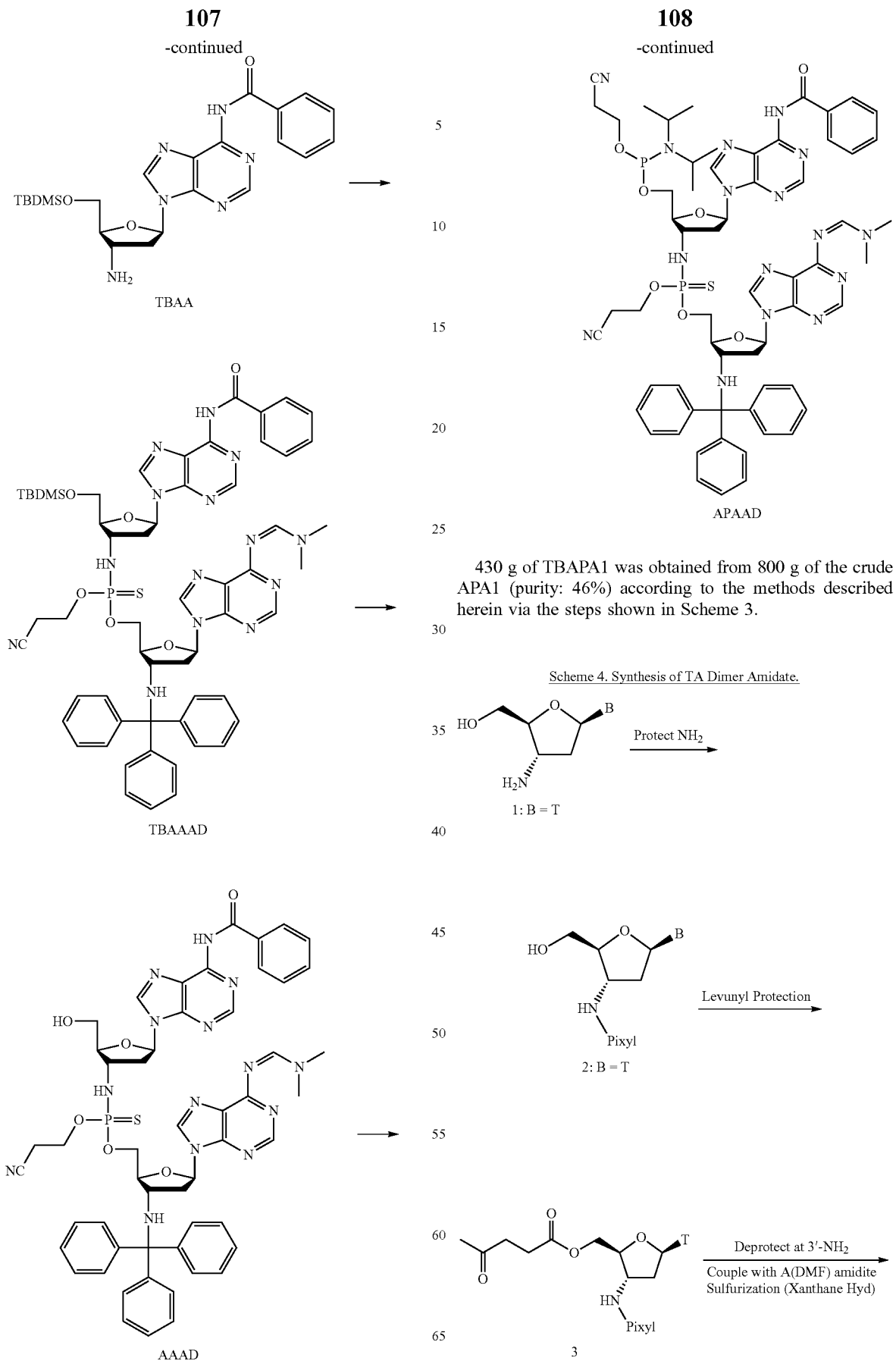
430 g of TBAPA1 was obtained from 800 g of the crude APA1 (purity: 46%) according to the methods described herein via the steps shown in Scheme 3.
Scheme 4. Synthesis of TA Dimer Amidate.

109
-continued

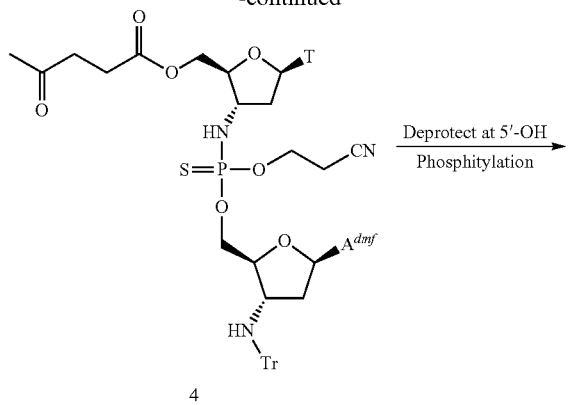

4

TA dimer amidate (5) has been prepared according to the methods described herein via the steps shown in Scheme 4 at scales of synthesis from 100 mg to 1 g.

110

Scheme 5. Coupling and Sulfurization during Dimer Amidate synthesis

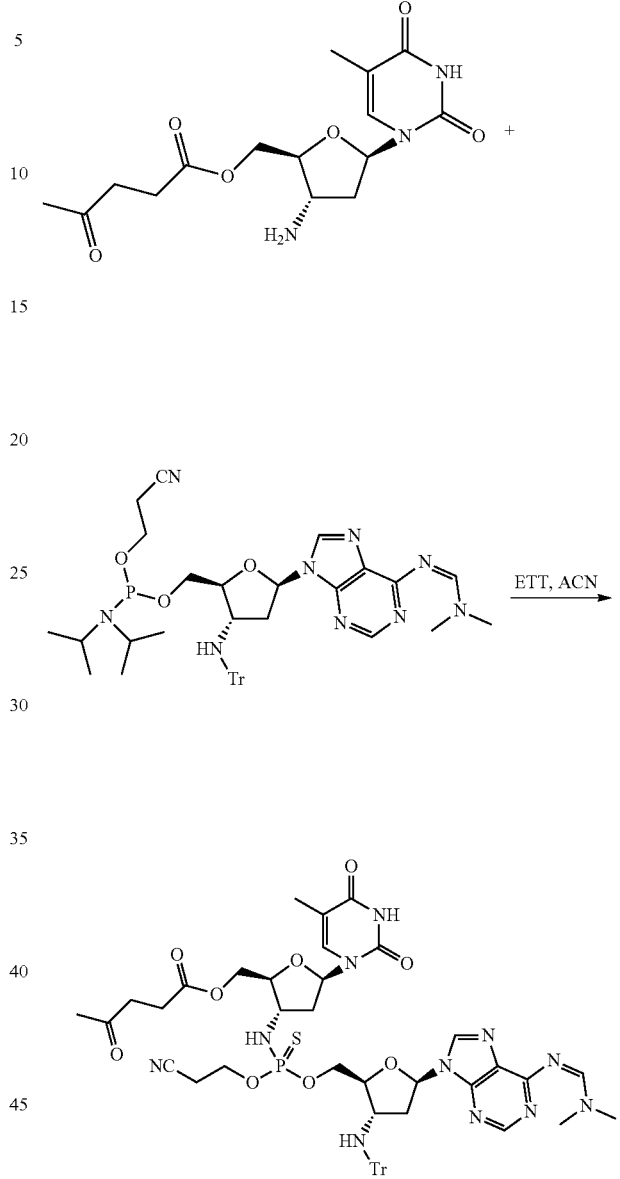

TABLE 9

Coupling and Sulfurization during Dimer Amidate synthesis

| Entry | Starting Material Quantity | Mol. Eq. of reagents | Solvent type and Amount | Reaction time/ temp. | Pdt. Yield Weight | Analysis |
|---|---|---|---|---|---|---|
| 1 | 100 mg | ETT (1.0 eq), Xantane hydride (2.0 eq), Pyridine (1.5 mL) | Acetonitrile (5.0 mL) | RT for 3 + 2 h. | 300 mg (crude) | LCMS |
| 2 | 100 mg | 0.4M ETT (2.0 mL), Xantane hydride (1.2 eq), Pyridine (2.0 mL) | neat | RT for 3 + 2 h. | 350 mg (crude) | LCMS |

A variety of nucleoside monomers were prepared according to the methods described herein which find use in the preparation of the dimer compounds.
Scheme 6 Synthesis of Levulinate protected monomers
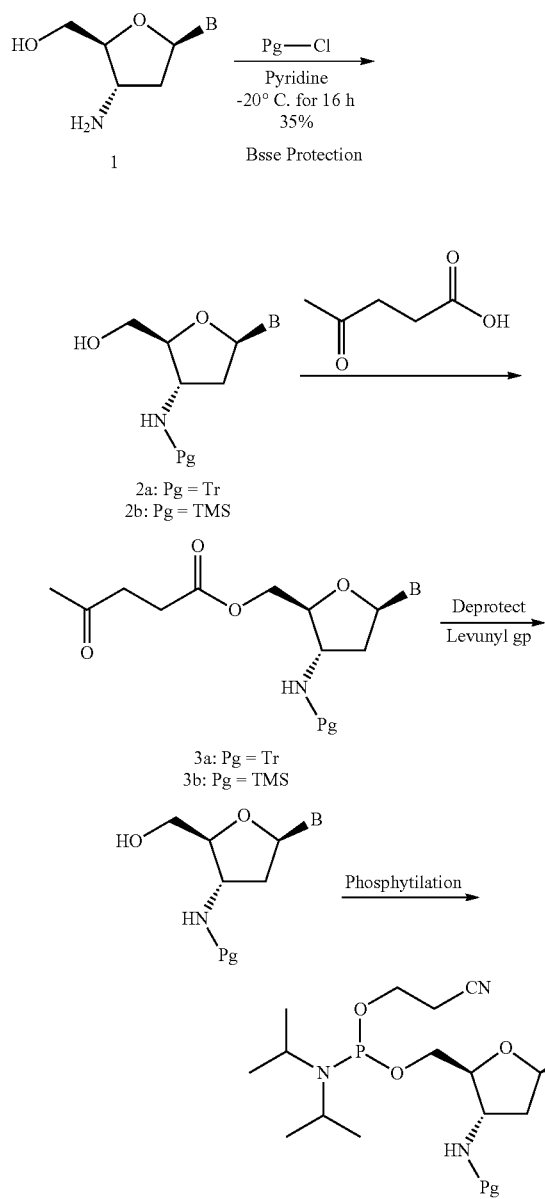
Scheme 7 Synthesis of a bis-DMF A amidite
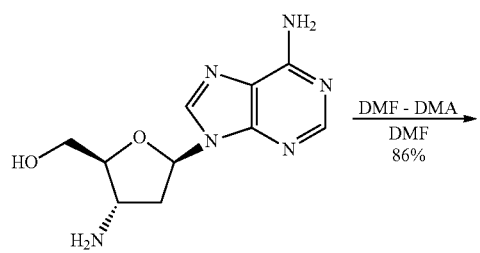
Scheme 8 Synthetic Scheme for MMT, DMT and Pixyl Monomers (A amidites)
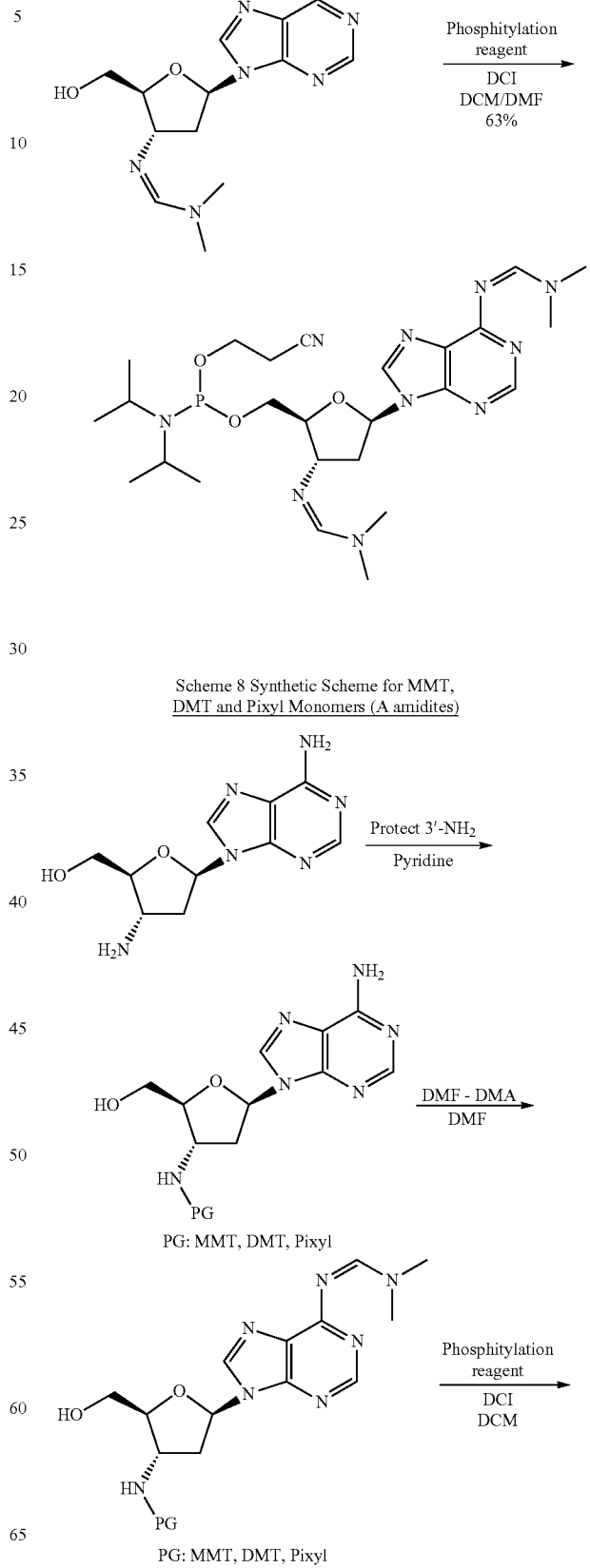

-continued
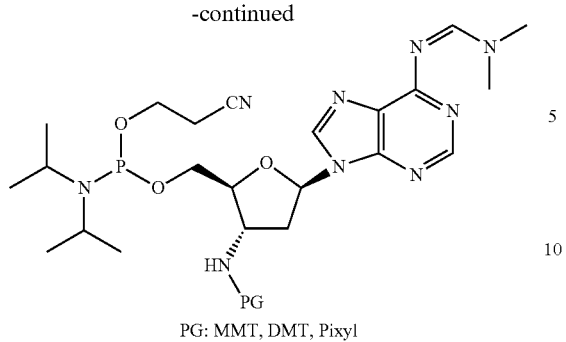
PG: MMT, DMT, Pixyl
| | | |
|---|---|---|
| Amidite A<sup>dmf</sup> (MMT) | 3'-Monomethoxytritylamino-N<sub>6</sub>-dimethylformamidino-2',3'-dideoxyadenosine-5'-(2-cyanoethyl)-N,N-diisopropyl Phosphoramidite | 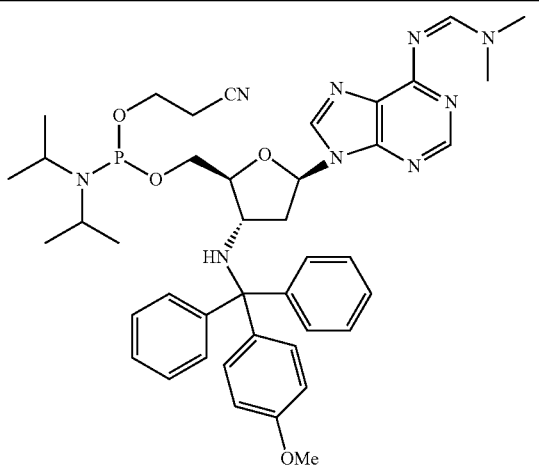 |
| Amidite A<sup>dmf</sup> (pixyl) | 3'-(dimethyl-substituted Pixyl)amino-N<sub>6</sub>-dimethylformamidino-2',3'-dideoxyadenosine-5'-(2-cyanoethyl)-N,N-diisopropyl Phosphoramidite | 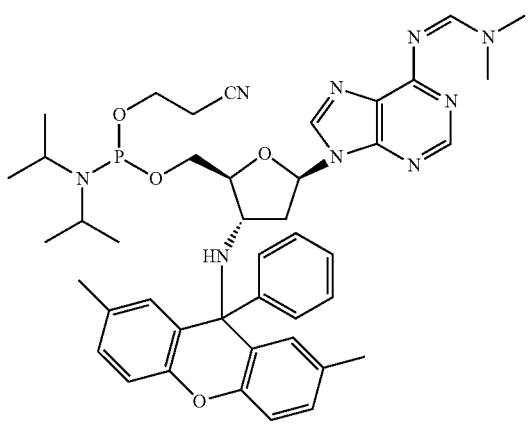 [SMILES: Cc1ccc2c(c1)C(N[C@H]1C[C@H](n3cnc4c(/N=C\N(C)C)ncnc43)O[C@@H]1COP(OCCC#N)N(C(C)C)C(C)C)(c1ccccc1)c1cc(C)ccc1O2] |

-continued

| Amidite A<sup>dmf</sup> (DMT) | 3'-Dimethoxytritylamino-N<sub>6</sub>-dimethylformamidino-2',3'-dideoxyadenosine-5'-(2-cyanoethyl)-N,N-diisopropyl Phosphoramidite | 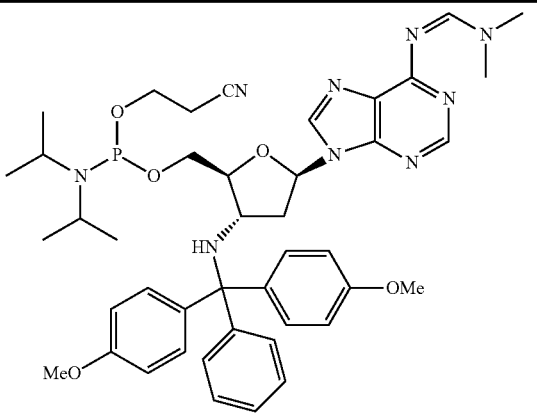 |
|---|---|---|

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Embodiments

The present disclosure provides a composition having less than 1 part in 4 by weight of a (N−1) product relative to a compound or a salt thereof, where the compound includes a polynucleotide having a sequence of 10 or more nucleoside subunits and at least two of the nucleoside subunits are joined by a N3'→P5' phosphoramidate inter-subunit linkage. In some embodiments of the composition, the N3'→P5' phosphoramidate inter-subunit linkage is a N3'→P5' thiophosphoramidate inter-subunit linkage having the structure: 3'-NH—P(S)(OR)—O-5' where R is selected from the group consisting of hydrogen, an alkyl, a substituted alkyl, an aryl, a substituted aryl and a phosphate protecting group, or a salt thereof.

In some embodiments of the composition, the compound includes a polynucleotide having a sequence of 10 or more nucleoside subunits complementary to the RNA component of human telomerase. In some embodiments of the composition, the polynucleotide includes a sequence comprising 13 or more nucleoside subunits complementary to the RNA component of human telomerase. In some embodiments of the composition, the polynucleotide includes between 3 and 50 contiguous nucleoside subunits complementary to the RNA component of human telomerase. In some embodiments of the composition, the nucleoside subunits complementary to the RNA component of human telomerase are all joined by N3'→P5' phosphoramidate inter-subunit linkages. In some embodiments of the composition, the polynucleotide includes a sequence selected from the group consisting of: GTTAGGGTTAG (SEQ ID NO:4), TAGGGTTAGACAA (SEQ ID NO:3) and CAGTTAGGGTTAG (SEQ ID NO:5). In some embodiments of the composition, the polynucleotide includes a 3'amino or a 3'-hydroxyl terminal group.

In some embodiments of the composition, the compound has the structure:

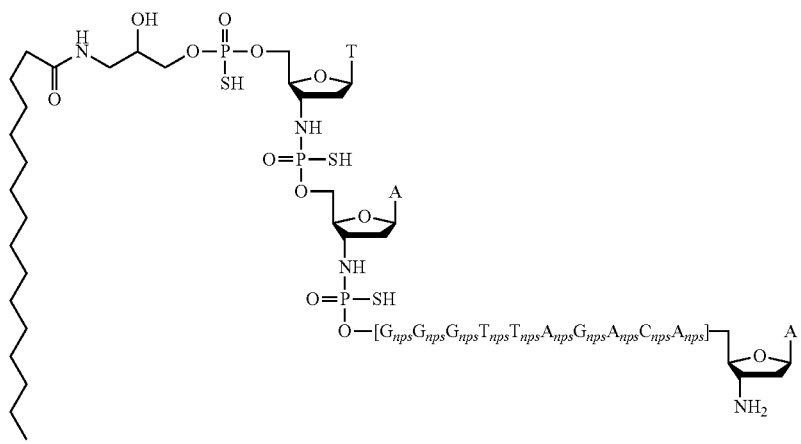

or a salt thereof; where "nps" represents a thiophosphoramidate linkage —NH—P(=O)(SH)—O—, connecting the 3'-carbon of one nucleoside to the 5'-carbon of the adjacent nucleoside. In some embodiments of the composition, the salt is a pharmaceutically acceptable salt.

In some embodiments of the composition, the compound has the structure:

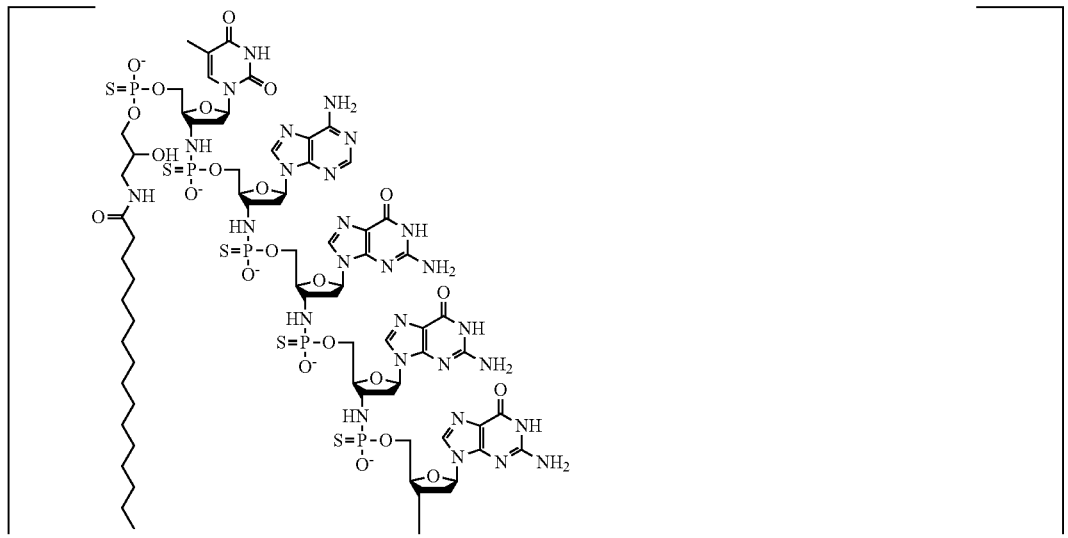

wherein each $M^{x+}$ is independently hydrogen or a counterion of a salt, each x is independently 1, 2 or 3 and n is an integer from 5 to 13. In certain instances, $M^{x+}$ is hydrogen.

In some embodiments of the composition, the compound has the structure:

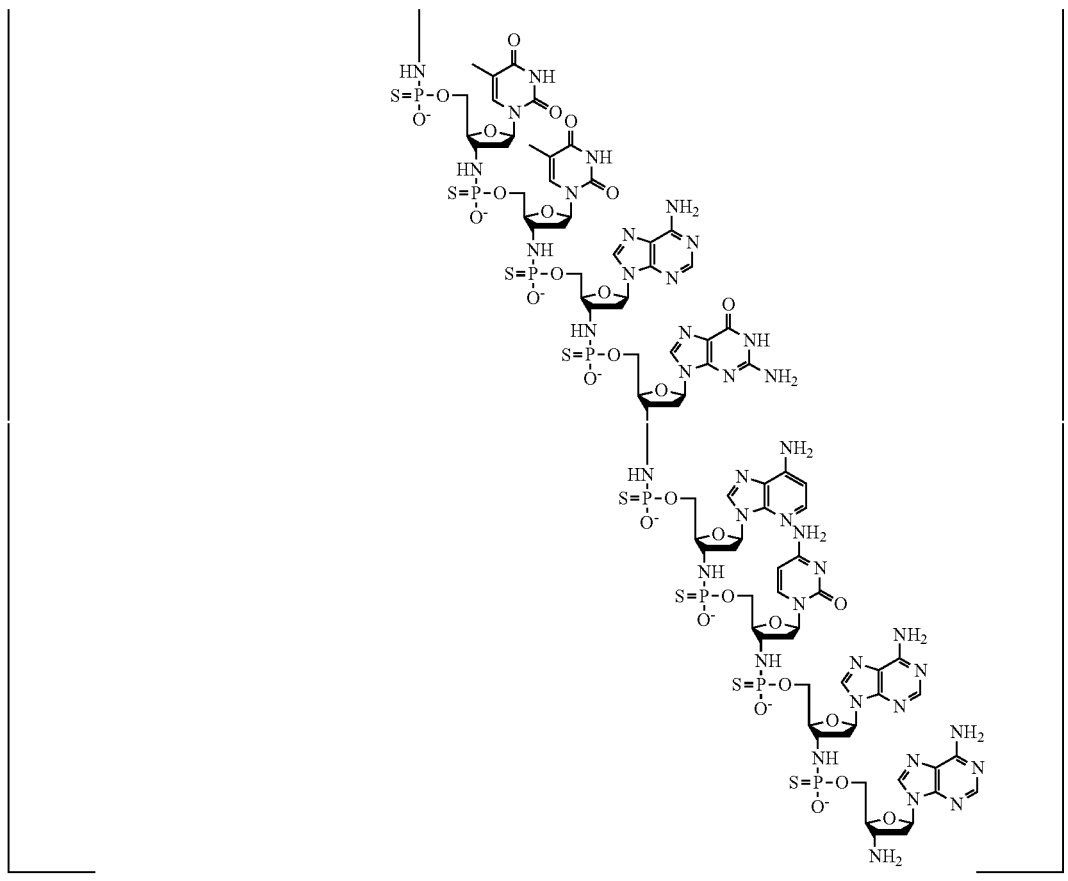

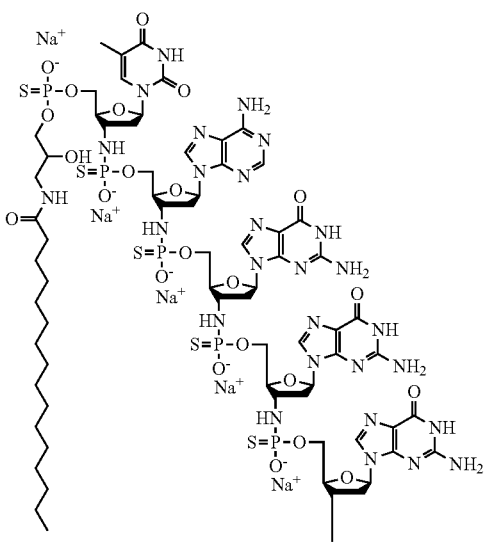
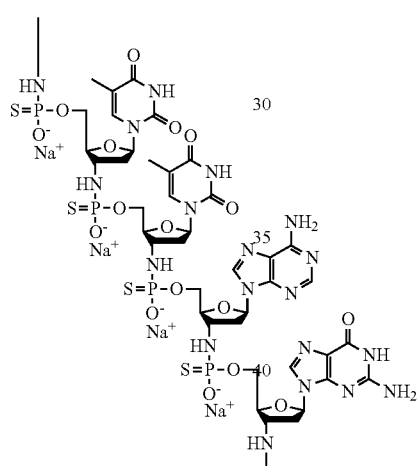
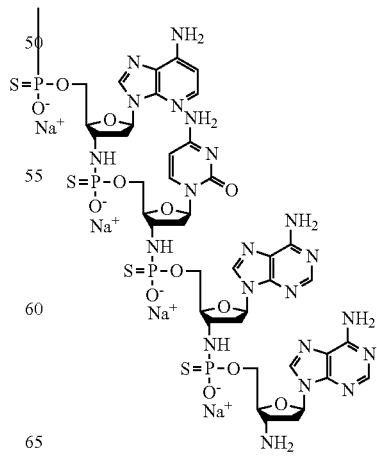

In some embodiments, the composition has less than 1 part in 6 by weight of a (N−1) product relative to the compound. In some embodiments, the composition has less than 1 part in 10 by weight of a (N−1) product relative to the compound. In some embodiments, the composition has less than 1 part in 20 by weight of a (N−1) product relative to the compound. In some embodiments, the composition has less that 1 part in 4 by weight of any (N−x) product relative to the compound. In some embodiments, the composition has less that 40 part in 100 by total weight of (N−x) polynucleotide-containing products relative to the compound. In some embodiments, the composition has the following profile of (N−x) polynucleotide-containing products: less that 1 part in 4 by weight of a (N−1) product relative to the compound; at least 10 parts in 100 by weight of (N−2) and (N−3) products relative to the compound.

The present disclosure provides a compound active pharmaceutical ingredient having less than 11% by weight of a (N−1) product, where the compound or a pharmaceutically acceptable salt thereof includes a polynucleotide having a sequence of 10 or more nucleoside subunits complementary to the RNA component of human telomerase, where at least two of the nucleoside subunits are joined by a N3'→P5' phosphoramidate inter-subunit linkage.

In some embodiments of the compound active pharmaceutical ingredient, the nucleoside subunits complementary to the RNA component of human telomerase are all joined by N3'→P5' thiophosphoramidate inter-subunit linkages. In some embodiments of the compound active pharmaceutical ingredient, the N3'→P5' phosphoramidate inter-subunit linkage is a N3'→P5' thiophosphoramidate inter-subunit linkage having the structure: 3'-NH—P(S)(OR)—O-5' where R is selected from the group consisting of hydrogen, an alkyl, a substituted alkyl, an aryl, a substituted aryl and a phosphate protecting group, or a pharmaceutically acceptable salt thereof.

In some embodiments of the compound active pharmaceutical ingredient, the polynucleotide includes between 10 and 50 contiguous nucleoside subunits complementary to the RNA component of human telomerase. In some embodiments of the compound active pharmaceutical ingredient, the polynucleotide includes a sequence selected from the group consisting of: GTTAGGGTTAG (SEQ ID NO:4); TAGGGTTAGACAA (SEQ ID NO:3); and CAGTTAGGGTTAG (SEQ ID NO:5). In some embodiments of the compound active pharmaceutical ingredient, the polynucleotide includes a 3'amino or a 3'-hydroxyl terminal group.

In some embodiments of the compound active pharmaceutical ingredient, the compound has the structure:

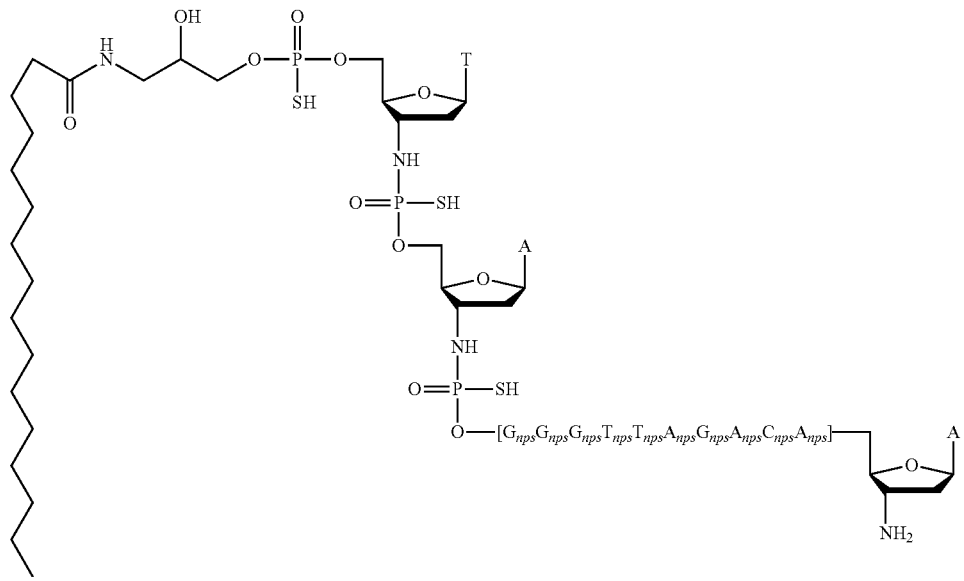

or a pharmaceutically acceptable salt thereof; where "nps" represents a thiophosphoramidate linkage —NH—P(=O)(SH)—O—, connecting the 3'-carbon of one nucleoside to the 5'-carbon of the adjacent nucleoside.

In some embodiments of the compound active pharmaceutical ingredient, the compound has the structure:

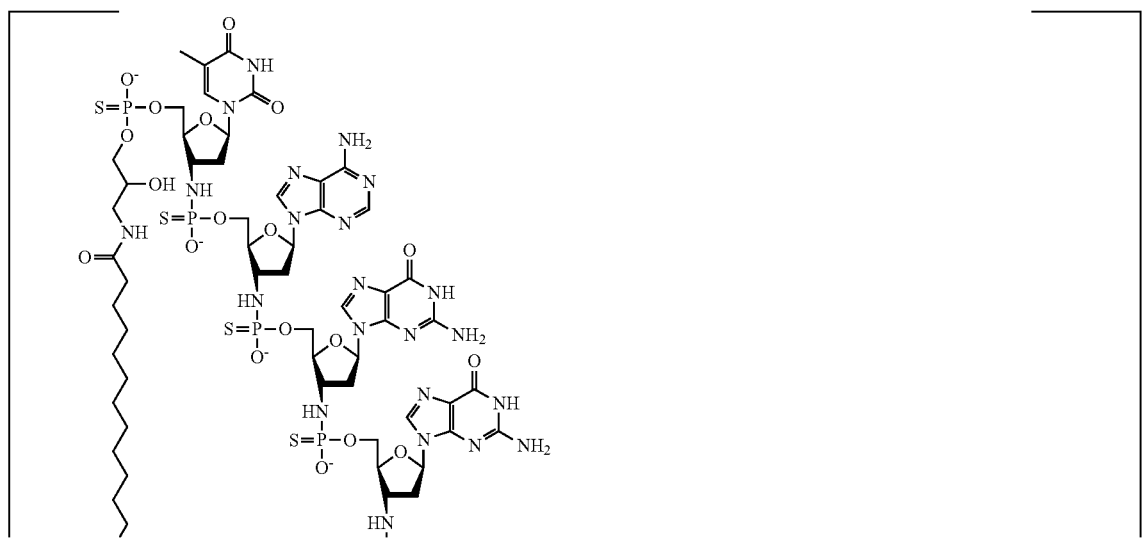
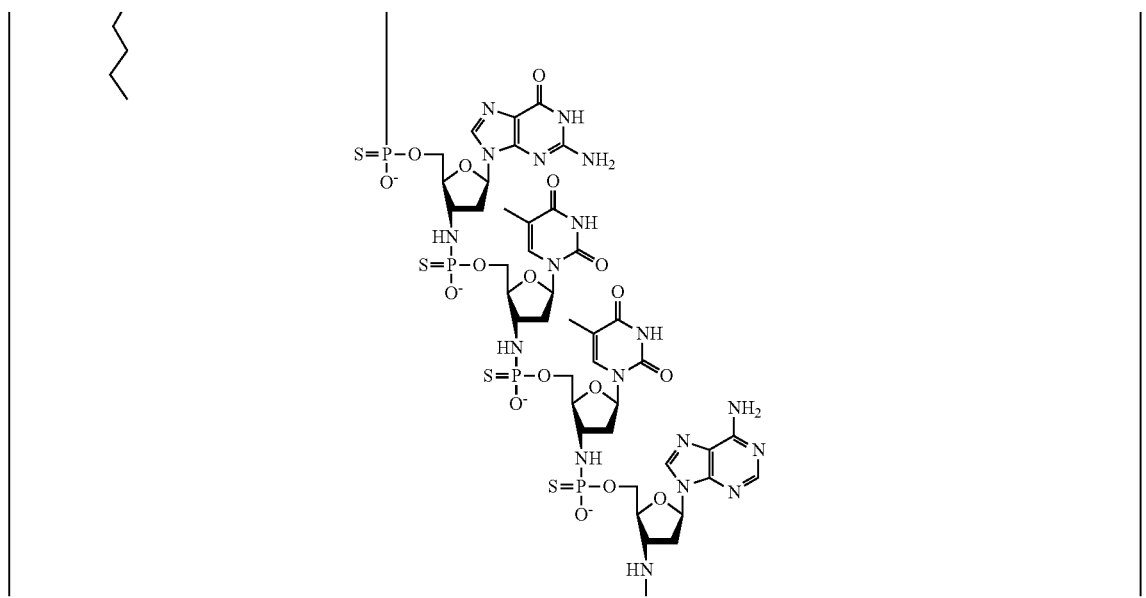

-continued
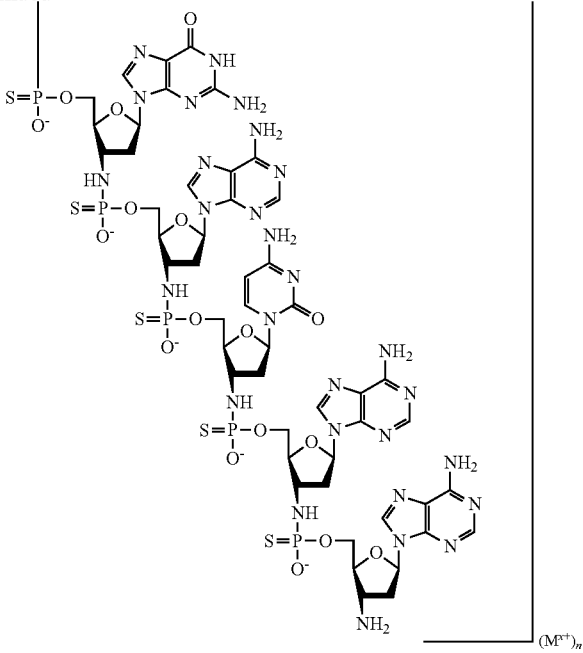
where each $M^{x+}$ is independently hydrogen or a counterion of a pharmaceutically acceptable salt, each x is independently 1, 2 or 3 and n is an integer from 5 to 13. In certain instances, $M^{x+}$ is hydrogen.
In some embodiments of the compound active pharmaceutical ingredient, the compound has the structure:
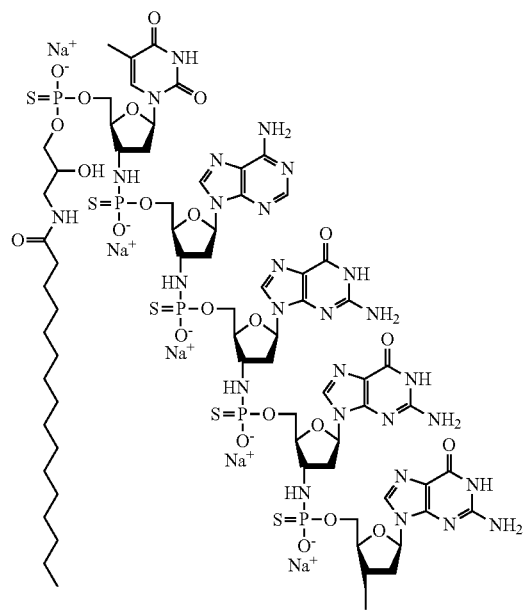

-continued

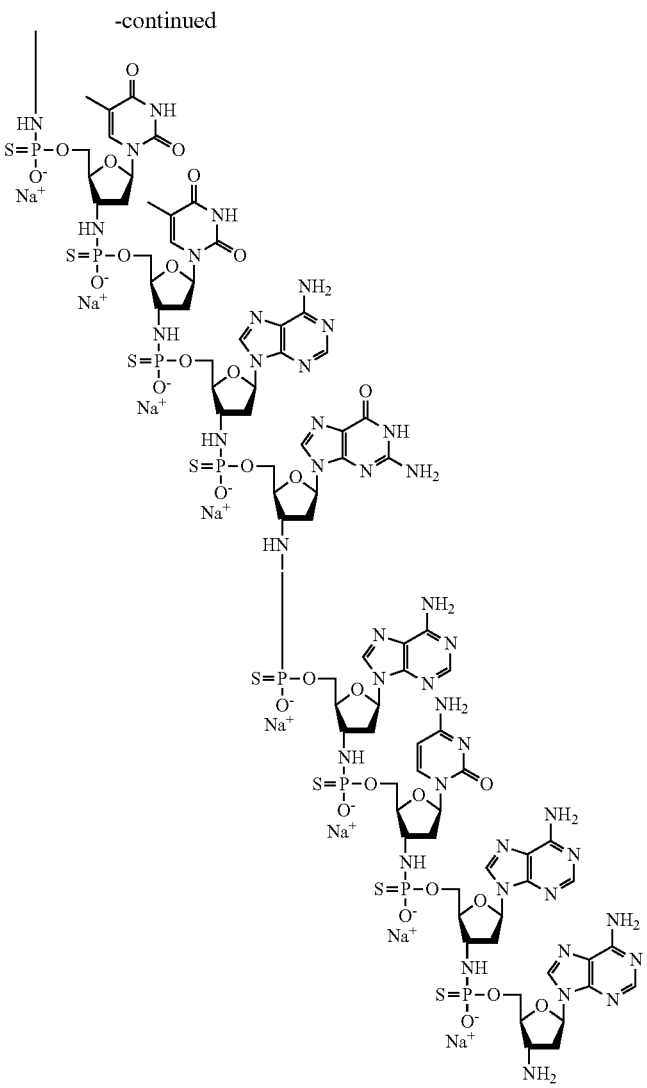

In some embodiments, the compound active pharmaceutical ingredient has less that 9% by weight of the (N−1) product. In some embodiments, the compound active pharmaceutical ingredient has less that 5% by weight of the (N−1) product. In some embodiments, the compound active pharmaceutical ingredient has less that 11% of any (N−x) product. In some embodiments, the compound active pharmaceutical ingredient has less that 45% by weight in total of (N−x) polynucleotide-containing products. In some embodiments, the compound active pharmaceutical ingredient has the following profile of (N−x) polynucleotide-containing products: less that 5% by weight of a (N−1) product; and at least 10% by weight of (N−2) and (N−3) products.

Also provided is a pharmaceutical composition including a composition (e.g., of any one of the embodiments described herein) formulated in a pharmaceutically acceptable excipient. Also provided is a pharmaceutical composition including a compound active pharmaceutical ingredient (e.g., of any one of the embodiments described herein) formulated in a pharmaceutically acceptable excipient.

The present disclosure provides a method of synthesizing a polynucleotide. In some embodiments, the method includes the steps of: (a) deprotecting the protected 3' amino group of a terminal nucleoside attached to a solid phase support, said deprotecting forming a free 3' amino group; (b) contacting the free 3' amino group with a 3'-protected amino-dinucleotide phosphoramidate-5'-phosphoramidite dimer in the presence of a nucleophilic catalyst to form an internucleoside N3'→P5' phosphoramidite linkage; and (c) oxidizing the linkage.

In some embodiments, the method further includes: (a) deprotecting the protected 3' amino group of a terminal nucleoside attached to a solid phase support, said deprotecting forming a free 3' amino group; (b) contacting the free 3' amino group with a 3'-protected aminonucleoside-5'-phosphoramidite monomer in the presence of a nucleophilic catalyst to form an internucleoside N3'→P5' phosphoramidite linkage; and (c) oxidizing the linkage. In some embodiments of the method, the oxidizing the linkage includes sulfurization to produce a thiophosphoramidate linkage. In some embodiments of the method, the oxidizing the linkage produces an oxophosphoramidate linkage.

In some embodiments of the method, the 3'-protected amino-dinucleotide phosphoramidate-5'-phosphoramidite dimer has the formula:

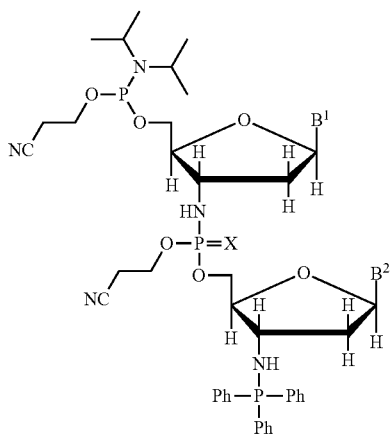

wherein X is O or S and $B^1$ and $B^2$ are each independently a purine, a protected purine, a pyrimidine or a protected pyrimidine, or an analog thereof. In some embodiments of the method, the $B^1$ and $B^2$ are each independently selected from protected adenine, protected cytosine, protected guanine, thymine and uracil. In some embodiments of the method, the $B^1$ and $B^2$ are each independently selected from A(Bz), A(DMF), C(Bz), G(isobutyryl), T and U. In some embodiments of the method, X is S.

In some embodiments of the method, the polynucleotide is of the formula:

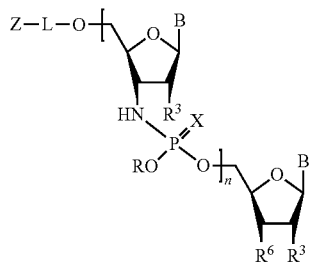

where: each B is independently a purine, a protected purine, a pyrimidine or a protected pyrimidine, or an analog thereof; each X is independently oxygen or sulfur; each $R^3$ is hydrogen, fluoro, or hydroxyl, an alkoxy, a substituted alkoxy or a protected hydroxyl; L is an optional linker; Z is H, a lipid, a support, a carrier, an oligonucleotide, a PEG, a polypeptide, a detectable label, or a tag; $R^6$ is amino, hydroxyl, a protected amino, a protected hydroxy, —O-L-Z or —NH-L-Z; R is hydrogen, an alkyl, a substituted alkyl, an aryl, a substituted aryl, or a phosphate protecting group; and n is an integer of 1 to 1000; or a salt thereof; and the method comprises the steps of: (a) deprotecting a protected 3' amino group of a terminal nucleoside attached to a solid phase support, said deprotecting forming a free 3' amino group; (b) reacting the free 3' amino group with either: (i) a 3'-protected amino-dinucleotide phosphoramidate-5'-phosphoramidite dimer; or (ii) a 3'-protected aminonucleoside-5'-phosphoramidite monomer; in the presence of a nucleophilic catalyst to form an internucleoside N3'→P5' phosphoramidite linkage; (c) oxidizing the linkage; and (d) repeating steps (a) through (c) until the polynucleotide is synthesized, wherein the repeating steps (a) through (c) comprises performing step (b)(i) at least once.

In some embodiments of the method, the oxidizing the linkage comprises sulfurization to produce a thiophosphoramidate linkage. In some embodiments of the method, the oxidizing the linkage produces an oxophosphoramidate linkage. In some embodiments of the method, the polynucleotide comprises a sequence of nucleoside subunits complementary to the RNA component of human telomerase, and wherein at least two of the nucleoside subunits are joined by a N3'→P5' phosphoramidate inter-subunit linkage. In some embodiments of the method, the N3'→P5' phosphoramidate inter-subunit linkage is a N3'→P5' thiophosphoramidate inter-subunit linkage having the structure: 3'-NH—P(S)(OR)—O-5' where R is selected from the group consisting of hydrogen, an alkyl, a substituted alkyl, an aryl, a substituted aryl and a phosphate protecting group, or a salt thereof.

In some embodiments of the method, the polynucleotide includes the sequence TAGGGTTAGACAA. In some embodiments of the method, all of the internucleotide inter-subunit linkages of the TAGGGTTAGACAA sequence are N3'→P5' phosphoramidate inter-subunit linkages. In some embodiments of the method, polynucleotide has the structure:

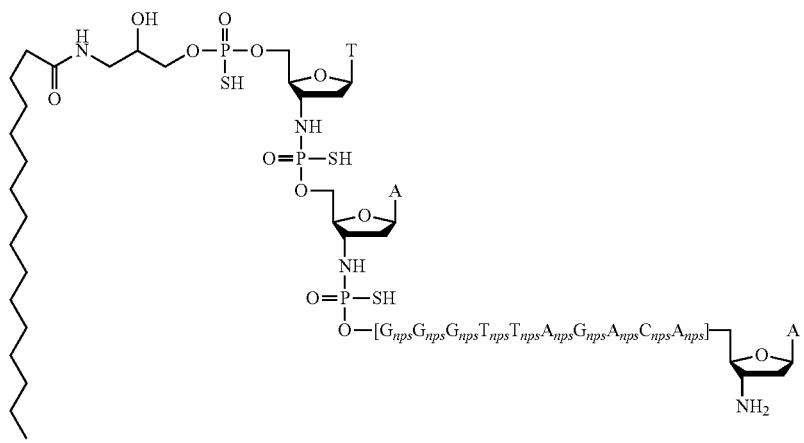

or a salt thereof; where "nps" represents a thiophosphoramidate linkage —NH—P(=O)(SH)—O—, connecting the 3'-carbon of one nucleoside to the 5'-carbon of the adjacent nucleoside.
In some embodiments of the method, the polynucleotide has the structure:
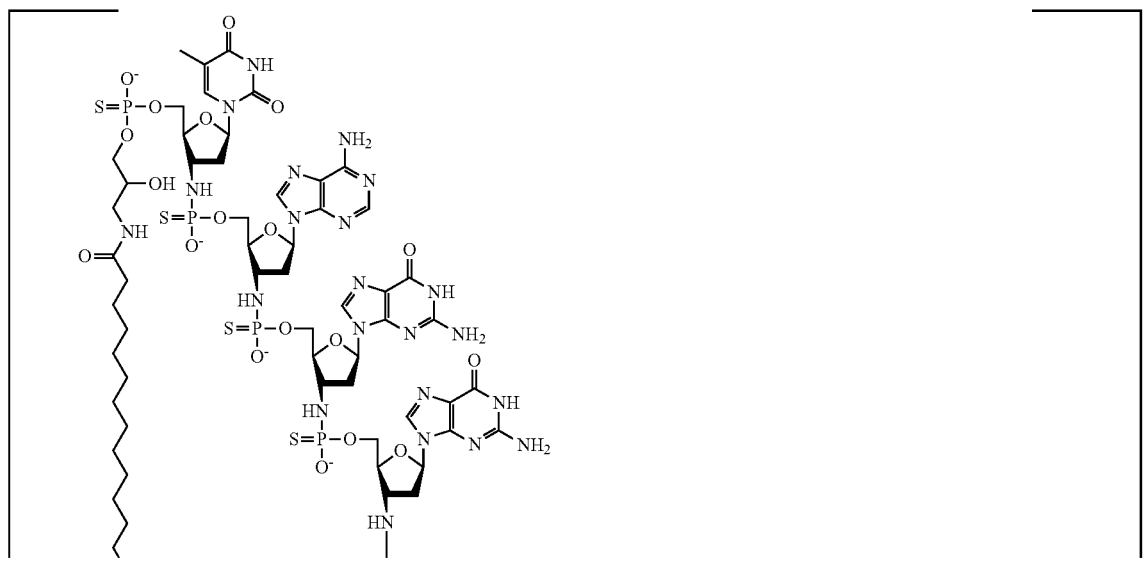
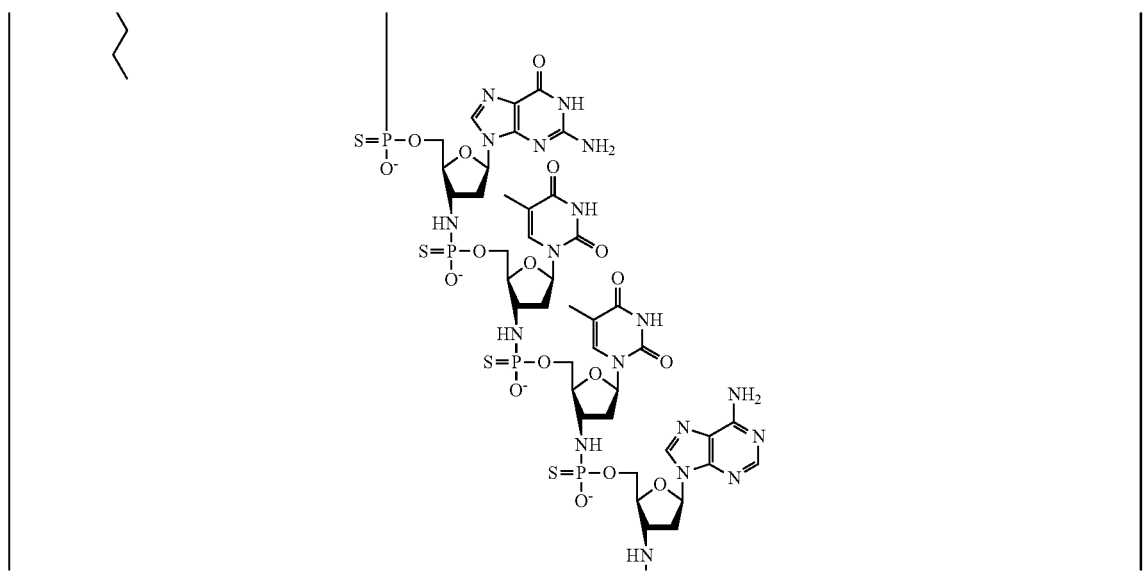

-continued
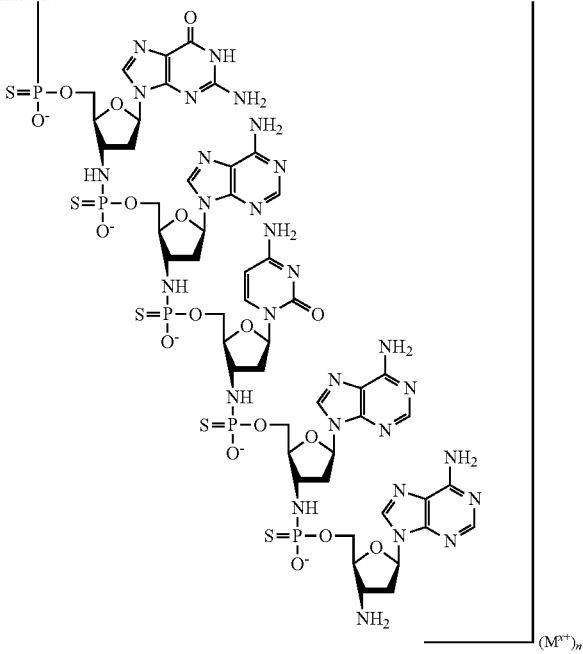
wherein each $M^{x+}$ is independently hydrogen or a counterion of a pharmaceutically acceptable salt, each x is independently 1, 2 or 3 and n is an integer from 5 to 13. In certain instances, $M^{x+}$ is hydrogen.
In some embodiments of the method, the polynucleotide has the structure:
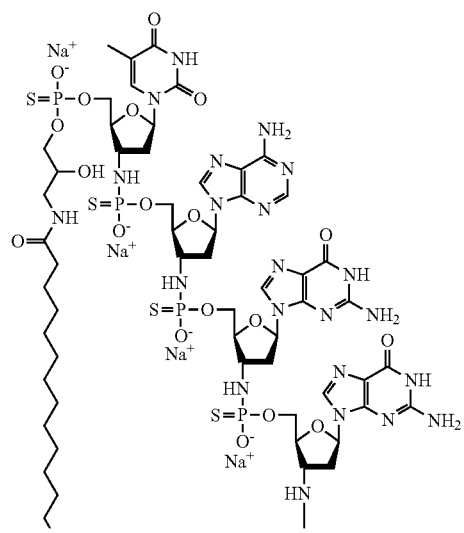

-continued

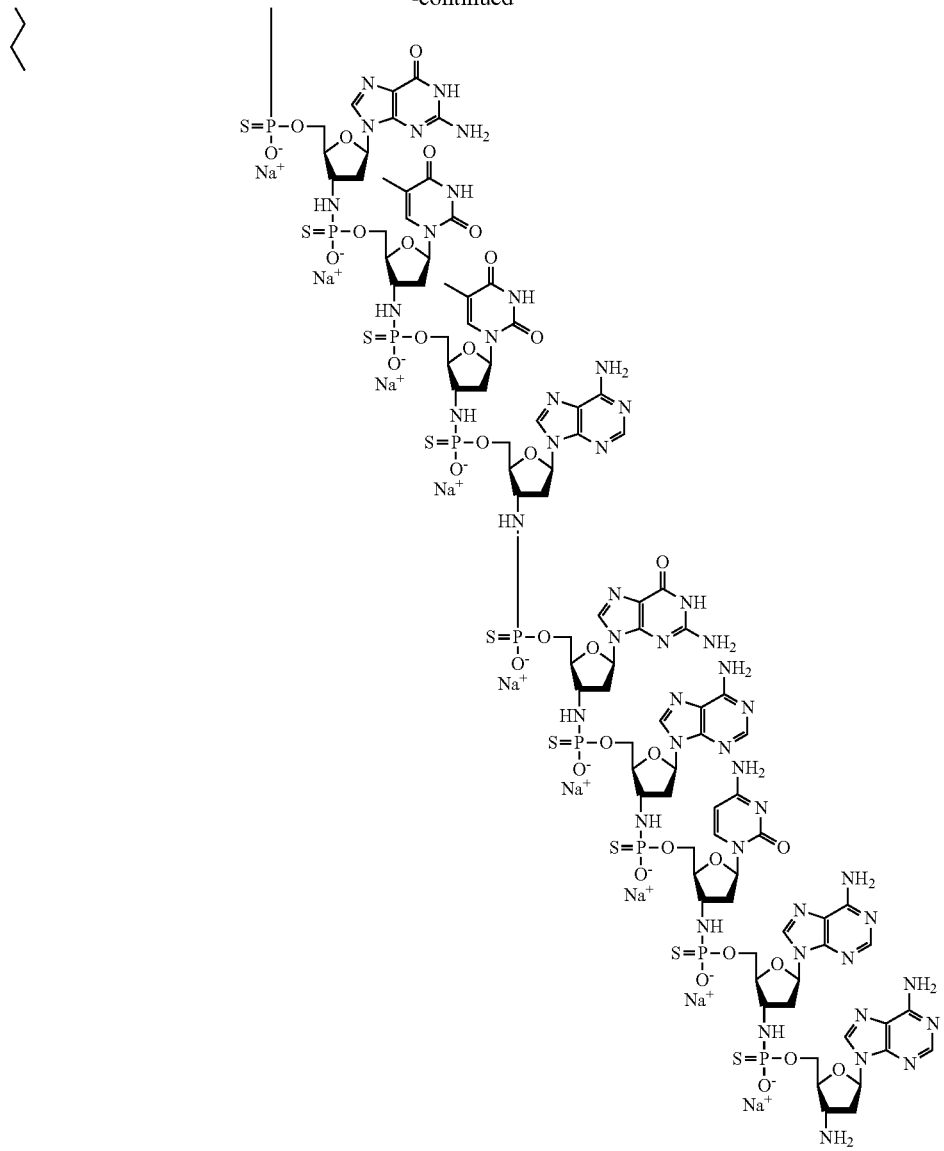

In some embodiments of the method, the C11 nucleotide residue of the TAGGGTTAGACAA sequence derives from a 3'-protected aminonucleoside-5'-phosphoramidite monomer. In some embodiments, the method includes sequential coupling of the following 3'-protected amino-dinucleotide thiophosphoramidate-5'-phosphoramidite dimers TA, GG, GT, TA, GA and AA and 3'-protected aminonucleoside-5'-phosphoramidite monomer C to the solid phase support. In some embodiments of the method, the 3'-protected amino-dinucleotide phosphoramidite-5'-phosphoramidite dimer is described by the formula $X^1X^2$, wherein $X^1$ and $X^2$ are independently selected from protected adenine, protected cytosine, protected guanine, thymine and uracil. In some embodiments of the method, the 3'-protected aminonucleoside-5'-phosphoramidite dimer is selected from protected adenine, protected cytosine, protected guanine, thymine and uracil.

The present disclosure provides a dinucleotide thiophosphoramidate compound described by Formula (II):

Formula (II)

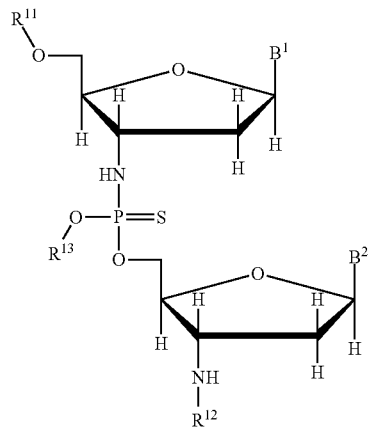

wherein: $B^1$ and $B^2$ are each independently a purine, a protected purine, a pyrimidine or a protected pyrimidine, or an analog thereof; $R^1$ is hydrogen, a protecting group or a phosphoramidite group; and $R^{12}$ and $R^{13}$ are each independently hydrogen or a protecting group; or a salt thereof.

In some embodiments of the compound, $B^1$ and $B^2$ are each independently selected from protected adenine, protected cytosine, protected guanine, thymine and uracil. In some embodiments of the compound, $B^1$ and $B^2$ are each independently selected from A(Bz), A(DMF), C(Bz), G(isobutyryl), T and U. In some embodiments of the compound, $R^{11}$ is a 5'-phosphoramidite; $R^{12}$ is a protecting group and $R^{13}$ is a protecting group. In some embodiments of the compound, $B^1$ is A(Bz) or A(DMF) and $B^2$ is A(Bz) or A(DMF). In some embodiments of the compound, $B^1$ is A(Bz) or A(DMF) and $B^2$ is C(Bz). In some embodiments of the compound, $B^1$ is A(Bz) or A(DMF) and $B^2$ is G(isobutyryl). In some embodiments of the compound, $B^1$ is A(Bz) or A(DMF) and $B^2$ is T. In some embodiments of the compound, $B^1$ is A(Bz) or A(DMF) and $B^2$ is U. In some embodiments of the compound, $B^1$ is C(Bz) and $B^2$ is A(Bz) or A(DMF). In some embodiments of the compound, $B^1$ is C(Bz) and $B^2$ is C(Bz). In some embodiments of the compound, $B^1$ is C(Bz) and $B^2$ is G(isobutyryl). In some embodiments of the compound, $B^1$ is C(Bz) and $B^2$ is T. In some embodiments of the compound, $B^1$ is C(Bz) and $B^2$ is U. In some embodiments of the compound, $B^1$ is G(isobutyryl) and $B^2$ is A(Bz) or A(DMF). In some embodiments of the compound, $B^1$ is G(isobutyryl) and $B^2$ is C(Bz). In some embodiments of the compound, $B^1$ is G(isobutyryl) and $B^2$ is G(isobutyryl). In some embodiments of the compound, $B^1$ is G(isobutyryl) and $B^2$ is T. In some embodiments of the compound, $B^1$ is G(isobutyryl) and $B^2$ is U. In some embodiments of the compound, $B^1$ is T or U and $B^2$ is A(Bz) or A(DMF). In some embodiments of the compound, $B^1$ is T or U and $B^2$ is C(Bz). In some embodiments of the compound, $B^1$ is T or U and $B^2$ is G(isobutyryl). In some embodiments of the compound, $B^1$ is T or U and $B^2$ is T. In some embodiments of the compound, $B^1$ is T or U and $B^2$ is U.

All possible combinations of the above-indicated embodiments are considered to be embraced within the scope of this invention.

What is claimed is:

1. An unpurified synthetic composition comprising:
   a polynucleotide compound having a sequence of N nucleoside subunits wherein at least two of the nucleoside subunits are joined by a N3'→P5' phosphoramidate inter-subunit linkage, or a salt thereof; and
   a 3'-protected amino-dinucleotide phosphoramidate-5'-phosphoramidite dimer,
   wherein the unpurified synthetic composition has less than 1 part in 10 by weight of (N−1) product relative to the polynucleotide compound or a salt thereof, wherein N is 10 or more.

2. The composition of claim 1, wherein the N3'→P5' phosphoramidate inter-subunit linkage is a N3'→P5' thiophosphoramidate inter-subunit linkage having the structure:

3'-NH—P(S)(OR)—O-5' wherein R is selected from the group consisting of hydrogen, an alkyl, a substituted alkyl, an aryl, a substituted aryl and a phosphate protecting group, or a salt thereof.

3. The composition of claim 1, wherein the compound comprises a polynucleotide having a sequence of 10 or more nucleoside subunits complementary to the RNA component of human telomerase.

4. The composition of claim 3, wherein the polynucleotide comprises between 3 and 50 contiguous nucleoside subunits complementary to the RNA component of human telomerase.

5. The composition of claim 3, wherein the nucleoside subunits are all joined by N3'→P5' phosphoramidate inter-subunit linkages.

6. The composition of claim 1, wherein the polynucleotide comprises a sequence selected from the group consisting of: GTTAGGGTTAG (SEQ ID NO:4), TAGGGTTAGACAA (SEQ ID NO:3) and CAGTTAGGGTTAG (SEQ ID NO:5).

7. The composition of claim 6, wherein the compound has the structure:

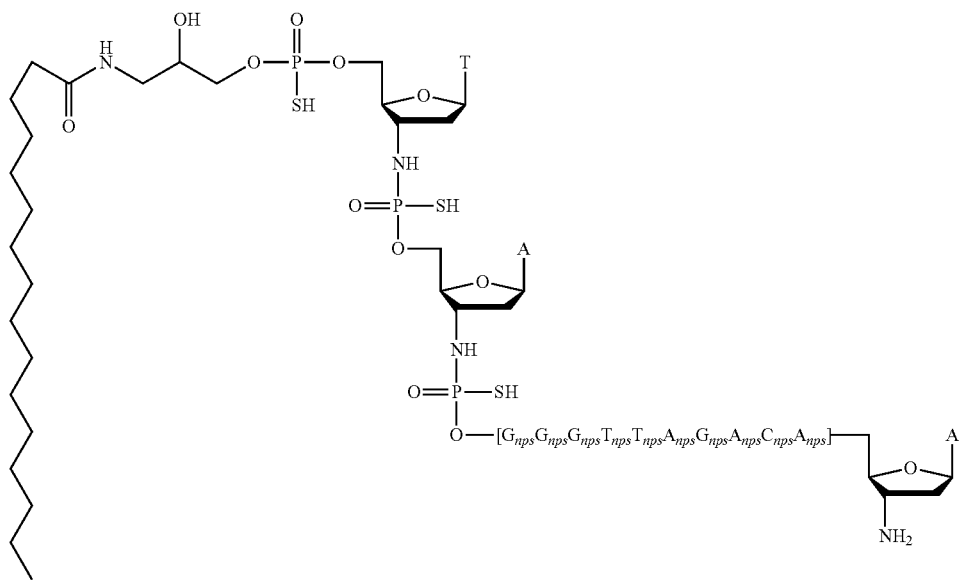
or a salt thereof;
wherein "nps" represents a thiophosphoramidate linkage —NH—P(=O)(SH)—O—, connecting the 3'-carbon of one nucleoside to the 5'-carbon of the adjacent nucleoside.
8. The composition of claim 6, wherein the compound has the structure:
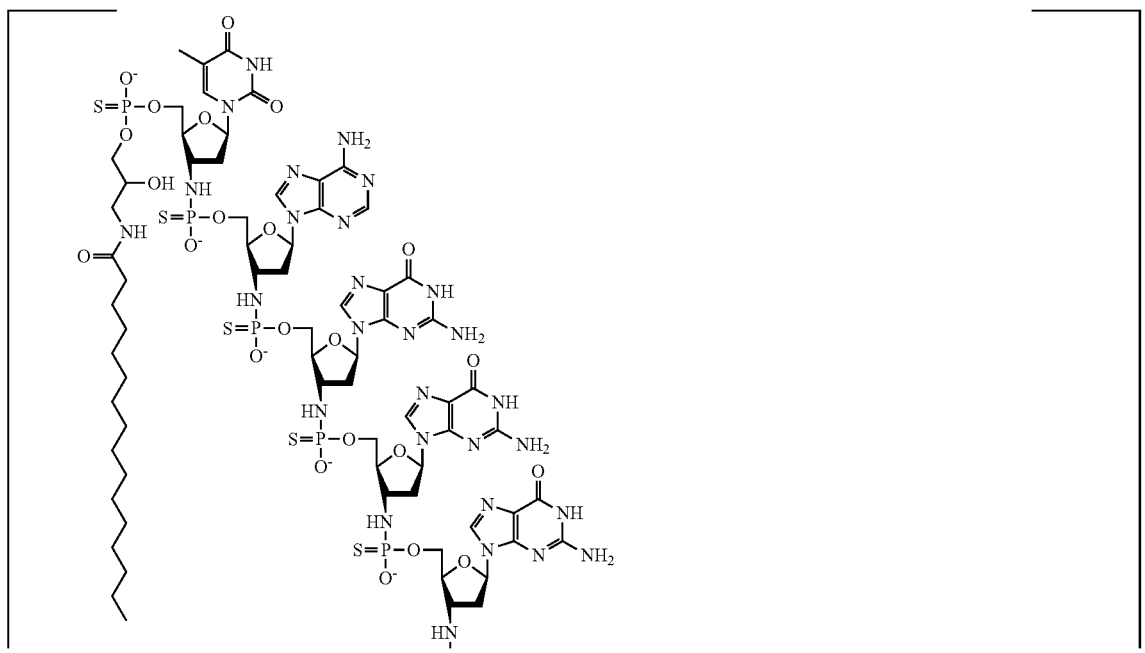

-continued
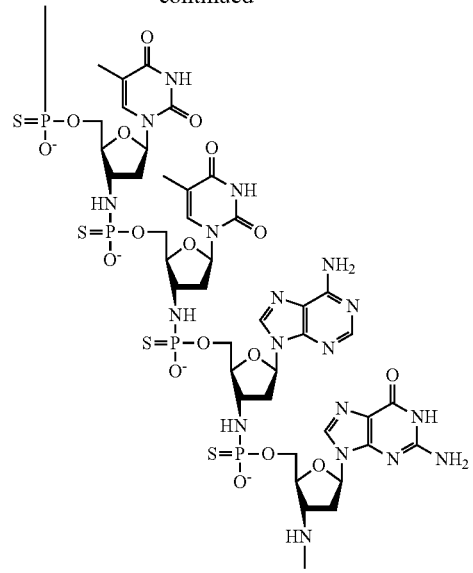
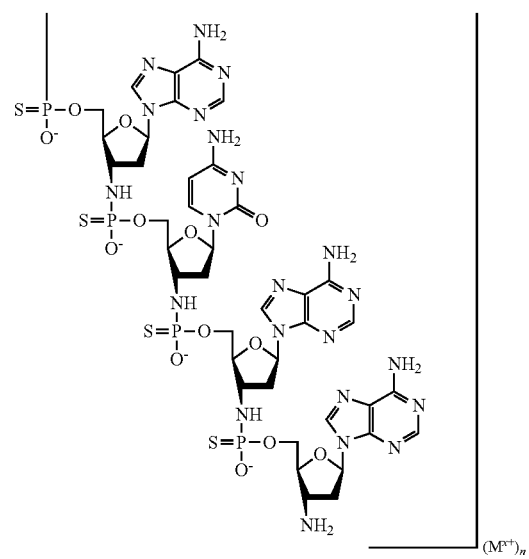
wherein each $M^{x+}$ is independently hydrogen or a counterion of a salt, each x of $M^{x+}$ is independently 1, 2 or 3 and n is an integer from 5 to 13.

9. The composition of claim 6, wherein the compound has the structure:
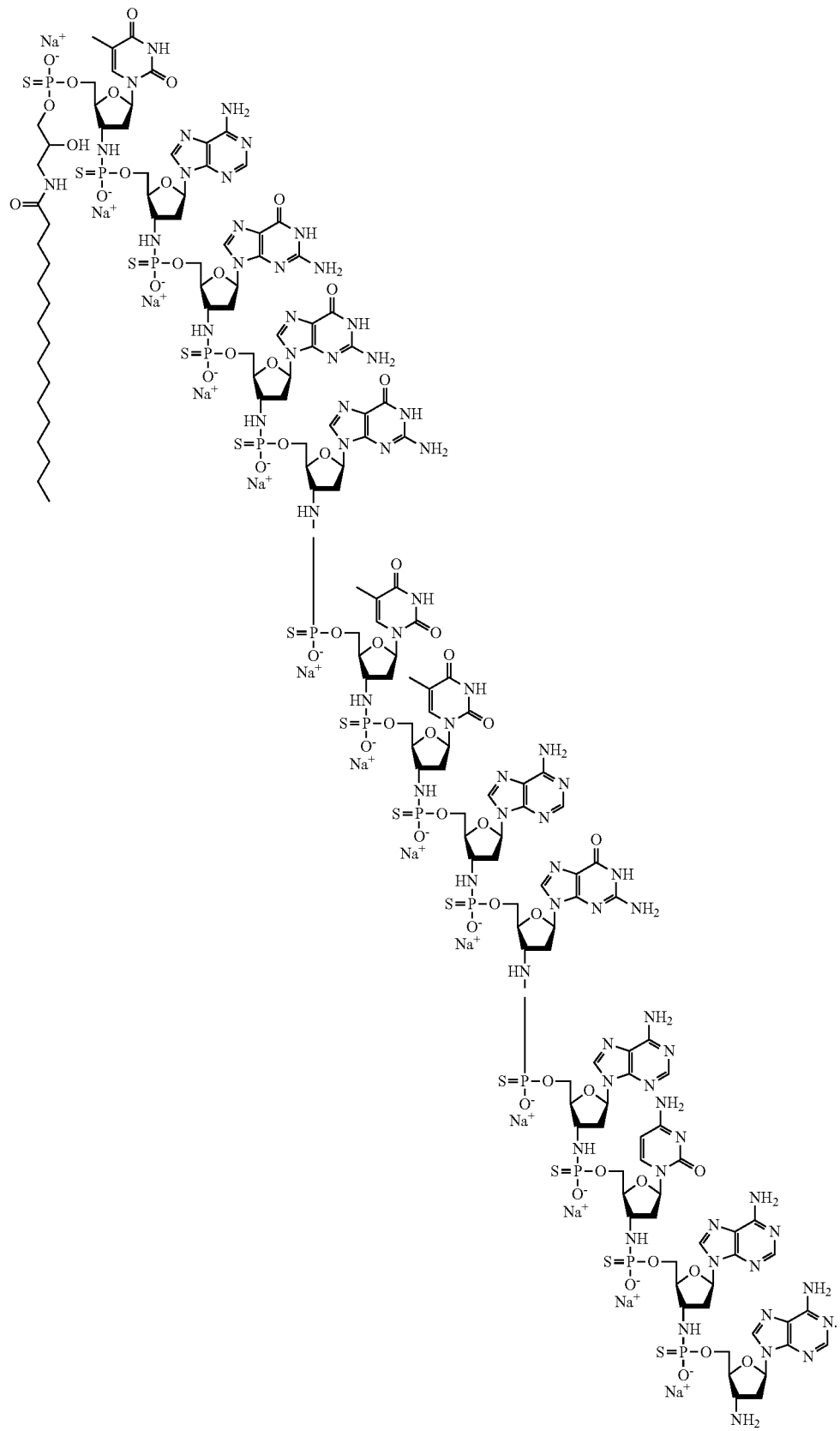

10. The composition of claim 1, having less than 1 part in 20 by weight of (N–1) product relative to the compound.

11. The composition of claim 1, having less than 1 part in 10 by weight of any one (N–x) product relative to the compound, wherein x of (N–x) is 1 to (N–1).

12. The composition of any one of claim 11, having less than 40 parts in 100 by total weight of all (N–x) polynucleotide-containing products relative to the compound, wherein x of (N–x) is 1 to (N–1).

13. The composition of claim 1, having the following profile of (N–x) polynucleotide-containing products, wherein x is 1 to (N–1):
  less than 1 part in 10 by weight of (N–1) product relative to the compound;
  at least 10 parts in 100 by weight of (N–2) and (N–3) products relative to the compound.

14. The composition of claim 1, wherein the nucleoside subunits of the polynucleotide compound independently have the structure:

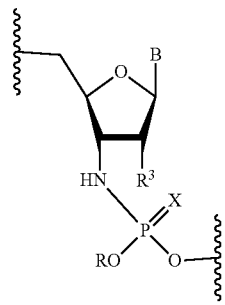

wherein:
  B is a purine, a protected purine, a pyrimidine or a protected pyrimidine, or an analog thereof;
  X is O or S;
  R is selected from the group consisting of hydrogen, an alkyl, a substituted alkyl, an aryl, a substituted aryl, a phosphate protecting group; and
  $R^3$ is selected from hydrogen, O—$R^2$, and halogen, wherein $R^2$ is H, an alkyl, a substituted alkyl and a hydroxyl protecting group.

15. The composition of claim 1, having less than 1 part in 15 by weight of (N–1) product relative to the compound.

16. The composition of claim 1, having less than 1 part in 25 by weight of (N–1) product relative to the compound.

17. The composition of claim 1, wherein N is between 10 and 40.

18. The composition of claim 17, wherein N is between 10 and 30.

19. The composition of claim 18, wherein N is between 10 and 20.

20. The composition of claim 1, having less than 9% by weight of the (N–1) product.

21. The composition of claim 20, having less than 5% by weight of the (N–1) product.

22. The composition of claim 1, having less than 11% of any (N–x) product, wherein x of (N–x) is 1 to (N–1).

23. The composition of claim 1, having the following profile of (N–x) polynucleotide-containing products, wherein x of (N–x) is 1 to (N–1):
  less than 5% by weight of a (N–1) product; and
  at least 10% by weight of (N–2) and (N–3) products.

* * * * *

UNITED STATES PATENT AND TRADEMARK OFFICE
CERTIFICATE OF CORRECTION

| | | |
|---|---|---|
| PATENT NO. | : 11,299,511 B2 | Page 1 of 1 |
| APPLICATION NO. | : 15/705021 | |
| DATED | : April 12, 2022 | |
| INVENTOR(S) | : Ramiya | |

It is certified that error appears in the above-identified patent and that said Letters Patent is hereby corrected as shown below:

In the Specification

In Column 19, Line 48, please replace "HI-phosphonate" with --- H-phosphonate ---;

In Column 22, Line 14, please replace "p-nitro-substituted" with --- β-nitro-substituted ---;

In Column 38, Line 45, please replace "thiphosphorarnidate" with --- thiophosphoramidate ---;

In Column 41, Line 14, please replace "B$^2$" with --- B$^1$ ---;

In Column 102, Line 46, please replace "mole" with --- μmole ---; and

In Column 137, Line 3, please replace "R$^1$" with --- R$^{11}$ ---.

Signed and Sealed this
Fifth Day of July, 2022

Katherine Kelly Vidal
*Director of the United States Patent and Trademark Office*